(12) United States Patent
Andreyev et al.

(10) Patent No.: US 12,037,635 B2
(45) Date of Patent: Jul. 16, 2024

(54) PORTABLE MOLECULAR DIAGNOSTIC DEVICE AND METHODS FOR THE DETECTION OF TARGET VIRUSES

(71) Applicant: Visby Medical, Inc., San Jose, CA (US)

(72) Inventors: Boris Andreyev, Foster City, CA (US); Victor Briones, Gilroy, CA (US); Ryan T. Cena, San Jose, CA (US); Adam De La Zerda, Los Altos, CA (US); Colin Kelly, Brooklyn, NY (US); Gregory Loney, Los Altos, CA (US); Gary Schoolnik, Palo Alto, CA (US); David Swenson, Santa Clara, CA (US)

(73) Assignee: Visby Medical, Inc., San Jose, CA (US)

( * ) Notice: Subject to any disclaimer, the term of this patent is extended or adjusted under 35 U.S.C. 154(b) by 230 days.

(21) Appl. No.: 17/508,359

(22) Filed: Oct. 22, 2021

(65) Prior Publication Data

US 2022/0042076 A1 Feb. 10, 2022

Related U.S. Application Data

(62) Division of application No. 16/186,067, filed on Nov. 9, 2018, now Pat. No. 11,162,130.

(60) Provisional application No. 62/594,905, filed on Dec. 5, 2017, provisional application No. 62/583,789, filed on Nov. 9, 2017.

(51) Int. Cl.
| | |
|---|---|
| *B01L 3/00* | (2006.01) |
| *B01L 7/00* | (2006.01) |
| *C12Q 1/6806* | (2018.01) |
| *C12Q 1/686* | (2018.01) |

(52) U.S. Cl.
CPC .......... *C12Q 1/6806* (2013.01); *B01L 3/5027* (2013.01); *B01L 3/502715* (2013.01); *B01L 7/00* (2013.01); *C12Q 1/686* (2013.01); *B01L 7/52* (2013.01); *B01L 2200/028* (2013.01); *B01L 2200/04* (2013.01); *B01L 2200/10* (2013.01); *B01L 2200/16* (2013.01); *B01L 2300/04* (2013.01); *B01L 2300/087* (2013.01); *B01L 2300/0883* (2013.01); *B01L 2300/1805* (2013.01); *B01L 2400/0487* (2013.01); *C12Q 2600/112* (2013.01); *C12Q 2600/16* (2013.01)

(58) Field of Classification Search
None
See application file for complete search history.

(56) References Cited

U.S. PATENT DOCUMENTS

| | | |
|---|---|---|
| 3,697,227 A | 10/1972 | Goldstein et al. |
| 4,710,355 A | 12/1987 | Ushikubo |
| 4,789,630 A | 12/1988 | Bloch et al. |
| 4,889,692 A | 12/1989 | Holtzman |
| RE33,858 E | 3/1992 | Gropper et al. |
| 5,164,159 A | 11/1992 | Hayashi et al. |
| 5,229,297 A | 7/1993 | Schnipelsky et al. |
| 5,254,479 A | 10/1993 | Chemelli |
| 5,270,183 A | 12/1993 | Corbett et al. |
| 5,273,905 A | 12/1993 | Muller et al. |
| 5,405,585 A | 4/1995 | Coassin |
| 5,429,807 A | 7/1995 | Matson et al. |
| 5,498,392 A | 3/1996 | Wilding et al. |
| 5,631,165 A | 5/1997 | Chupp et al. |
| 5,633,168 A | 5/1997 | Glasscock et al. |
| 5,660,993 A | 8/1997 | Cathey et al. |
| 5,773,234 A | 1/1998 | Pronovost et al. |
| 5,726,026 A | 3/1998 | Wilding et al. |
| 5,882,903 A | 3/1999 | Andrevski et al. |
| 5,922,591 A | 7/1999 | Anderson et al. |

(Continued)

FOREIGN PATENT DOCUMENTS

| | | |
|---|---|---|
| CN | 101538567 | 9/2009 |
| CN | 103789198 A | 5/2014 |

(Continued)

OTHER PUBLICATIONS

Chandler, Reverse Transcriptase (RT) Inhibition of PCR at Low Concentrations of Template and Its Implications for Quantitative RT-PCR, Applied and Environmental Microbiology, 64(2): 669-677, 1998. (Year: 1998).*

(Continued)

*Primary Examiner* — Samuel C Woolwine
*Assistant Examiner* — Carolyn L Greene
(74) *Attorney, Agent, or Firm* — Ambrose, Mills & Lazarow, PLLC

(57) ABSTRACT

A method includes coupling a molecular diagnostic test device to a power source. A biological sample is conveyed into a sample preparation module. The device is then actuated by only a single action to cause the device to perform the following functions without further user action. First, the device heats the sample via a heater of the sample preparation module to lyse a portion of the sample. Second, the device conveys the lysed sample to an amplification module and heats the sample within a reaction volume of the amplification module to amplify a nucleic acid thereby producing an output solution containing a target amplicon. The device then reacts, within a detection module, each of (i) the output solution and (ii) a reagent formulated to produce a signal that indicates a presence of the target amplicon within the output solution. A result associated with the signal is then read.

12 Claims, 34 Drawing Sheets

Specification includes a Sequence Listing.

(56) References Cited

U.S. PATENT DOCUMENTS

| | | |
|---|---|---|
| 5,952,664 A | 9/1999 | Wake et al. |
| 5,976,470 A | 11/1999 | Maiefski et al. |
| 6,039,924 A | 3/2000 | Horn |
| 6,126,804 A | 10/2000 | Andresen |
| 6,146,591 A | 11/2000 | Miller |
| 6,153,425 A | 11/2000 | Kozwich et al. |
| 6,168,760 B1 | 1/2001 | Horn |
| 6,235,479 B1 | 5/2001 | Rogers |
| 6,261,431 B1 | 7/2001 | Mathies et al. |
| 6,303,081 B1 | 10/2001 | Mink et al. |
| 6,313,471 B1 | 11/2001 | Giebeler et al. |
| 6,365,378 B1 | 4/2002 | Hirota et al. |
| 6,369,893 B1 | 4/2002 | Christel et al. |
| 6,374,684 B1 | 4/2002 | Dority |
| 6,416,718 B1 | 7/2002 | Maiefski et al. |
| 6,426,215 B1 | 7/2002 | Sandell |
| 6,514,750 B2 | 2/2003 | Bordenkircher et al. |
| 6,610,499 B1 | 8/2003 | Fulwyler et al. |
| 6,645,758 B1 | 11/2003 | Schnipelsky et al. |
| 6,649,378 B1 | 11/2003 | Kozwich et al. |
| 6,656,744 B2 | 12/2003 | Pronovost et al. |
| 6,677,151 B2 | 1/2004 | Sandell |
| 6,767,512 B1 | 7/2004 | Lurz et al. |
| 6,780,380 B2 | 8/2004 | Hunnell et al. |
| 6,780,617 B2 | 8/2004 | Chen |
| 6,781,056 B1 | 8/2004 | O'Rourke et al. |
| 6,813,568 B2 | 11/2004 | Powell et al. |
| 6,821,771 B2 | 11/2004 | Festoc |
| 6,875,403 B2 | 4/2005 | Liu et al. |
| 6,893,879 B2 | 5/2005 | Petersen et al. |
| 6,901,217 B2 | 5/2005 | Gamboa et al. |
| 6,911,181 B1 | 6/2005 | McNeil |
| 6,990,290 B2 | 1/2006 | Kylberg et al. |
| 7,041,481 B2 | 5/2006 | Anderson et al. |
| 7,144,742 B2 | 12/2006 | Boehringer et al. |
| 7,179,639 B2 | 2/2007 | Pottathil et al. |
| 7,189,522 B2 | 3/2007 | Esfandiari |
| 7,192,721 B1 | 3/2007 | Esfandiari |
| 7,235,216 B2 | 6/2007 | Kiselev et al. |
| 7,297,313 B1 | 11/2007 | Northrup et al. |
| 7,341,697 B2 | 3/2008 | Takeuchi et al. |
| 7,377,291 B2 | 5/2008 | Moon et al. |
| 7,378,285 B2 | 5/2008 | Lambotte et al. |
| 7,384,782 B2 | 6/2008 | Nakatani et al. |
| 7,416,892 B2 | 8/2008 | Battrell et al. |
| 7,438,852 B2 | 10/2008 | Tung et al. |
| 7,459,302 B2 | 12/2008 | Reid et al. |
| 7,491,551 B2 | 2/2009 | Boehringer et al. |
| 7,517,495 B2 | 4/2009 | Wu et al. |
| 7,544,324 B2 | 6/2009 | Tung et al. |
| 7,550,112 B2 | 6/2009 | Gou et al. |
| 7,553,675 B2 | 6/2009 | Jerome et al. |
| 7,569,382 B2 | 8/2009 | Li |
| 7,579,172 B2 | 8/2009 | Cho et al. |
| 7,592,139 B2 | 9/2009 | West et al. |
| 7,632,687 B2 | 12/2009 | Gokhan |
| 7,648,835 B2 | 1/2010 | Breidford et al. |
| 7,682,801 B2 | 3/2010 | Esfandiari |
| 7,691,644 B2 | 4/2010 | Lambotte et al. |
| 7,705,339 B2 | 4/2010 | Smith et al. |
| 7,709,250 B2 | 5/2010 | Corbett et al. |
| 7,754,452 B2 | 7/2010 | Kim et al. |
| 7,767,439 B2 | 8/2010 | Oh et al. |
| 7,794,656 B2 | 9/2010 | Liang et al. |
| 7,799,521 B2 | 9/2010 | Chen et al. |
| 7,837,939 B2 | 11/2010 | Tung et al. |
| 7,858,396 B2 | 12/2010 | Corstjens et al. |
| 7,871,568 B2 | 1/2011 | Liang et al. |
| 7,879,293 B2 | 2/2011 | Niedbala et al. |
| 7,914,986 B2 | 3/2011 | Nunn |
| 7,915,013 B2 | 3/2011 | Cho et al. |
| 7,959,877 B2 | 6/2011 | Esfandiari |
| 7,985,716 B2 | 7/2011 | Yershov et al. |
| 7,988,915 B2 | 8/2011 | Lee et al. |
| 7,998,757 B2 | 8/2011 | Darrigrand et al. |
| 8,008,046 B2 | 8/2011 | Maltezos et al. |
| 8,008,080 B2 | 8/2011 | Tokhtuev et al. |
| 8,012,427 B2 | 9/2011 | Bommarito et al. |
| 8,018,593 B2 | 9/2011 | Tan et al. |
| 8,048,386 B2 | 11/2011 | Dority et al. |
| 8,062,883 B2 | 11/2011 | Woudenberg et al. |
| 8,075,854 B2 | 12/2011 | Yang et al. |
| 8,076,129 B2 | 12/2011 | Hanafusa et al. |
| 8,088,616 B2 | 1/2012 | Handique |
| 8,110,148 B2 | 2/2012 | Ball et al. |
| 8,110,392 B2 | 2/2012 | Battrell et al. |
| 8,133,671 B2 | 3/2012 | Williams et al. |
| 8,133,703 B2 | 3/2012 | Ching et al. |
| 8,163,489 B2 | 4/2012 | Murray et al. |
| 8,163,535 B2 | 4/2012 | Reed et al. |
| 8,169,610 B2 | 5/2012 | Oldham et al. |
| 8,173,077 B2 | 5/2012 | Korampally et al. |
| 8,187,557 B2 | 5/2012 | Van Atta et al. |
| 8,198,074 B2 | 6/2012 | Moriwaki et al. |
| 8,216,832 B2 | 7/2012 | Battrell et al. |
| 8,231,844 B2 | 7/2012 | Gorfinkel |
| 8,232,091 B2 | 7/2012 | Maltezos et al. |
| 8,232,094 B2 | 7/2012 | Hasson et al. |
| 8,247,221 B2 | 8/2012 | Fawcett |
| 8,263,392 B2 | 9/2012 | Gale et al. |
| 8,277,763 B2 | 10/2012 | Steinmann et al. |
| 8,278,091 B2 | 10/2012 | Rutter et al. |
| 8,298,763 B2 | 10/2012 | Regan |
| 8,323,583 B2 | 12/2012 | Gou et al. |
| 8,329,453 B2 | 12/2012 | Battrell et al. |
| 8,343,442 B2 | 1/2013 | McBride et al. |
| 8,343,754 B2 | 1/2013 | Wittwer et al. |
| 8,357,490 B2 | 1/2013 | Froehlich et al. |
| 8,372,340 B2 | 2/2013 | Bird et al. |
| 8,389,960 B2 | 3/2013 | Pieprzyk et al. |
| 8,394,608 B2 | 3/2013 | Ririe et al. |
| 8,394,626 B2 | 3/2013 | Ramsey et al. |
| 8,426,134 B2 | 4/2013 | Piepenburg et al. |
| 8,435,461 B2 | 5/2013 | Kirby et al. |
| 8,448,824 B2 | 5/2013 | DiPerna |
| 8,492,136 B2 | 7/2013 | Carlisle et al. |
| 8,507,259 B2 | 8/2013 | Esfandiari |
| 8,557,518 B2 | 10/2013 | Jovanovich et al. |
| 8,580,575 B2 | 11/2013 | Hanafusa |
| 8,597,937 B2 | 12/2013 | Ward et al. |
| 8,603,835 B2 | 12/2013 | Esfandiari |
| 8,617,486 B2 | 12/2013 | Kirby et al. |
| 8,629,264 B2 | 1/2014 | Reed et al. |
| 8,637,250 B2 | 1/2014 | Jenison |
| 8,663,976 B2 | 3/2014 | Chung et al. |
| 8,673,239 B2 | 3/2014 | Niedbala et al. |
| 8,691,561 B2 | 4/2014 | Igata |
| 8,722,426 B2 | 5/2014 | Lambotte et al. |
| 8,728,765 B2 | 5/2014 | Ching et al. |
| 8,735,103 B2 | 5/2014 | Chung et al. |
| 8,765,367 B2 | 7/2014 | Breidenthal et al. |
| 8,765,454 B2 | 7/2014 | Zhou et al. |
| 8,772,017 B2 | 7/2014 | Battrell et al. |
| 8,795,592 B2 | 8/2014 | Eiriksson |
| 8,859,199 B2 | 10/2014 | Hellyer et al. |
| 8,865,458 B2 | 10/2014 | Ramsey et al. |
| 8,871,155 B2 | 10/2014 | Wu et al. |
| 8,877,450 B2 | 11/2014 | Esfandiari |
| 8,894,946 B2 | 11/2014 | Nielsen et al. |
| 8,895,255 B1 | 11/2014 | Goldberg et al. |
| 8,900,828 B2 | 12/2014 | Smith et al. |
| 8,900,853 B2 | 12/2014 | Verhaar et al. |
| 8,911,941 B2 | 12/2014 | Michlitsch |
| 8,911,949 B2 | 12/2014 | Bertrand et al. |
| 8,916,375 B2 | 12/2014 | Landers et al. |
| 8,945,843 B2 | 2/2015 | Alvino et al. |
| 8,975,027 B2 | 3/2015 | Gale et al. |
| 8,980,177 B2 | 3/2015 | Carlisle et al. |
| 8,980,561 B1 | 3/2015 | Cai et al. |
| 8,986,927 B2 | 3/2015 | Lee et al. |
| 8,992,854 B2 | 3/2015 | Brewster et al. |
| 9,011,770 B2 | 4/2015 | Wu et al. |
| 9,012,236 B2 | 4/2015 | Jovanovich et al. |
| 9,023,639 B2 | 5/2015 | Kim et al. |

(56) References Cited

U.S. PATENT DOCUMENTS

| | | |
|---|---|---|
| 9,034,168 B2 | 5/2015 | Khattak et al. |
| 9,044,729 B2 | 6/2015 | Rengifo et al. |
| 9,150,907 B2 | 10/2015 | Shaikh et al. |
| 9,169,521 B1 | 10/2015 | Rajagopal et al. |
| 9,207,236 B2 | 12/2015 | Cary |
| 9,207,241 B2 | 12/2015 | Lambotte et al. |
| 9,238,833 B2 | 1/2016 | Chen et al. |
| 9,243,288 B2 | 1/2016 | Ness et al. |
| 9,260,750 B2 | 2/2016 | Hillebrand et al. |
| 9,268,911 B2 | 2/2016 | Sia et al. |
| 9,387,478 B2 | 7/2016 | Bergstedt et al. |
| 9,445,749 B2 | 9/2016 | Erickson et al. |
| 9,453,255 B2 | 9/2016 | Ozawa et al. |
| 9,469,871 B2 | 10/2016 | Bearinger et al. |
| 9,475,049 B2 | 10/2016 | Siciliano |
| D776,290 S | 1/2017 | Wan et al. |
| 9,551,038 B2 | 1/2017 | Seo et al. |
| 9,623,415 B2 | 4/2017 | Andreyev et al. |
| 9,686,395 B2 | 6/2017 | Erickson et al. |
| 9,718,058 B2 | 8/2017 | Khattak et al. |
| 9,725,754 B2 | 8/2017 | Boyle et al. |
| 9,752,182 B2 | 9/2017 | Collier et al. |
| 9,787,815 B2 | 10/2017 | Erickson et al. |
| 9,789,483 B2 | 10/2017 | Khattak et al. |
| 10,040,069 B2 | 8/2018 | Moore et al. |
| 10,052,629 B2 | 8/2018 | Andreyev et al. |
| 10,112,196 B2 | 10/2018 | Andreyev et al. |
| 10,112,197 B2 | 10/2018 | Andreyev et al. |
| 10,124,334 B2 | 11/2018 | Andreyev et al. |
| 10,146,909 B2 | 12/2018 | Dimov et al. |
| 10,173,182 B2 | 1/2019 | Tachibana et al. |
| 10,195,610 B2 | 2/2019 | Tang et al. |
| 10,233,483 B2 | 3/2019 | Talebpour et al. |
| 10,603,664 B2 | 3/2020 | Khattak |
| 11,080,848 B2 | 8/2021 | Dimov et al. |
| 11,162,130 B2 | 11/2021 | Andreyev et al. |
| 11,167,285 B2 | 11/2021 | Andreyev et al. |
| 11,168,354 B2 | 11/2021 | Andreyev et al. |
| 11,273,443 B2 | 3/2022 | Andreyev et al. |
| 2001/0055799 A1 | 12/2001 | Baunoch et al. |
| 2002/0037520 A1 | 3/2002 | Nikiforov et al. |
| 2003/0027203 A1 | 2/2003 | Fields |
| 2003/0027244 A1 | 2/2003 | Colston et al. |
| 2003/0178302 A1 | 9/2003 | Bhullar et al. |
| 2004/0018502 A1 | 1/2004 | Makino et al. |
| 2004/0110141 A1 | 6/2004 | Pusey et al. |
| 2004/0209331 A1 | 10/2004 | Ririe |
| 2004/0224317 A1 | 11/2004 | Kordunsky et al. |
| 2004/0251426 A1 | 12/2004 | Birk et al. |
| 2005/0064598 A1 | 3/2005 | Yuan et al. |
| 2005/0100946 A1 | 5/2005 | Lipshutz et al. |
| 2005/0142036 A1 | 6/2005 | Kim et al. |
| 2005/0194316 A1 | 9/2005 | Pourahmadi et al. |
| 2005/0227275 A1 | 10/2005 | Jung et al. |
| 2006/0127924 A1 | 6/2006 | Hellyer et al. |
| 2006/0160205 A1 | 7/2006 | Blackburn et al. |
| 2006/0177841 A1 | 8/2006 | Wangh et al. |
| 2006/0246493 A1 | 11/2006 | Jensen et al. |
| 2006/0258012 A1 | 11/2006 | Yang et al. |
| 2007/0026391 A1 | 2/2007 | Stoughton et al. |
| 2007/0036691 A1 | 2/2007 | Lin et al. |
| 2007/0042427 A1 | 2/2007 | Gerdes et al. |
| 2007/0154922 A1 | 7/2007 | Collier et al. |
| 2007/0178603 A1 | 8/2007 | Takii et al. |
| 2007/0284360 A1 | 12/2007 | Santoruvo et al. |
| 2007/0292941 A1 | 12/2007 | Handique et al. |
| 2008/0026451 A1 | 1/2008 | Braman et al. |
| 2008/0038737 A1 | 2/2008 | Smith et al. |
| 2008/0050735 A1 | 2/2008 | Pushnova |
| 2008/0057572 A1 | 3/2008 | Petersen et al. |
| 2008/0113391 A1 | 5/2008 | Gibbons et al. |
| 2008/0145852 A1 | 6/2008 | Shuber |
| 2008/0153078 A1 | 6/2008 | Braman et al. |
| 2008/0220468 A1 | 9/2008 | Windeyer et al. |
| 2008/0274513 A1 | 11/2008 | Shenderov et al. |
| 2008/0280285 A1 | 11/2008 | Chen et al. |
| 2009/0021728 A1 | 1/2009 | Heinz et al. |
| 2009/0029422 A1 | 1/2009 | Hanafusa et al. |
| 2009/0042256 A1 | 2/2009 | Hanafusa et al. |
| 2009/0130745 A1 | 5/2009 | Williams et al. |
| 2009/0148933 A1 | 6/2009 | Battrell et al. |
| 2009/0186344 A1 | 7/2009 | Farinas |
| 2009/0215072 A1 | 8/2009 | McDevitt et al. |
| 2009/0325276 A1 | 12/2009 | Battrell et al. |
| 2010/0003683 A1 | 1/2010 | Sarofim et al. |
| 2010/0025242 A1 | 2/2010 | Pamula |
| 2010/0035349 A1 | 2/2010 | Bau et al. |
| 2010/0113762 A1 | 5/2010 | Ball et al. |
| 2010/0173393 A1 | 7/2010 | Handique et al. |
| 2010/0210038 A1 | 8/2010 | Blatt et al. |
| 2010/0291588 A1 | 11/2010 | McDevitt et al. |
| 2010/0297640 A1 | 11/2010 | Kumar et al. |
| 2011/0020876 A1 | 1/2011 | Wilding et al. |
| 2011/0039303 A1 | 2/2011 | Janovich et al. |
| 2011/0151577 A1 | 6/2011 | Zhang et al. |
| 2011/0160090 A1 | 6/2011 | Cary |
| 2011/0203688 A1 | 8/2011 | Reed et al. |
| 2011/0211331 A1 | 9/2011 | Alkjaer et al. |
| 2011/0227551 A1 | 9/2011 | Black |
| 2011/0244466 A1 | 10/2011 | Juncosa et al. |
| 2011/0269191 A1 | 11/2011 | Belgrader et al. |
| 2011/0275055 A1 | 11/2011 | Conner |
| 2011/0300545 A1 | 12/2011 | Cano et al. |
| 2011/0308313 A1 | 12/2011 | Azimi et al. |
| 2011/0312074 A1 | 12/2011 | Azimi et al. |
| 2011/0312666 A1 | 12/2011 | Azimi et al. |
| 2011/0312787 A1 | 12/2011 | Silverbrook et al. |
| 2011/0312841 A1 | 12/2011 | Silverbrook et al. |
| 2011/0313148 A1 | 12/2011 | Christ et al. |
| 2012/0021454 A1 | 1/2012 | Bikker et al. |
| 2012/0064534 A1 | 3/2012 | Pipper et al. |
| 2012/0070878 A1 | 3/2012 | Fink et al. |
| 2012/0088294 A1 | 4/2012 | Sun et al. |
| 2012/0115738 A1 | 5/2012 | Zhou et al. |
| 2012/0130061 A1 | 5/2012 | Himmelreich et al. |
| 2012/0135511 A1 | 5/2012 | Battrell et al. |
| 2012/0141337 A1 | 6/2012 | Maltezos et al. |
| 2012/0264114 A1 | 10/2012 | Wacogne et al. |
| 2012/0264202 A1 | 10/2012 | Walker et al. |
| 2012/0282681 A1 | 11/2012 | Teixeira et al. |
| 2012/0282684 A1 | 11/2012 | Fritchie et al. |
| 2012/0288897 A1 | 11/2012 | Ching et al. |
| 2013/0040296 A1 | 2/2013 | Tulp et al. |
| 2013/0053255 A1 | 2/2013 | Vangbo et al. |
| 2013/0078736 A1 | 3/2013 | Grover et al. |
| 2013/0115712 A1 | 5/2013 | Yu et al. |
| 2013/0118900 A1 | 5/2013 | Reimitz et al. |
| 2013/0149710 A1 | 6/2013 | Yoon et al. |
| 2013/0171640 A1 | 7/2013 | Kwon et al. |
| 2013/0210080 A1 | 8/2013 | Rajagopal et al. |
| 2013/0217026 A1 | 8/2013 | Egan et al. |
| 2013/0220781 A1 | 8/2013 | Czarnecki |
| 2013/0225801 A1 | 8/2013 | Christoffel |
| 2014/0017687 A1 | 1/2014 | Wimberger-Friedl et al. |
| 2014/0044609 A1 | 2/2014 | Prusik et al. |
| 2014/0045191 A1 | 2/2014 | DeJohn et al. |
| 2014/0051159 A1 | 2/2014 | Bergstedt et al. |
| 2014/0073013 A1 | 3/2014 | Gorman et al. |
| 2014/0087359 A1 | 3/2014 | Njoroge et al. |
| 2014/0098252 A1 | 4/2014 | Chang et al. |
| 2014/0120539 A1 | 5/2014 | Tanner et al. |
| 2014/0199685 A1 | 7/2014 | Lambotte et al. |
| 2014/0274770 A1 | 9/2014 | Pack |
| 2014/0329301 A1 | 11/2014 | Handique |
| 2015/0017641 A1 | 1/2015 | Korpela |
| 2015/0031087 A1 | 1/2015 | Nagai et al. |
| 2015/0136604 A1* | 5/2015 | Nielsen ............ G01N 27/44743 204/453 |
| 2015/0159195 A1 | 6/2015 | Leclipteux et al. |
| 2015/0176057 A1 | 6/2015 | Smith et al. |
| 2015/0182966 A1 | 7/2015 | Coursey et al. |
| 2015/0240298 A1 | 8/2015 | Piepenburg et al. |
| 2015/0247190 A1 | 9/2015 | Ismagilov et al. |
| 2015/0258273 A1 | 9/2015 | Payne et al. |

(56) References Cited

U.S. PATENT DOCUMENTS

| | | |
|---|---|---|
| 2015/0290639 A1 | 10/2015 | Evtodienko |
| 2015/0346097 A1 | 12/2015 | Battrell et al. |
| 2015/0361419 A1 | 12/2015 | Kim et al. |
| 2016/0008811 A1 | 1/2016 | Laser et al. |
| 2016/0054316 A1 | 2/2016 | Egan et al. |
| 2016/0144362 A1 | 5/2016 | Lee et al. |
| 2016/0186240 A1* | 6/2016 | Andreyev ............. B01L 3/5029 435/287.2 |
| 2016/0193603 A1 | 7/2016 | Battrell et al. |
| 2016/0222442 A1 | 8/2016 | Cary |
| 2016/0251698 A1 | 9/2016 | Laermer et al. |
| 2016/0256870 A1 | 9/2016 | Ismagilov et al. |
| 2016/0263577 A1 | 9/2016 | Ismagilov et al. |
| 2016/0281149 A1 | 9/2016 | Hassibi et al. |
| 2016/0289669 A1 | 10/2016 | Fan et al. |
| 2016/0310904 A1 | 10/2016 | Liu et al. |
| 2016/0310948 A1 | 10/2016 | Nowakowski et al. |
| 2016/0313298 A1 | 10/2016 | Wright et al. |
| 2017/0021356 A1 | 1/2017 | Dority et al. |
| 2017/0058324 A1 | 3/2017 | Balog et al. |
| 2017/0087553 A1 | 3/2017 | Zenhausern et al. |
| 2017/0121756 A1 | 5/2017 | Abate et al. |
| 2017/0152510 A1 | 6/2017 | Lorenz |
| 2017/0173585 A1 | 6/2017 | Mahony et al. |
| 2017/0182495 A1 | 6/2017 | Strey et al. |
| 2017/0247745 A1 | 8/2017 | Schultz et al. |
| 2017/0304829 A1 | 10/2017 | Andreyev et al. |
| 2018/0135108 A1 | 5/2018 | Etchebarne |
| 2018/0135110 A1 | 5/2018 | Saxena et al. |
| 2018/0304260 A1 | 10/2018 | Thomas et al. |
| 2019/0022643 A1 | 1/2019 | Andreyev et al. |
| 2019/0030532 A1 | 1/2019 | Andreyev et al. |
| 2019/0040451 A1 | 2/2019 | Mahony et al. |
| 2019/0060895 A1 | 2/2019 | Myers, III et al. |
| 2019/0070610 A1 | 3/2019 | Haworth et al. |
| 2019/0076841 A1 | 3/2019 | Myers, III et al. |
| 2019/0083975 A1 | 3/2019 | Mitra et al. |
| 2019/0094114 A1 | 3/2019 | Myers, III et al. |
| 2019/0136226 A1 | 5/2019 | Swenson et al. |
| 2019/0151844 A1 | 5/2019 | Andreyev et al. |
| 2019/0169677 A1 | 6/2019 | Andreyev et al. |
| 2019/0193077 A1 | 6/2019 | Andreyev et al. |
| 2019/0232283 A1 | 8/2019 | Andreyev et al. |
| 2019/0232293 A1 | 8/2019 | Tang et al. |
| 2020/0086324 A1 | 3/2020 | Swenson et al. |
| 2020/0346213 A1 | 11/2020 | Andreyev et al. |
| 2020/0406256 A1 | 12/2020 | Andreyev et al. |
| 2020/0406257 A1 | 12/2020 | Andreyev et al. |
| 2020/0408750 A1 | 12/2020 | Khattak |
| 2021/0039097 A1 | 2/2021 | Andreyev et al. |
| 2021/0071236 A1 | 3/2021 | Andreyev et al. |
| 2021/0299669 A1 | 9/2021 | Swenson et al. |
| 2022/0055032 A1 | 2/2022 | Andreyev et al. |
| 2022/0186208 A1 | 6/2022 | Swenson et al. |
| 2022/0203365 A1 | 6/2022 | Abraham et al. |
| 2022/0372557 A1 | 11/2022 | Ciopyk et al. |

FOREIGN PATENT DOCUMENTS

| | | |
|---|---|---|
| CN | 105239164 | 1/2016 |
| CN | 105349530 | 2/2016 |
| CN | 108371961 | 8/2018 |
| EP | 1347833 B1 | 10/2011 |
| EP | 2682480 A1 | 1/2014 |
| IL | 242807 | 11/2015 |
| WO | WO2001/049416 A1 | 7/2001 |
| WO | WO2005/040331 | 5/2005 |
| WO | WO2007/061943 | 5/2007 |
| WO | WO2008/082432 | 7/2008 |
| WO | WO2008/149111 | 12/2008 |
| WO | WO2009/047804 A2 | 4/2009 |
| WO | WO2014/004852 A2 | 1/2014 |
| WO | WO2014/035986 A1 | 3/2014 |
| WO | WO2014/144548 A2 | 9/2014 |
| WO | WO2015/035260 A1 | 3/2015 |
| WO | WO2015/138343 A1 | 9/2015 |
| WO | WO2015/138648 A1 | 9/2015 |
| WO | WO2015/164770 A1 | 10/2015 |
| WO | WO2016/040523 A1 | 3/2016 |
| WO | WO2016/109691 A1 | 7/2016 |
| WO | WO2016/203019 A1 | 12/2016 |
| WO | WO2017/090043 A1 | 6/2017 |
| WO | WO2017/151195 | 9/2017 |
| WO | WO2017/160840 A1 | 9/2017 |
| WO | WO2017/197040 A1 | 11/2017 |
| WO | WO2018/005710 A1 | 1/2018 |
| WO | WO2018/005870 A1 | 1/2018 |
| WO | WO2018/119443 | 6/2018 |
| WO | WO2019/094784 A1 | 5/2019 |
| WO | WO2023/018896 | 2/2023 |

OTHER PUBLICATIONS

International Search Report and Written Opinion for International Application No. PCT/US2015/019497, dated Jun. 8, 2015.
International Search Report and Written Opinion for International Application No. PCT/US2015/049247, mailed Jan. 12, 2016.
International Search Report and Written Opinion for International Application No. PCT/US2015/068101, mailed May 5, 2016.
Non-final Office Action for U.S. Appl. No. 15/474,083, mailed Aug. 24, 2017.
International Search Report and Written Opinion for International Application No. PCT/US2017/040112, mailed Nov. 9, 2017.
International Search Report and Written Opinion for International Application No. PCT/US2017/039844, mailed Dec. 7, 2017.
Final Office Action for U.S. Appl. No. 15/474,083, mailed Jan. 25, 2018.
Office Action for U.S. Appl. No. 15/586,780, mailed Feb. 6, 2018.
Advisory Action for U.S. Appl. No. 15/474,083, mailed Mar. 26, 2018.
Extended European Search Report for European Application No. 15876276.5, mailed Aug. 7, 2018.
Invitation to Pay Additional Fees for International Application No. PCT/US18/60117, mailed Feb. 8, 2019.
U.S. Appl. No. 14/984,573 First Action Interview Pilot Program Pre-Interview Communication dated Aug. 16, 2016.
International Search Report and Written Opinion for International Application No. PCT/US2018/060117, mailed Apr. 12, 2019.
Extended European Search Report for European Application No. 17821297.3, mailed Dec. 17, 2019.
Office Action for AU Application No. 2017290753, mailed Dec. 24, 2020.
Office Action for U.S. Appl. No. 17/017,165, mailed Jan. 21, 2021.
Office Action for U.S. Appl. No. 17/070,562, mailed Jan. 22, 2021.
Office Action for U.S. Appl. No. 17/092,629, mailed Apr. 29, 2021.
Examination Report No. 2 for AU Application No. 2018364741, mailed Feb. 19, 2021.
Office Action for CN Application No. 201580076979.3, mailed Feb. 22, 2021.
Partial Supplementary Search Report for European Application No. 18876258.7, completed Sep. 9, 2021.
Ahrberg, Christian D. et al. "Polymerase chain reaction in microfluidic devices,"© The Royal Society of Chemistry 2016, Lab Chip, 16, pp. 3866-3884, 20 pgs.
Bartlett, John G. "Diagnostic Tests for Agents of Community-Acquired Pneumonia," Clinical Infectious Diseases 2011;52 (Suppl 4) pp. S296-S304.
BioFire Online Demo FilmArray. Http://filmarray.com/the-evidence/online-demo. 2014. 6 pages.
Brunklaus, S. et al., Fast nucleic acid amplification for integration in point-of-care applications, Electrophoresis, 2012, vol. 33, pp. 3222-3228.
Choi, Gihoon et al., "A field-deployable mobile molecular diagnostic system for malaria at the point of need," Lab on a Chip, Royal Society of Chemistry, 2016, 16, 4341-4349.

(56) References Cited

OTHER PUBLICATIONS

Dutta, Gorachand et al. "Microfluidic Devices for Label-Free DNA Detection," Chemosensors, Sep. 25, 2018, 6, 43 www.mdpi.com/journal/chemosensors, 20 pgs.
Gehring et al. "A High-Throughput, Precipitating Colorimetric Sandwich ELISA Microarray for Shiga Toxins," J. Toxins, vol. 6, p. 1855-72, Jun. 11, 2014.
Harding-Esch et al. "A 30-min nucleic acid amplification point-of-care test for genital *Chlamidya trachomatis* infection in women: a prospective, multi-center study of diagnostic accuracy." EBioMedicine 2018; 28:120-27.
Huang et al., "Efficient SNP Discovery by Combining Microarray and Lab-on-a-Chip Data for Animal Breeding and Selection," Microarrays, Nov. 16, 2015, vol. 4, No. 4, pp. 570-595, entire document.
Hwang et al., "Black Printed Circuit Board-based Micro-Polymerase Chain Reaction Chip Structure for Fluorescence Detection Test", International Journal of Control and Automation (2015); vol. 8, No. 10: pp. 15-24 (10 pages).
Interbiotech, "Enzymatic substrates for ImmunoAssays," [retreived from the Internet Nov. 18, 2017: <http://www.interchim.fr/ft/B/BA357a.pdf>], 10 pages.
Kim, Yong Tae et al. "Integrated Microdevice of reverse transcription-polymerase chain reaction with colorimetric immunochromatographic detection for rapid gene expression analysis of influenza A H1N1 virus," Biosensors and Bioelectronics, Elsevier Science Ltd UK, Amsterdam, NL V. 33 No. 1, pp. 88-94, Dec. 14, 2011.
Kim, Jungkyu et al. "Automated microfluidic DNA/RNA extraction with both disposable and reusable components," Journal of Micromechanics and Microengineering, Vo. 22, No. 1, Dec. 20, 2011.
Kopp et al., "Chemical Amplification: Continuous-Flow PCR on a Chip", Science (1998); 280 (5366): 1046-1048.
Lee et al. "A polymer lab-on-a-chip for reverse transcription (RT)-PCR based point-of-care clinical diagnostics," The Royal Society of Chemistry, vol. 8, pp. 2121-2127, Oct. 31, 2008.
Lee et al. "Single-channel multiplexing without melting curve analysis in real-time PCR," Scientific Reports, Dec. 11, 2014, vol. 4, Art. No. 7439, pp. 1-6, entire document.
Mohammed et al., Modeling of Serpentine Continuous Flow Polymerase Chain Reaction Microfluidics, IJEST, vol. 4, No. 3, pp. 1183-1189, Mar. 2012.
Petralia, Salvatore et al. "PCR Technologies for Point of Care Testing: Progress and Perspectives," ACS Sensors, 2017, 2 (7), pp. 876-891, Jul. 6, 2017.
Poritz, Mark A. et al., "FilmArray, an Automated Nested Multiplex PCR System for Multi-Pathogen Detection: Development and Application to Respiratory Tract Infection," PLoS ONE www.plosone.org, Oct. 2011, vol. 6, Issue 10 (14 pgs.).
Roskos, Kristina et al. "Simple System for Isothermal DNA Amplification Coupled to Lateral Flow Detection," PLoS ONE 8(7): e69355. https://doi.org/10.1371/journal.pone.0069355; Jul. 26, 2013, 11 pages.
Schwerdt. Application of ferrofluid as a valve/pump for polycarbonate microfluidic devices. Johns Hopkins University. NSF Summer Undergraduate Fellowship in Sensor Technologies 2006, 17 pages.
Shafagati, et al., The Use of NanoTrap Particles as a Sample Enrichment Method to Enhance the Detection of Rift Valley Fever Virus. PLOS Neglected Tropical Diseases, Jul. 4, 2013; 7(7): e2296.
Suehiro, Noriko et al. "A simplified method for obtaining plant viral RNA for RT-PCR," Journal of Virological Methods 125 (2005) pp. 67-73.
Tanriverdi et al. A rapid and automated sample-to-result HIV load test for near-patient application. J Infect Dis., 201 Suppl 1:S52-S58, 2010.
Thiha et al. A Colorimetric Enzyme-Linked Immunoabsorbent Assay (ELISA) Detection Platform for a Point-Of-Care Dengue Detection System on a Lab-on-Compact-Disc; Sensors ISSN 1424-8220, May 18, 2015.
White, Adam K. et al. High-throughput microfluidic single-cell RT-qPCR, PNAS, Aug. 23, 2011, vol. 108, No. 34, p. 13999-14004.
White, Adam K. et al. "High-throughput microfluidic single-cell RT-qPCR, Supporting Information White et al. 10.1073/pnas. 1019446108" PNAS, Aug. 23, 2011, vol. 108, No. 34, pp. 1-9.
Wu, Jinbo et al. "Extraction, amplification and detection of DNA in microfluidic chip-based assays," © Springer-Verlag Wein 2013, pp. 1611-1631.
Zhang, Chunsun et al. "Survey and Summary—Miniaturized PCR chips for nucleic acid amplification and analysis: latest advances and future trends," Nucleic Acids Research, 2007, vol. 35, No. 13, pp. 4223-4237.
Zhang, Chunsun et al. "PCR microfluidic devices for DNA amplification," Biotechnology Advances 24, (2006) pp. 243-284.
Zumla, Alimuddin et al., "Emerging respiratory tract infections 4—Rapid point of care diagnostic tests for viral and bacterial respiratory tract infections—needs, advances, and future prospects," Lancet Infect. Dis. www.thelancet/infection, vol. 14, Nov. 2014, pp. 1123-1135.
Herbst De Cortina, S. et al. "A Systematic Review of Point of Care Testing for Chlamydia trachomatis, Neisseria gonorrhoeae, and Trichomonas vaginalis," Infectious Diseases in Obstetrics and Gynecology, vol. 2016, 17 pages (Mar. 7, 2016).
Huppert, J. et al. "What's the Point? How Point-of-Care STI Tests can Impact Infected Patients," National Institutes of Health, vol. 9(1): pp. 36-46 (Mar. 1, 2010).
Wheeler, E.K., 'Under-three minute PCR: Probing the limits of fast amplification', published Jul. 27, 2011 by the Royal Society of Chemistry: Analyst 2011 vol. 136 pp. 3707-3712.
Moschou D., et al., 'All-plastic, low-power, disposable, continuous-flow PCR chip with integrated microheaters for rapid DNA amplification', Sensors and Actuators B: Chemical, vol. 199, Aug. 1, 2014, pp. 470-478.
Office Action for Chinese Application No. 201880072796.8, mailed Jun. 1, 2023 with English Translation.
He Qi-di et al., "Advance in Research of Microfluidic Polymerase Chain Reaction Chip", Chinese Journal of Analytical Chemistry, (2016) vol. 44 No. 4, pp. 542~550, English translation of abstract p. 550.
Office Action for U.S. Appl. No. 16/234,453, mailed Sep. 23, 2021.
Benett, William et al. "Handheld advanced nucleic acid analyzer," Event: Environmental and Industrial Sensing, Boston, MA, Proceedings of SPIE, vol. 4200 (2000), pp. 55-63.
Elnifro, Elfath M. et al. "Multiplex PCR: Optimization and Application in Diagnostic Virology," Clinical Microbiology Reviews, vol. 13, No. 4, Oct. 2000, pp. 559-570.
Hassibi et al. "An array-based melt curve analysis method for the identification and classification of closely related pathogen strains." Biology Methods and Protocols 2018; pp. 1-12.
Kim, Young Ho et al., "Performance evaluation of thermal cyclers for PCR in a rapid cycling condition," BioTechniques, www.biotechniques.com, vol. 44, No. 4, 2008, pp. 495-505.
Primiceri, Elisabetta et al. "Key Enabling Technologies for Point-of-Care Diagnostics," MDPI, Sensors 18, 3607; doi:10.3390/s18113607, www.mdpi.com/journal/sensors, 2018, pp. 1-34.
Richards, James et al. "Miniaturized detection system for handheld PCR assays," Event: Environmental and Industrial Sensing, Boston, MA, Proceedings of SPIE, vol. 4200 (2000), pp. 64-73.
Tsaloglou, Maria-Nefeli et al. "Handheld isothermal amplification and electrochemical detection of DNA in resource-limited settings," Analytical Biochemistry 543, 2018, pp. 116-121.
Ullerich, Lars et al. "Ultra-fast PCR technologies for point-of-care testing," De Gruyter, J. Lab Med 2017; 41(5), pp. 239-244.
Yotoriyama, T. et al. "Miniaturized PCR Device for Rapid Detection of Infectious Agents," 14th International Conference on Miniaturized Systems for Chemistry and Life Sciences, Oct. 3-17, 2010, pp. 142-144.
Office Action for Japanese Application No. 2020-518677, mailed Sep. 28, 2022.

(56) References Cited

OTHER PUBLICATIONS

Du, Wenbin et al. "SlipChip," NIH-PA Author Manuscript, NIH Public Access, Author Manuscript, published in final edited form as Lap Chip, PMC, Aug. 21, 2009, 14 pgs.
Office Action for U.S. Appl. No. 16/186,067, mailed Feb. 11, 2021.

* cited by examiner

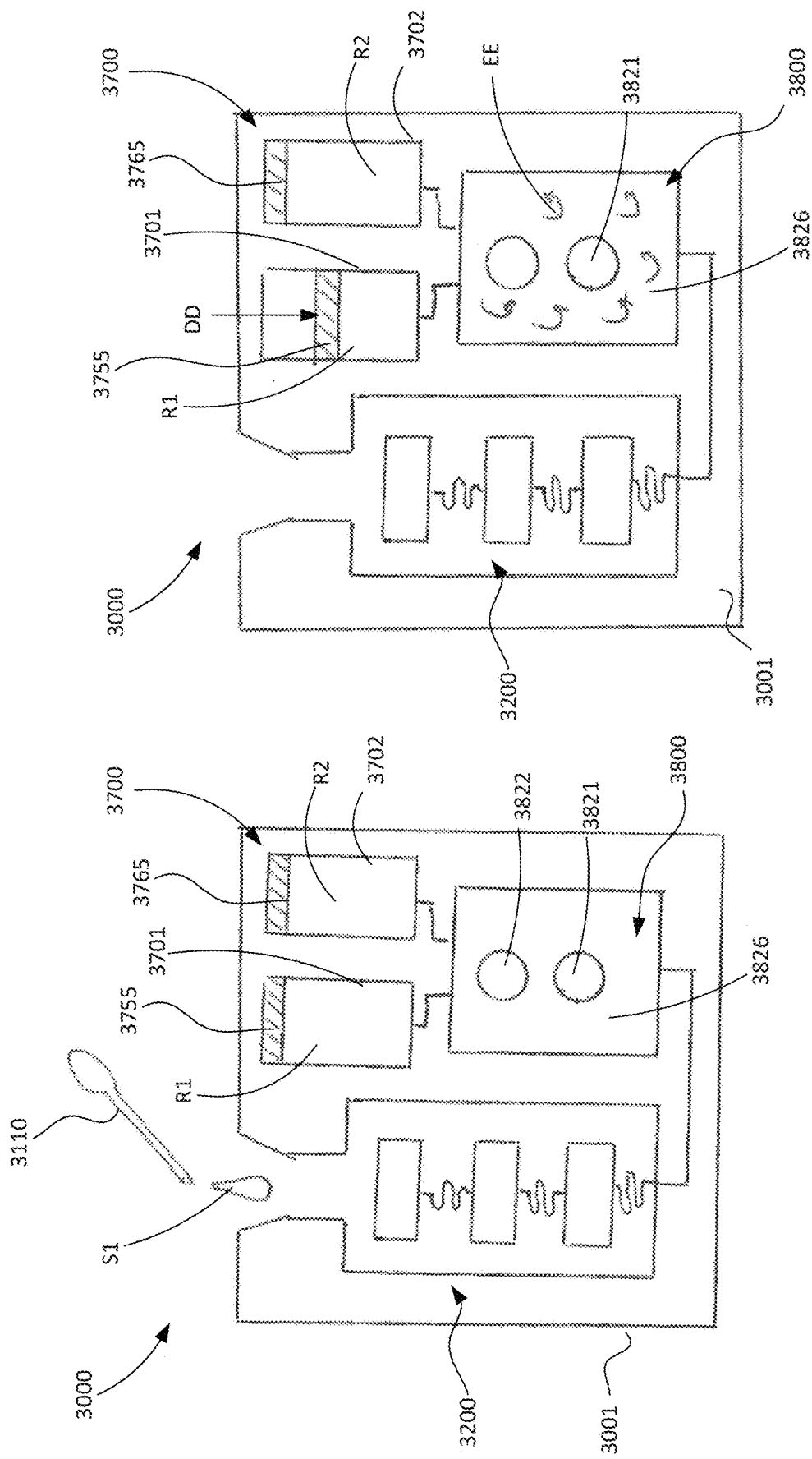

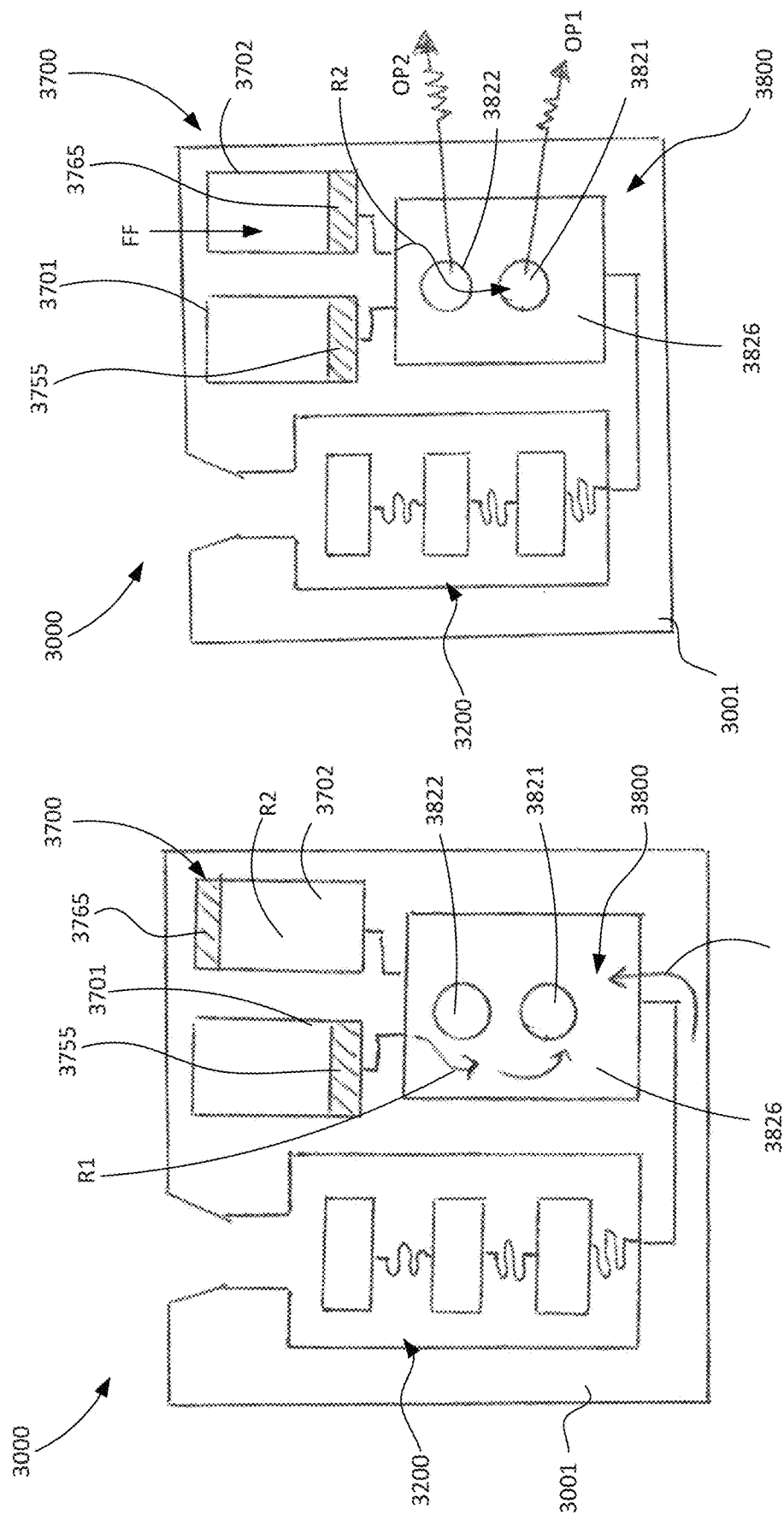

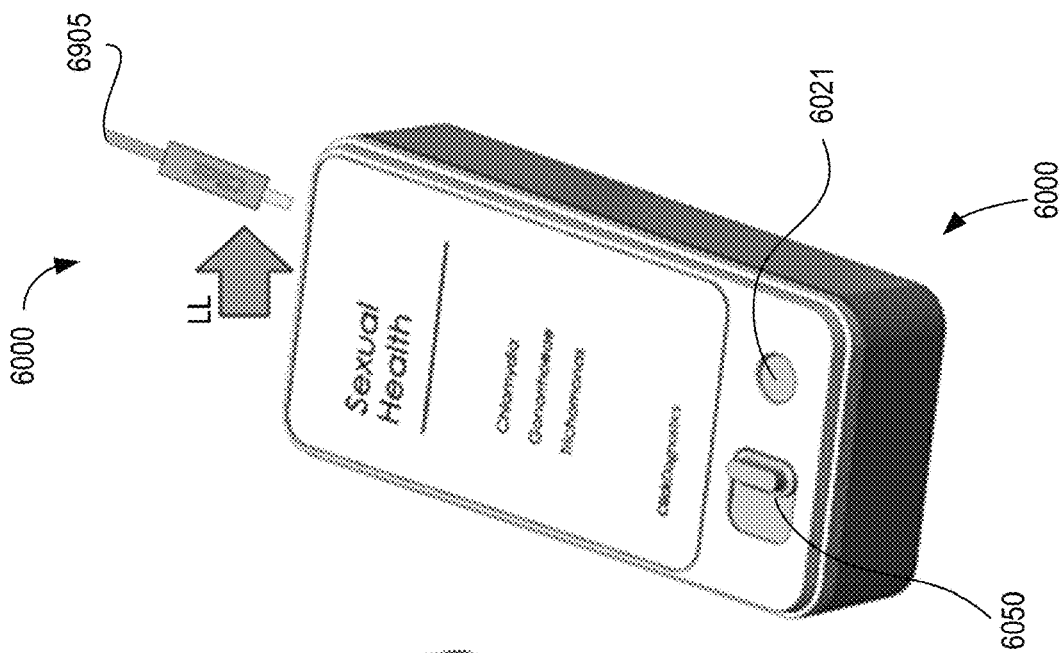
FIG. 53C
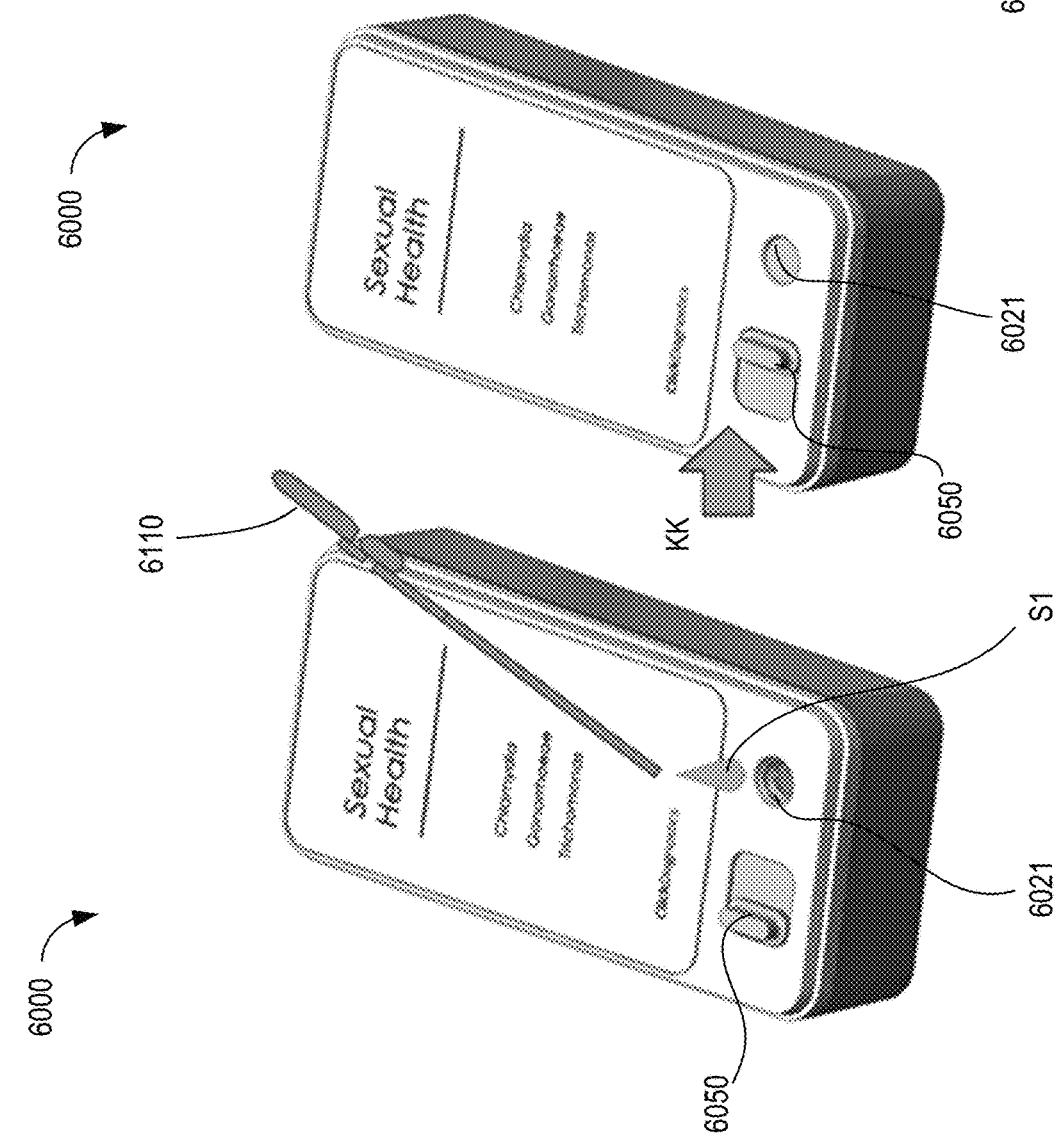
FIG. 53B
FIG. 53A

PORTABLE MOLECULAR DIAGNOSTIC DEVICE AND METHODS FOR THE DETECTION OF TARGET VIRUSES

CROSS-REFERENCE TO RELATED APPLICATIONS

This application is a divisional of U.S. application Ser. No. 16/186,067, now U.S. Pat. No. 11,162,130, entitled "Portable Molecular Diagnostic Device and Methods for the Detection of Target Viruses," filed Nov. 9, 2018, which claims benefit of priority to U.S. Provisional Application Ser. No. 62/583,789, entitled "Portable Molecular Diagnostic Test Device with Reverse Transcription Module," filed Nov. 9, 2017, and 62/594,905, entitled "Portable Molecular Diagnostic Test Device and Methods for the Detection of Target Viruses," filed Dec. 5, 2017, each of which is incorporated herein by reference in its entirety.

SEQUENCE LISTING

The instant application contains a Sequence Listing which has been filed electronically in ASCII format and is hereby incorporated by reference in its entirety. Said ASCII copy, created on Jan. 31, 2019, is named 1001-009-02US_SL.txt and is 1,487 bytes in size.

BACKGROUND

The embodiments described herein relate to devices and methods for molecular diagnostic testing. More particularly, the embodiments described herein relate to disposable, self-contained devices and methods for molecular diagnostic testing that include reverse transcription capabilities.

There are over one billion infections in the U.S. each year, many of which are treated incorrectly due to inaccurate or delayed diagnostic results. Many known point of care (POC) tests have poor sensitivity (30-70%), while the more highly sensitive tests, such as those involving the specific detection of nucleic acids or molecular testing associated with a pathogenic target, are only available in laboratories. Thus, molecular diagnostics testing is often practiced in centralized laboratories. Known devices and methods for conducting laboratory-based molecular diagnostics testing, however, require trained personnel, regulated infrastructure, and expensive, high throughput instrumentation. Known high throughput laboratory equipment generally processes many (96 to 384 and more) samples at a time, therefore central lab testing is often done in batches. Known methods for processing test samples typically include processing all samples collected during a time period (e.g., a day) in one large run, resulting in a turn-around time of many hours to days after the sample is collected. Moreover, such known instrumentation and methods are designed to perform certain operations under the guidance of a skilled technician who adds reagents, oversees processing, and moves sample from step to step. Thus, although known laboratory tests and methods are very accurate, they often take considerable time, and are very expensive.

Although some known laboratory-based molecular diagnostics test methods and equipment offer flexibility (e.g., the ability to test for multiple different indications), such methods and equipment are not easily adaptable for point of care ("POC") use or in-home use by an untrained user. Specifically, such known devices and methods are complicated to use and include expensive and sophisticated components. Thus, the use of such known laboratory-based methods and devices in a decentralized setting (e.g., POC or in-home use) would likely result in an increase in misuse, leading to inaccurate results or safety concerns. For example, many known laboratory-based systems include sophisticated optics and laser light sources, which can present a safety hazard to an untrained user. Some known systems can also require the user to handle or be exposed to reagents, which can be a safety risk for an untrained user. For example, some known systems use relatively large amounts of reagents and/or require replenishment of the reagents (e.g., within an instrument). In addition to being unsuitable for decentralized use, these known systems are also not suitable for long-term storage and shipping. Long-term storage can be desirable, for example to allow for stockpiling of assays for military applications, as a part of the CDC strategic national stockpile program, or other emergency preparedness initiatives.

Moreover, because of the flexibility offered by many known laboratory-based systems, such systems do not include lock-outs or mechanisms that prevent an untrained user from completing certain actions out of the proper sequence. For example, many known systems and methods include several distinct sample preparation operations, such as filtering, washing, lysing, and addition of sample preparation reagents to preserve the target nucleic acids. If such operations are not performed in a predetermined order and/or within predetermined time limits, the accuracy of the test can be compromised. Some known systems attempt to limit the complexities associated with sample preparation by limiting the analysis to only "clean" samples. As a result, such systems do not enable true end-to-end molecular diagnostic methods, because the detailed sample preparation must still be performed by an upstream process.

Although recent advances in technology have enabled the development of "lab on a chip" devices, such devices are often not optimized for point-of-care testing or in-home use. For example, some known devices and methods require an expensive or complicated instrument to interface with the test cartridge, thus increasing the likelihood of misuse. Additionally, many known "lab on a chip" devices amplify a very small volume of sample (e.g., less than one microliter), and are therefore not suited for analyzing for multiple different indications (e.g., a 3-plex or 4-plex test). Moreover, devices that produce such small sample volumes often include optical detection using photocells, charge coupled devices (CCD cameras) or the like, because the sample volumes are too small to produce an output that can be read by the naked eye or less sophisticated (and costly) detectors.

Some known molecular diagnostic systems and methods facilitate detection of viral pathogens by performing reverse transcription polymerase chain reaction (RT-PCR). Although such methods are useful isolating and detecting viruses, they can be complex, thus rendering many know systems and methods unsuitable for decentralized and/or point-of-care use. For example, some known RT-PCR methods include additional steps to isolate and protect the target RNA from rapid degradation from ribonuclease (RNase). Inconsistencies when performing such methods can lead to inaccurate results due to variation in the RNA degradation. Thus, known RT-PCR devices and methods not suitable for use by untrained users.

Some known methods for detecting viruses, such as HIV, include detecting antibodies produced by the body in response to the infection. Such antibody-based tests can be ineffective in identifying persons with acute and early stage HIV infection because such tests are negative for several weeks after the initial infection during the seronegative window. Moreover, although many known diagnostic tests are performed a single time to determine an initial diagnosis, some treatment regimens include repeated testing to evaluate the response of the treatment regimen. For example, many people diagnosed with HIV are undergoing antiretroviral (ARV) therapy. Although in many instances the ARV regimens reduce HIV viral load in blood to undetectable levels, some patients will experience a rebound in the viral load levels due to issues with adherence, development of drug resistance, and toxicities. Accordingly, the ARV regimen also includes repeated viral load testing.

Thus, a need exists for improved devices and methods for molecular diagnostic testing. In particular, a need exists for improved devices and methods that are suitable for long-term storage. A need also exists for improved devices and methods that are easy to use and that can be performed with minimal user input. A need also exists for improved devices and methods that can receive a wide range of samples (e.g., raw samples, such as urine, saliva, and blood). A need also exists for improved devices and methods that include a reverse transcription module or that otherwise allows for detection of a target RNA.

SUMMARY

Molecular diagnostic test devices for amplifying a nucleic acid within a sample and producing an indicator of a target molecule (e.g., DNA or RNA) in the sample are described herein. In some embodiments, a method of detecting a target molecule includes "one-step" or "single button" actuation of a device. For example, in some embodiments, a method includes coupling the molecular diagnostic test device to a power source. A biological sample is conveyed into a sample preparation module within the molecular diagnostic test device via an input opening. The molecular diagnostic test device is then actuated by only a single action to cause the molecular diagnostic test device to perform the following functions without further user action. First, the device heats the biological sample via a heater of the sample preparation module to lyse a portion of the biological sample to produce an input sample. Second, the device conveys the input sample to an amplification module within the molecular diagnostic test device. The device then heats the input sample within a reaction volume of the amplification module to amplify the nucleic acid molecule within the input sample thereby producing an output solution containing a target amplicon. The device then reacts, within a detection module of the molecular diagnostic test device, each of (i) the output solution and (ii) a reagent formulated to produce a signal that indicates a presence of the target amplicon within the output solution. The detection module includes a detection surface configured to capture the target amplicon to produce the signal. A result associated with the signal is then read.

In some embodiments, a molecular diagnostic test device and associated methods involve using a multi-purpose reagent (also referred to as a buffer) to perform both surface blocking and washing functions. In this manner, the quantity of reagents and the simplicity of the device can be improved, thereby facilitating point-of-care use, disposability of the device, and/or operation of the device in accordance with methods that are CLIA waived. Specifically, in some embodiments a multi-purpose reagent can include a blocking agent to reduce the background signals associated with adherence undesirable particles during a detection event. By improving signal quality, such devices and methods can be adaptable for use with limited sample preparation. In addition, the multi-purpose reagent can include a wash agent that removes an unbound constituent from within a detection module. Such methods can include delivering amounts of the multi-purpose reagent at different times in accordance with the desired function of the reagent.

For example, in some embodiments, a method of detecting a nucleic acid using a molecular diagnostic test device, includes conveying at a first time a first volume of a first reagent solution from a reagent module within the molecular diagnostic test device to a detection module within the molecular diagnostic test device. The detection module includes a detection surface configured to capture a target amplicon associated with the nucleic acid. The first reagent solution includes a blocking agent and a wash buffer. The first volume of the first reagent solution contains an amount of the blocking solution sufficient to adsorb to a surface within the detection module. A sample solution containing the target amplicon is conveyed at a second time into the detection module such that the target amplicon is captured on the detection surface. After the second time, a second reagent solution is conveyed into the detection module. The second reagent solution is formulated to cause a signal that indicates a presence of the target amplicon within the sample solution to be produced. The method further includes conveying, after the second time, a second volume of the first reagent solution into the detection module. The second volume of the first reagent solution contains an amount of the wash buffer sufficient to remove an unbound constituent from at least one of the sample solution or the second reagent solution from the detection module.

In some embodiments, a method includes lysing a raw sample and performing a reverse transcription polymerase chain reaction (PCR) on the lysed sample in the same environment. Said another way, in some embodiments, a device includes a single lysing/RT-PCR module to facilitate methods that include lysing a raw sample and performing a fast RT-PCR in a single chamber. Such methods can be performed in a manner that limits the degradation of the target RNA after lysing, thereby producing an accurate result. Accordingly, such methods are suitable for being performed by point-of-care device that is CLIA waived.

For example, in some embodiments, a method of detecting a nucleic acid includes mixing, within a sample preparation module, a reverse transcriptase with a biological sample to form a reverse transcription solution. The reverse transcription solution is heated within the sample preparation module to a first temperature within a lysing temperature range to release a ribonucleic acid (RNA) molecule. The reverse transcription solution is heated, within the same sample preparation module, to a second temperature within a reverse transcription temperature range to produce a complementary deoxyribonucleic acid (cDNA) molecule. The reverse transcription solution is then heated, within the same sample preparation module, to a third temperature above an inactivation temperature to cause inactivation of the reverse transcriptase. The method further includes conveying the reverse transcription solution to an amplification module, in which the cDNA can be amplified for later detection.

in some embodiments, a method of detecting a target RNA molecule using a disposable molecular diagnostic test device includes conveying an input sample to a reverse transcription module within a housing of the disposable molecular diagnostic test device. The input sample is heated within the reverse transcription module to produce a target cDNA molecule associated with the target RNA molecule. The input sample is conveyed from the reverse transcription module to an amplification module within the housing. The amplification module defines a reaction volume and including a heater. The method further includes heating the input sample within at least a portion of the reaction volume via the heater to amplify the target cDNA molecule within the input sample thereby producing an output solution containing a target amplicon. The method further includes conveying into a detection module each of A) the output solution and B) a reagent formulated to produce a signal that indicates a presence of the target amplicon within the output solution, the detection module including a detection surface configured to retain the target amplicon to produce the signal. The disposable molecular diagnostic test device producing the signal when a viral load of the input sample is greater than 10 copies per milliliter.

BRIEF DESCRIPTION OF THE DRAWINGS

FIGS. 8-11 are schematic illustrations of a molecular diagnostic test device that uses a multi-purpose reagent, according to an embodiment, in a first configuration, a second configuration, a third configuration, and a fourth configuration, respectively.

FIGS. 53A-53C are perspective views of the molecular diagnostic device shown in FIGS. 20 and 21 in various stages of operation, according to an embodiment.

DETAILED DESCRIPTION

Figure 1:
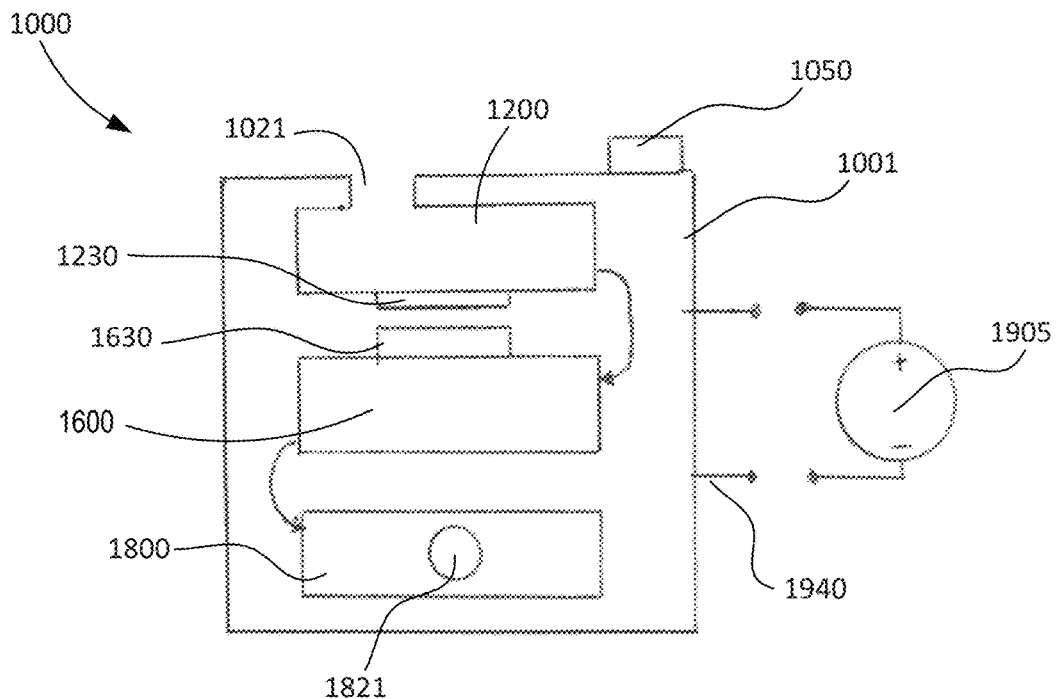
FIGS. 1-3 are schematic illustrations of a molecular diagnostic test device, according to an embodiment, in a first configuration, a second configuration, and a third configuration, respectively.

In some embodiments, an apparatus is configured for a disposable, portable, single-use, inexpensive, molecular diagnostic approach. The apparatus can include one or more modules configured to perform high quality molecular diagnostic tests, including, but not limited to, sample preparation, nucleic acid amplification (e.g., via polymerase chain reaction, isothermal amplification, or the like), and detection. In some embodiments, sample preparation can be performed by isolating the target pathogen/entity and removing unwanted amplification (e.g., PCR) inhibitors. The target entity can be subsequently lysed to release target nucleic acid for amplification. A target nucleic acid in the target entity can be amplified with a polymerase undergoing temperature cycling or via an isothermal incubation to yield a greater number of copies of the target nucleic acid sequence for detection.

In some embodiments, the devices described herein are stand-alone devices that include all necessary substances, mechanisms, and subassemblies to perform any of the molecular diagnostic tests described herein. Such stand-alone devices do not require any external instrument to manipulate the biological samples, and only require connection to a power source (e.g., a connection to an A/C power source, coupling to a battery, or the like) to complete the methods described herein. For example, the device described herein do not require any external instrument to heat the sample, agitate or mix the sample, to pump (or move) fluids within a flow member, or the like. Rather, the embodiments described herein are fully-contained and upon add a biological sample and being coupled to a power source, the device can be actuated to perform the molecular diagnostic tests described herein. In some embodiments, the method of actuating the device can be such that the device is a CLIA-waived device and/or can operate in accordance with methods that are CLIA waived.

In some embodiments, a method of detecting a target molecule includes "one-step" or "single button" actuation of a device. For example, in some embodiments, a method includes coupling the molecular diagnostic test device to a power source. A biological sample is conveyed into a sample preparation module within the molecular diagnostic test device via an input opening. The molecular diagnostic test device is then actuated by only a single action to cause the molecular diagnostic test device to perform the following functions without further user action. First, the device heats the biological sample via a heater of the sample preparation module to lyse a portion of the biological sample to produce an input sample. Second, the device conveys the input sample to an amplification module within the molecular diagnostic test device. The device then heats the input sample within a reaction volume of the amplification module to amplify the nucleic acid within the input sample thereby producing an output solution containing a target amplicon. The device then reacts, within a detection module of the molecular diagnostic test device, each of (i) the output solution and (ii) a reagent formulated to produce a signal that indicates a presence of the target amplicon within the output solution. The detection module includes a detection surface configured to capture the target amplicon to produce the signal. A result associated with the signal is then read.

In some embodiments, an apparatus can include a lid (also referred to as a cover) that functions both to cover an input sample port and also actuate one or more mechanisms of the device when the lid is closed. In this manner, the single act of closing the lid also actuates all aspects of the device, thus simplifying the device actuation and method. In particular, in some embodiments, a method of detecting a nucleic acid includes coupling the molecular diagnostic test device to a power source and conveying a biological sample into a sample preparation module within the molecular diagnostic test device via an input opening. The order of these operations does not matter. To actuate the device, the input opening is covered with a lid coupled to the molecular diagnostic test device. In response to only the covering, the device then performs the following functions without further user action. First, the device heats the biological sample via a heater of the sample preparation module to lyse a portion of the biological sample to produce an input sample. Second, the device conveys the input sample to an amplification module within the molecular diagnostic test device. The device then heats the input sample within a reaction volume of the amplification module to amplify the nucleic acid within the input sample thereby producing an output solution containing a target amplicon. The device then reacts, within a detection module of the molecular diagnostic test device, each of (i) the output solution and (ii) a reagent formulated to produce a signal that indicates a presence of the target amplicon within the output solution. The detection module includes a detection surface configured to capture the target amplicon to produce the signal. A result associated with the signal is then read.

In some embodiments, an apparatus includes a housing, a sample preparation module within the housing, a reagent module within the housing, a detection module, and a lid movably coupled to the housing. The sample preparation module defines a sample input volume that receives a biological sample and an input opening through which the sample input volume can be accessed. The sample preparation module includes a heater configured to heat the biological sample to produce an input solution. The reagent module includes a reagent container containing a detection reagent formulated to facilitate production of a signal that indicates a presence of a target amplicon from the input solution. The detection reagent is sealed within the reagent container. The seal can be, for example, a foil seal that preserves the shelf life of the reagent and prevents leakage of the reagent. The detection module includes a detection surface configured to capture the target amplicon from the input solution. The detection module is in fluid communication with the reagent module such that the signal is produced in response to the reagent being conveyed into the detection module. The lid includes a seal portion, a switch portion, and reagent actuator. The lid moves relative to the housing between a first lid position and a second lid position. The input opening is exposed when the lid is in the first lid position and the seal portion of the lid covers the input opening when the lid is in the second lid position. When the lid is moved from the first lid position to the second lid position: A) the switch portion actuates a switch to provide power to the heater, and B) the reagent actuator causes the reagent to be released from the sealed reagent container.

In some embodiments, the apparatus further includes an amplification module within the housing that receives the input solution from the sample preparation module. The amplification module is configured to heat the input solution to amplify a nucleic acid within the input solution to produce a detection solution containing the target amplicon.

In some embodiments, the lid includes a lock portion that irreversibly engages at least one of the housing, the sample preparation module, or the reagent module to maintain the lid in the second lid position. In this manner, the molecular diagnostic device is configured to be irreversibly used. Similarly stated, this arrangement prevents re-use of the device or subsequent attempts to supplement the biological sample after the device has been actuated.

In some embodiments, the reagent module includes a reagent housing and a puncturer. The reagent housing defines a reagent reservoir into which the reagent is released from the sealed reagent container when the puncturer pierces a portion of the reagent container. The reagent actuator includes a protrusion that exerts a force to cause the puncturer to pierce the portion of the reagent container when the lid is moved from the first lid position to the second lid position. In some embodiments, the apparatus includes a deformable support member that is configured to maintain the puncturer and/or the reagent container in a position in which they are spaced apart. The deformable support member is configured to deform to move the puncturer and/or the reagent container into contact with each other in response to a force exerted when the lid is moved to the second position.

In some embodiments, an apparatus includes a housing of a molecular diagnostic device and a reagent module within the housing. The reagent module includes a reagent housing, a reagent container containing a reagent sealed therein, a puncturer, and a deformable support member. The reagent housing defines a reagent reservoir into which the reagent is released from the reagent container when the puncturer pierces a portion of the reagent container. The deformable support member includes a sealing portion and coupling portion. The sealing portion is coupled to the reagent housing to fluidically isolate the reagent reservoir. The coupling portion is coupled to at least one of the puncturer or the reagent container. The deformable support member is configured to deform from a first configuration to a second configuration in response to an actuation force exerted on the deformable support member. The deformable support member maintains the puncturer spaced apart from the portion of the reagent container when the deformable support member is in the first configuration. The puncturer pierces the portion of the reagent container when the deformable support member is in the second configuration.

In some embodiments, the reagent is one of a first reagent or a second reagent. The first reagent is formulated to be bound to the target molecule in response to the first reagent being conveyed into the detection module and the second reagent is formulated to produce the signal when catalyzed by the first reagent. The second reagent can be, for example a precipitating substrate formulated to produce an insoluble colored particle when the second reagent is contacted with the first reagent.

In some embodiments, the reagent is a first reagent, and is one of a catalyzing reagent formulated to be bound to the target molecule in response to the first reagent being conveyed into the detection module or a precipitating reagent formulated to produce the signal when catalyzed by the catalyzing reagent. The reagent module includes a second reagent container containing a solution including a wash buffer and a blocking buffer, the blocking buffer formulated to reduce adhesion of the target amplicon or other molecules within the detection module. The coupling portion of the deformable support member is coupled to at least one of a second puncturer or the second reagent container. The deformable support member maintains the second puncturer spaced apart from the second reagent container when the deformable support member is in the first configuration. The second puncturer pierces the second reagent container when the deformable support member is in the second configuration.

In some embodiments, a molecular diagnostic test device and associated methods involve using a multi-purpose reagent (also referred to as a buffer) to perform both surface blocking and washing functions. In this manner, the quantity of reagents and the simplicity of the device can be improved, thereby facilitating point-of-care use, disposability of the device, and/or operation of the device in accordance with methods that are CLIA waived. Specifically, in some embodiments a multi-purpose reagent can include a blocking agent to reduce the background signals associated with adherence undesirable particles during a detection event. By improving signal quality, such devices and methods can be adaptable for use with limited sample preparation. In addition, the multi-purpose reagent can include a wash agent that removes an unbound constituent from within a detection module. Such methods can include delivering amounts of the multi-purpose reagent at different times in accordance with the desired function of the reagent.

For example, in some embodiments, a method of detecting a nucleic acid using a molecular diagnostic test device, includes conveying at a first time a first volume of a first reagent solution from a reagent module within the molecular diagnostic test device to a detection module within the molecular diagnostic test device. The detection module includes a detection surface configured to capture a target amplicon associated with the nucleic acid. The first reagent solution includes a blocking agent and a wash buffer. The first volume of the first reagent solution contains an amount of the blocking solution sufficient to adsorb to a surface within the detection module. A sample solution containing the target amplicon is conveyed at a second time into the detection module such that the target amplicon is captured on the detection surface. After the second time, a second reagent solution is conveyed into the detection module. The second reagent solution is formulated to cause a signal that indicates a presence of the target amplicon within the sample solution to be produced. The method further includes conveying, after the second time, a second volume of the first reagent solution into the detection module. The second volume of the first reagent solution contains an amount of the wash buffer sufficient to remove an unbound constituent from at least one of the sample solution or the second reagent solution from the detection module. In some embodiments, the first reagent solution includes between 0.02 percent and 5 percent bovine serum albumin and between 0.05 percent and 10 percent of the detergent.

In some embodiments, a method of detecting a nucleic acid using a molecular diagnostic test device, includes reusing a multi-purpose reagent. Specifically, the reagent can be used a first time to perform blocking functions and then can be conveyed through the detection module at a second time to perform washing functions. This arrangement and method enables less reagent to be contained in the molecular diagnostic test device, thereby facilitating a more efficient, lower cost single-use, stand-alone device. Specifically, in some embodiments, a method of detecting a nucleic acid using a molecular diagnostic test device includes conveying a biological sample into a sample preparation module within the molecular diagnostic test device via an input opening. The device is then actuated to cause the device to perform the following functions. First, the device conveys a first volume of a reagent solution from a reagent module within the molecular diagnostic test device to a detection module that includes a detection surface configured to capture a target amplicon associated with the nucleic acid. The reagent solution includes a blocking agent and a wash buffer, with the blocking agent being formulated to adsorb to a surface within the detection module. The device then conveys the first volume of the reagent solution from the detection module back to the reagent module. An output solution containing the target amplicon associated with the nucleic acid is then produced from the biological sample. This can be performed via any of the sample preparation modules or amplification modules described herein. The output solution is then conveyed into the detection module such that the target amplicon is captured on the detection surface. The device then conveys a second volume of the reagent solution from the reagent module into the detection module to remove an unbound constituent from the output solution from the detection module. A result associated with the target amplicon captured on the detection surface is then read.

In some embodiments, a method includes lysing a raw sample and performing a reverse transcription polymerase chain reaction (PCR) on the lysed sample in the same environment. Said another way, in some embodiments, a device includes a single lysing/RT-PCR module to facilitate methods that include lysing a raw sample and performing a fast RT-PCR in a single chamber. Such methods can be performed in a manner that limits the degradation of the target RNA after lysing, thereby producing an accurate result. Accordingly, such methods are suitable for being performed by point-of-care device that is CLIA waived.

For example, in some embodiments, a method of detecting a nucleic acid includes mixing, within a sample preparation module, a reverse transcriptase with a biological sample to form a reverse transcription solution. The reverse transcription solution is heated within the sample preparation module to a first temperature within a lysing temperature range to release a ribonucleic acid (RNA) molecule. The reverse transcription solution is heated, within the same sample preparation module, to a second temperature within a reverse transcription temperature range to produce a complementary deoxyribonucleic acid (cDNA) molecule. The reverse transcription solution is then heated, within the same sample preparation module, to a third temperature above an inactivation temperature to cause inactivation of the reverse transcriptase. The method further includes conveying the reverse transcription solution to an amplification module, in which the cDNA can be amplified for later detection.

In some embodiments, a method of detecting a nucleic acid includes mixing, within a sample preparation module, a reverse transcriptase with a biological sample to form a reverse transcription solution. The reverse transcription solution is heated within the sample preparation module to a first temperature within a lysing temperature range to release a ribonucleic acid (RNA) molecule. The reverse transcription solution is heated, within the same sample preparation module, to a second temperature within a reverse transcription temperature range to produce a complementary deoxyribonucleic acid (cDNA) molecule. The heating to the first temperature and the heating to the second temperature are performed continuously such that the cDNA is produced within less than 1 minute of when the RNA molecule is released.

in some embodiments, a method of detecting a target RNA molecule using a disposable molecular diagnostic test device includes conveying an input sample to a reverse transcription module within a housing of the disposable molecular diagnostic test device. The input sample is heated within the reverse transcription module to produce a target cDNA molecule associated with the target RNA molecule. The input sample is conveyed from the reverse transcription module to an amplification module within the housing. The amplification module defines a reaction volume and including a heater. The method further includes heating the input sample within at least a portion of the reaction volume via the heater to amplify the target cDNA molecule within the input sample thereby producing an output solution containing a target amplicon. The method further includes conveying into a detection module each of A) the output solution and B) a reagent formulated to produce a signal that indicates a presence of the target amplicon within the output solution, the detection module including a detection surface configured to retain the target amplicon to produce the signal. The disposable molecular diagnostic test device produces the signal when a viral load of the input sample is greater than 1000 copies per milliliter. In other embodiments, the disposable molecular diagnostic test device can produce the signal when the viral load of the input sample is greater than 100 copies per milliliter. In yet other embodiments, the disposable molecular diagnostic test device can produce the signal when the viral load of the input sample is greater than 10 copies per milliliter.

In some embodiments, an apparatus includes a housing, a sample preparation module, a reverse transcription module, and an amplification module, each module being within the housing. The sample preparation module defines an input reservoir configured to receive a blood sample. The sample preparation module is configured to separate a plasma sample from the blood sample, the plasma sample containing a target RNA molecule. The reverse transcription module configured to heat the plasma sample to produce a target cDNA molecule associated with the target RNA molecule thereby producing an amplification solution. The amplification module includes a flow member and a heater. The flow member defines a reaction volume configured to receive the amplification solution. The heater is configured to convey thermal energy into the reaction volume to amplify the target cDNA molecule within the amplification solution to produce an output containing a target amplicon.

In some embodiments, a method of detecting a target RNA molecule using a molecular diagnostic test device includes first conveying a biological sample into a sample preparation module within the disposable molecular diagnostic test device. The device is then actuated to cause the device to perform the following functions. The device heats the biological sample within a reverse transcription portion of the sample preparation module to produce a target cDNA molecule associated with the target RNA molecule, thereby producing an amplification sample. The target cDNA is mixed with a primer composition associated with multiple target sequences of the target cDNA molecule. The amplification sample is then conveyed to an amplification module within the device and is then heated to amplify each of the multiple target sequences of the target cDNA molecule within the amplification sample thereby producing an output solution containing multiple target amplicons. The device then conveys into a detection module each of A) the output solution and B) a reagent formulated to produce a signal that indicates a presence of the target amplicon within the output solution. The detection module that including a detection surface configured to retain the plurality of target amplicons within a single region to produce the signal. The method further includes reading the signal from the detection surface.

As used in this specification and the appended claims, the term "reagent" includes any substance that is used in connection with any of the reactions described herein. For example, a reagent can include an elution buffer, a PCR reagent, an enzyme, a substrate, a wash solution, a blocking solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include nonactive and/or inert constituents such as, water, colorant or the like.

The term "nucleic acid molecule," "nucleic acid," or "polynucleotide" may be used interchangeably herein, and may refer to deoxyribonucleic acid (DNA) or ribonucleic acid (RNA), including known analogs or a combination thereof unless otherwise indicated. Nucleic acid molecules to be profiled herein can be obtained from any source of nucleic acid. The nucleic acid molecule can be single-stranded or double-stranded. In some cases, the nucleic acid molecules are DNA The DNA can be mitochondrial DNA, complementary DNA (cDNA), or genomic DNA. In some cases, the nucleic acid molecules are genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can be derived from one or more of chromosomes 1, 2, 3, 4, 5, 6, 7, 8, 9, 10, 11, 12, 13, 14, 15, 16, 17, 18, 19, 20, 21, 22, X, or Y. In some cases, the nucleic acid molecules are RNA can include, but is not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoR-NAs, microRNAs, siRNAs, piRNAs and long nc RNAs. The source of nucleic acid for use in the devices, methods, and compositions described herein can be a sample comprising the nucleic acid.

Unless indicated otherwise, the terms apparatus, diagnostic apparatus, diagnostic system, diagnostic test, diagnostic test system, test unit, and variants thereof, can be interchangeably used.

The methods described herein can be performed on any suitable molecular diagnostic device, such as any of the diagnostic devices shown and described herein or in International Patent Publication No. WO2016/109691, entitled "Devices and Methods for Molecular Diagnostic Testing," International Patent Publication No. WO2017/185067, entitled "Printed Circuit Board Heater for an Amplification Module," International Patent Publication No. WO2018/005710, entitled "Devices and Methods for Detection of Molecules Using a Flow Cell," and International Patent Publication No. WO2018/005870, entitled "Devices and Methods for Nucleic Acid Extraction," each of which is incorporated herein by reference in its entirety.

Figure 2:
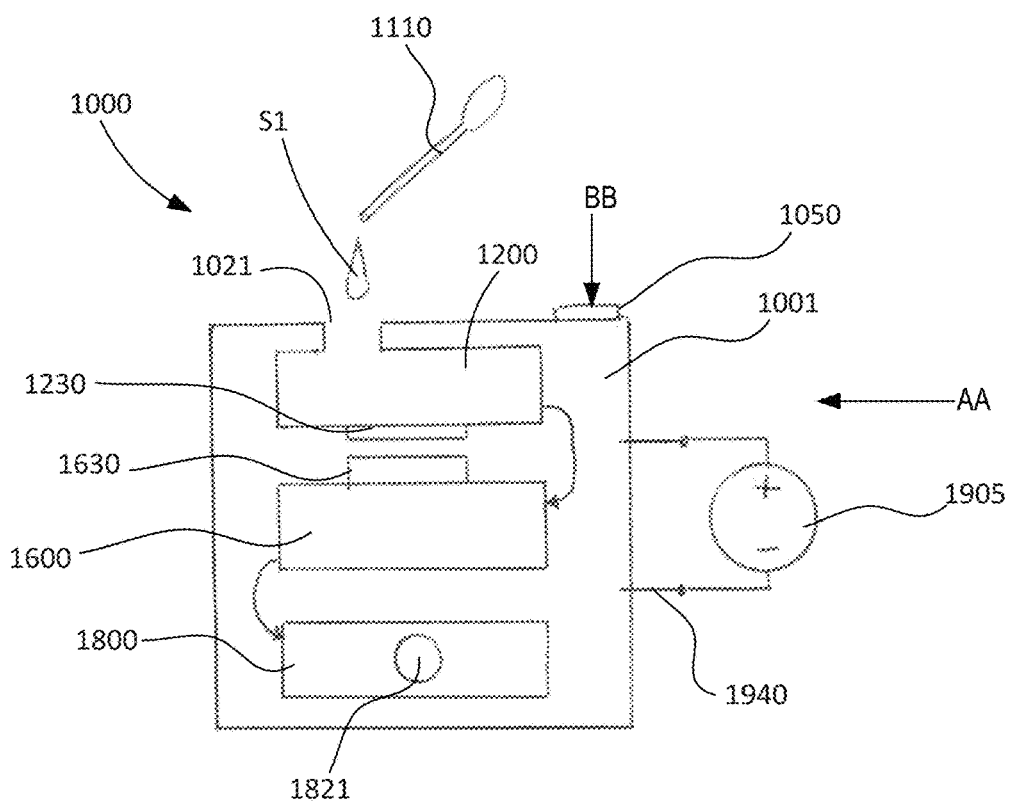
Figure 3:
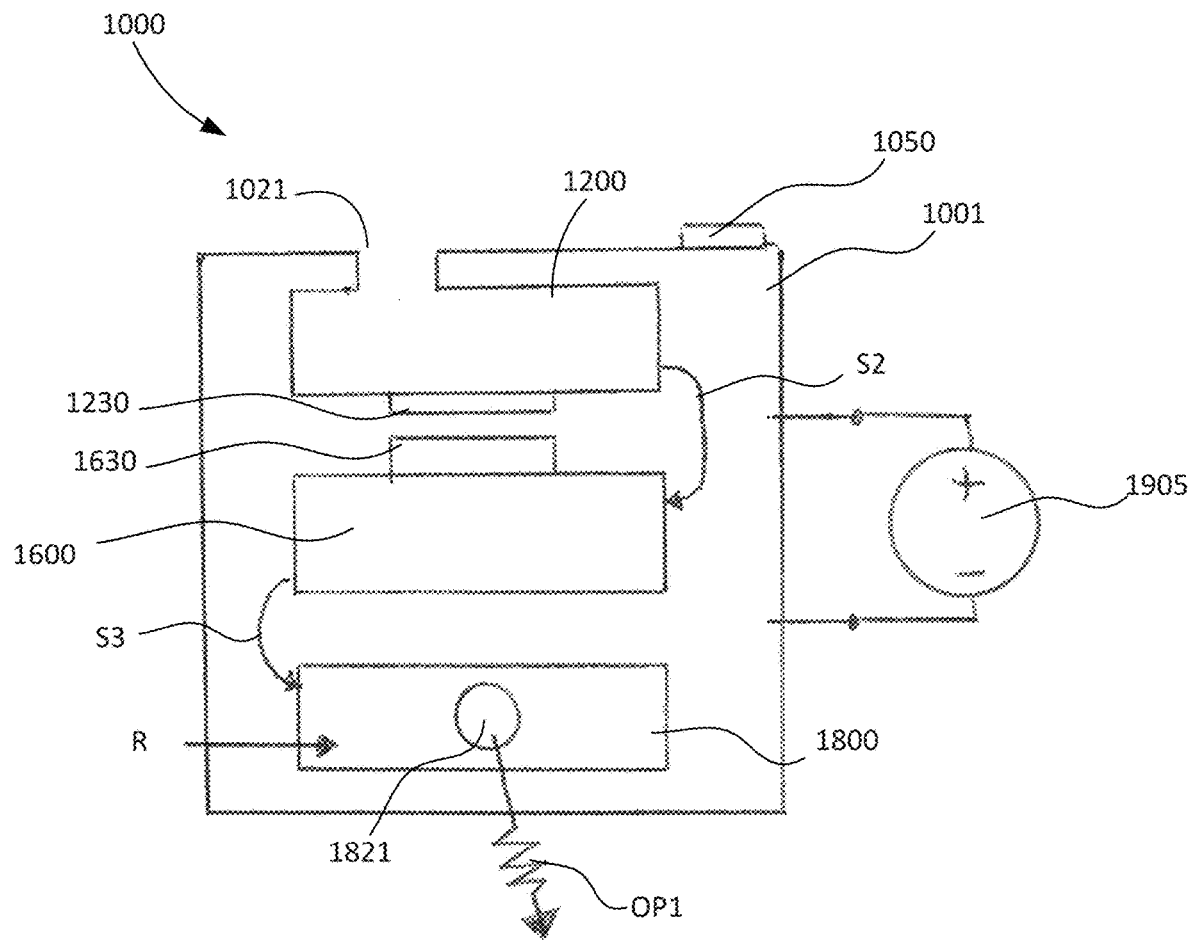

FIGS. 1-3 are schematic illustrations of a molecular diagnostic test device 1000 (also referred to as a "test device" or "device"), according to an embodiment. The test device 1000 is configured to manipulate biological sample to produce one or more output signals associated with a target cell, according to any of the methods described herein. In some embodiments, the test device 1000 can be an integrated device that is suitable for use within a point-of-care setting (e.g., doctor's office, pharmacy or the like), decentralized test facility, or at the user's home. Similarly stated, in some embodiments, the modules of the device, described below, are contained within a single housing such that the test device can be fully operated without any additional instrument, docking station, or the like. Further, in some embodiments, the device 1000 can have a size, shape and/or weight such that the device 1000 can be carried, held, used and/or manipulated in a user's hands (i.e., it can be a "handheld" device). In some embodiments, the test device 1000 can be a self-contained, single-use device.

To facilitate ease of use, in addition inputting the biological sample and connecting the device to a power source, the device 1000 is configured to be actuated by a single step or action. The "single button" actuation reduces the complexity of the operating steps, thereby making the device and methods suitable for use by an untrained user. As described below, the device does not require manipulating multiple different actuators (or buttons) to cause sample preparation, no shaking or external agitation is required, and no complicated "signal reading" steps are required.

In some embodiments, the device 1000 (and any of the devices shown and described herein) can be a CLIA-waived device and/or can operate in accordance with methods that are CLIA waived. Similarly stated, in some embodiments, the device 1000 (and any of the other devices shown and described herein) is configured to be operated in a sufficiently simple manner and can produce results with sufficient accuracy to pose a limited likelihood of misuse and/or to pose a limited risk of harm if used improperly. In some embodiments, the device 1000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 1000 can be configured for long term storage in a manner that poses a limited likelihood of misuse (spoilage of the reagent(s), expiration of the reagents(s), leakage of the reagent(s), or the like). In some embodiments, the molecular diagnostic test device 1000 is configured to be stored for up to about 36 months, up to about 32 months, up to about 26 months, up to about 24 months, up to about 20 months, up to about 18 months, up to 12 months, up to 6 months, or any values there between.

The test device 1000 includes a housing 1001, an actuator 1050, a sample preparation module 1200 (also referred to as a sample staging module), an amplification module 1600, and a detection module 1800. In some embodiments, the test device 1000 can include any other components or modules described herein, such as, for example, a reagent module that contains on-board reagents (e.g., the reagent module 6700), a rotary valve (e.g., to control flow of reagents and/or sample, such as the valve 6300), or a fluid transfer module (e.g., the fluid transfer module 6400). The housing 1001 can be any structure within which the sample preparation module 1200 or other components are contained (or partially contained) to form an integrated device for sample preparation and/or molecular testing. The housing 1001 can be a monolithically constructed housing or can include multiple separately constructed members that are later joined together to form the housing 1001. As shown in FIG. 2, the housing defines an input opening 1021 through which a biological sample S1 can be conveyed into the sample preparation module 1200.

The sample preparation module 1200 includes a heater 1230 and is configured to manipulate the biological sample S1 for further diagnostic testing. For example, in some embodiments, the sample preparation module 1200 can extract nucleic acid molecules from the biological sample S1 and can produce an output solution S2 (see FIG. 3) that is conveyed into the amplification module 1600. The sample preparation module 1200 can include any other components described herein, such as, for example, a heater for lysis, a chamber within which RT-PCR can be performed, and/or an inactivation chamber (see, e.g., the lysing housing 6201).

The amplification module 1600 defines an internal volume (e.g., a reaction chamber or reaction volume) and includes a heater 1630. The reaction volume can be a single volume or a series of volumes within which an input solution S2 (i.e., the solution containing extracted nucleic acid from the biological sample S1) can flow and/or be maintained to amplify the target nucleic acid molecules therein to produce an output detection solution S3 that contains a target amplicon to be detected. In some embodiments, the reaction volume includes a flow path that is curved such that the flow path intersects the heater 1630 at multiple locations. In this manner, the amplification module 1600 can perform a "flow through" amplification reaction where the input solution S2 flows through multiple different temperature regions.

The heater 1630 can be any suitable heater or group of heaters that can heat the input solution S2 to perform any of the amplification operations as described herein. In some embodiments, the heater 1630 can establish multiple temperature zones through which the prepared solution flows and/or can define a desired number of amplification cycles to ensure the desired test sensitivity (e.g., at least 30 cycles, at least 34 cycles, at least 36 cycles, at least 38 cycles, or at least 40 cycles). The heater 1630 (and any of the heaters described herein) can be of any suitable design. For example, in some embodiments, the heater 1630 can be a resistance heater, a thermoelectric device (e.g. a Peltier device), or the like.

In some embodiments, the amplification module 1600 (or any of the amplification modules described herein) can be similar to the amplification modules shown and described in U.S. Patent Publication No. 2017/0304829, entitled "Printed Circuit Board Heater for an Amplification Module," which is incorporated herein by reference in its entirety. In other embodiments, the amplification module 1600 (or any of the amplification modules described herein) can be similar to the amplification modules shown and described in International Patent Publication No. WO2016/109691, entitled "Devices and Methods for Molecular Diagnostic Testing," which is incorporated herein by reference in its entirety. Although the amplification module 1600 is generally described as performing a thermal cycling operation on the input solution S2, in other embodiment, the amplification module 1600 (and any of the amplification modules described herein) can perform any suitable thermal reaction to amplify nucleic acids within the solution. In some embodiments, the amplification module 1600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

The detection module 1800 is configured to react the output solution S3 from the amplification module 1600 with one or more reagents to produce a signal (or output) OP1 to indicate presence or absence of a target organism in the biological sample S1. Specifically, the detection module 1800 defines a detection channel and includes a detection surface 1821 within the detection channel. The detection channel is in (or can be placed in) fluid communication with the amplification module 1600. In this manner, the output solution S3 containing the target amplicon can be conveyed into the detection channel and across the detection surface 1821. Additionally, as shown in FIG. 3, a reagent R formulated to produce, catalyze, or facilitate production of a signal that indicates a presence of the target amplicon can be conveyed into the detection channel and across the detection 1821. The detection surface 1821 includes a series of capture probes to which the target amplicon can be bound when the output solution S3 flows across the detection surface 1821. The capture probes can be any suitable probe of the types described herein formulated to capture or bind to the target amplicon.

Figure 4:
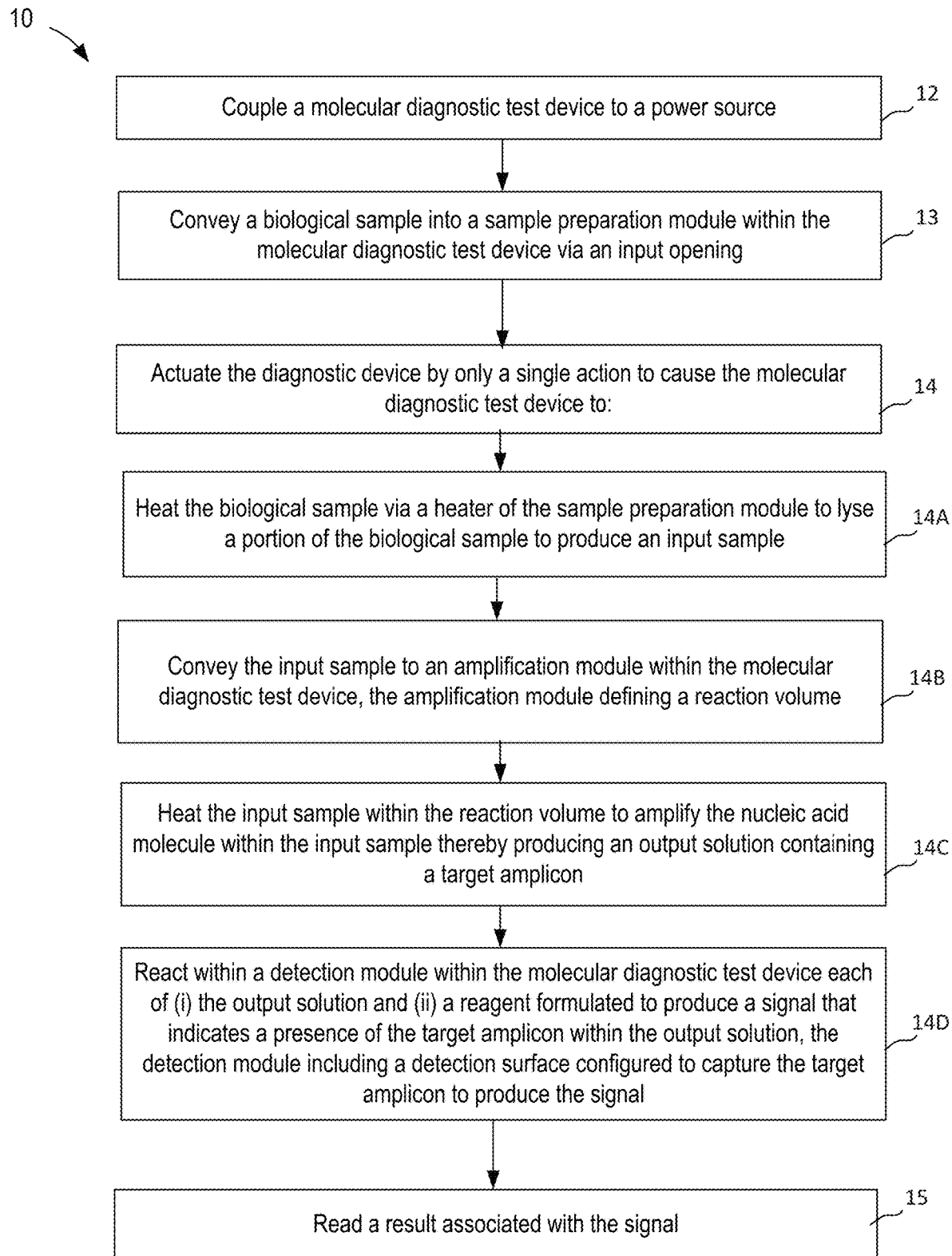
FIG. 4 is a flow chart of a method of detecting a nucleic acid including a single actuation operation, according to an embodiment.

The molecular diagnostic test device 1000 (and any of the molecular diagnostic test devices described herein) can perform any of the "one touch" actuation methods described herein. For example, FIG. 4 is a flow chart of a method 10 of detecting a nucleic acid, according to an embodiment. Although the method 10 is described as being performed on the device 1000, in other embodiments, the method 10 can be performed on any suitable device, such as the device 6000 described below. The method 10 includes coupling the molecular diagnostic test device to a power source, at 12. Referring to FIGS. 1 and 2, the power source 1905 can be coupled to terminals 1940 of the device, as shown by the arrow AA. The power source 1905 can be any suitable power source, such as an alternating current (A/C) power source, a direct current (D/C) power source (e.g., a battery), a fuel cell, or the like. In some embodiments, the power source 1905 can be an A/C power source, and the connecting can include plugging the device into a power outlet using a power cord. In other embodiments, the power source 1905 can be a D/C power source, and the connecting can include coupling a battery to the terminals 1940 of the device. In yet other embodiments, the power source 1905 can be a D/C power source that is resident within the housing of the device, and the coupling can include removing an electrical isolation member from between the power source and the remainder of an electronic controller (not shown in FIGS. 1-3) of the device.

A biological sample is conveyed into a sample preparation module within the molecular diagnostic test device via an input opening, at 13. Referring to FIG. 2, in some embodiments, the biological sample S1 can be conveyed into the device by a sample transfer device 1110. The sample transfer device 1110 can be any suitable device, such as a pipette or other mechanism configured can be used to aspirate or withdraw the sample S1 from a sample cup, container or the like, and then deliver a desired amount of the sample via the opening 1021. The biological sample S1 can be any suitable sample, such as, for example, blood, urine, male urethral specimens, vaginal specimens, cervical swab specimens, nasal swab specimens, throat swab specimens, rectal swab specimens, or any other biological samples described herein. Thus, in some embodiments, the biological sample S1 can be a "raw" (or unprocessed) sample.

The molecular diagnostic test device is then actuated by only a single action, at 14, which causes the molecular diagnostic test device to perform a series of operations without any further user input. Said another way, the molecular diagnostic test device is actuated via only a "single button," as shown by the arrow BB and the actuator 1050 in FIG. 2. Although the actuator 1050 is shown as a push-button style actuator, the "single action" in operation 14 can be performed by any suitable mechanism. For example, in some embodiments, the device can include a slide actuator that actuates the device when the actuator slides relative to the device housing. In other embodiments, the device can include a rotary actuator or an actuator that is removed from (e.g., peeled from) the device to begin device operation. For example, in some embodiments, the actuator can be a peel-off strip that covers a window through which the signal is read. In yet other embodiments, the actuator can be a lid, similar to the lid 2050 or 6050 that, when closed, also actuates multiple aspects of the device.

After being actuated by a "single button," the molecular diagnostic test device can perform any of the methods described herein. Specifically, the device can heat the biological sample via a heater of the sample preparation module to lyse a portion of the biological sample to produce an input sample, at 14A. Referring to FIG. 3, the biological sample S1 can be heated by the heater 1230 and the resulting lysed sample (i.e., the input sample S2) can be conveyed towards the amplification module 1600. Although the device 1000 does not show any additional sample preparation, in other embodiments, the biological sample can be filtered, separated, eluted, subjected to an enzyme inactivation heating operation, or the like to produce a suitable input sample S2. In other embodiments, however, the method need not include any filtering or other separation techniques.

The input sample is then conveyed to an amplification module within the molecular diagnostic test device, at 14B. Referring to FIG. 3, the amplification module defines a reaction volume, as described above. Accordingly, the input sample is heated within the reaction volume to amplify the nucleic acid within the input sample thereby producing an output solution containing a target amplicon, at 14C. The input solution can be amplified by using any suitable technique (e.g., PCR, isothermal amplification, etc.), as described herein.

After amplification, the device then reacts within a detection module within the molecular diagnostic test device each of (i) the output solution and (ii) a reagent formulated to produce a signal that indicates a presence of the target amplicon within the output solution, at 14D. As shown in FIG. 3, the detection module 1800 includes a detection surface 1821 configured to capture the target amplicon to produce the output signal OP1. The output signal OP1 can be any suitable signal. In some embodiments, the output signal OP1 can be a colorimetric signal that indicates the presence of bound amplicon: if the target pathogen, target amplicon and/or target organism is present, the color product is formed, and if the target pathogen, target amplicon and/or target organism is not present, the color product does not form.

The reagent R can be any suitable reagent of the types described herein and can be introduced into the detection module 1800 by any suitable mechanism. For example, in some embodiments, the reagent can be a catalyst formulated to be bound to the target molecule in response when conveyed into the detection module 1800. In other embodiments, the reagent can be formulated to produce the signal when catalyzed by another reagent already present in the detect module 1600. In some embodiments, the reagent can be a precipitating substrate formulated to produce an insoluble colored particle when the reagent is contacted with a catalyzing agent. The reagent R can present in the detection module before the device is actuated or alternatively, the reagent R can be conveyed into the detection module as a result of the device actuation. For example, in some embodiments, the device can include an on-board reagent module (e.g., reagent module 6700), and when the device is actuated, the device can release the reagent into a manifold or "holding tank" for later use during the procedure. In some embodiments, the device can include a fluid transfer device or a pump, similar to the fluid transfer device 6400 described herein.

The method further includes reading a result associated with the signal, at 15. In some embodiments, the reading can include visually inspecting the device and the detection surface 1821 for a colorimetric signal. In other embodiments, the signal OP1 produced by the detection surface 1821 need not be visible to the naked eye. For example, in some embodiments, the reading can include using a secondary device, such a mobile computing device to scan or otherwise receive the signal OP1. In yet other embodiments, the reading the result can include indirectly reading a secondary signal that conveys the results associated with (or describing) the primary output from the detection surface 1821.

In some embodiments, the method 10 optionally includes discarding, after the reading, the molecular test device. In some embodiments, the amount of sample and reagents can be such that the device can be disposed of via standard, non-regulated waste procedures. In other embodiments, the discarding includes disposing of the used device via standard medical waste procedures.

In some embodiments, the method 10 optionally includes storing the molecular diagnostic test device including any reagents sealed therein for at least six months before use.

Although the method 10 shows the operation of coupling the device to the power source as occurring before the biological sample is conveyed into the device, in other embodiments, any of the steps of the method 10 (or any of the methods described herein) can be performed in any order or can be performed concurrently. For example, in some embodiments, the biological sample S1 can be conveyed into the device first, the device can be actuated (via the actuator 1050), and then after actuation, the device can be plugged in to an outlet to provide A/C power to the device.

In some embodiments, an apparatus can include a lid (also referred to as a cover) that functions both to cover an input opening and actuate one or more mechanisms of the device when the lid is closed. In this manner, the single act of closing the lid also actuates all aspects of the device, thus simplifying the device actuation and method.

Figure 5:
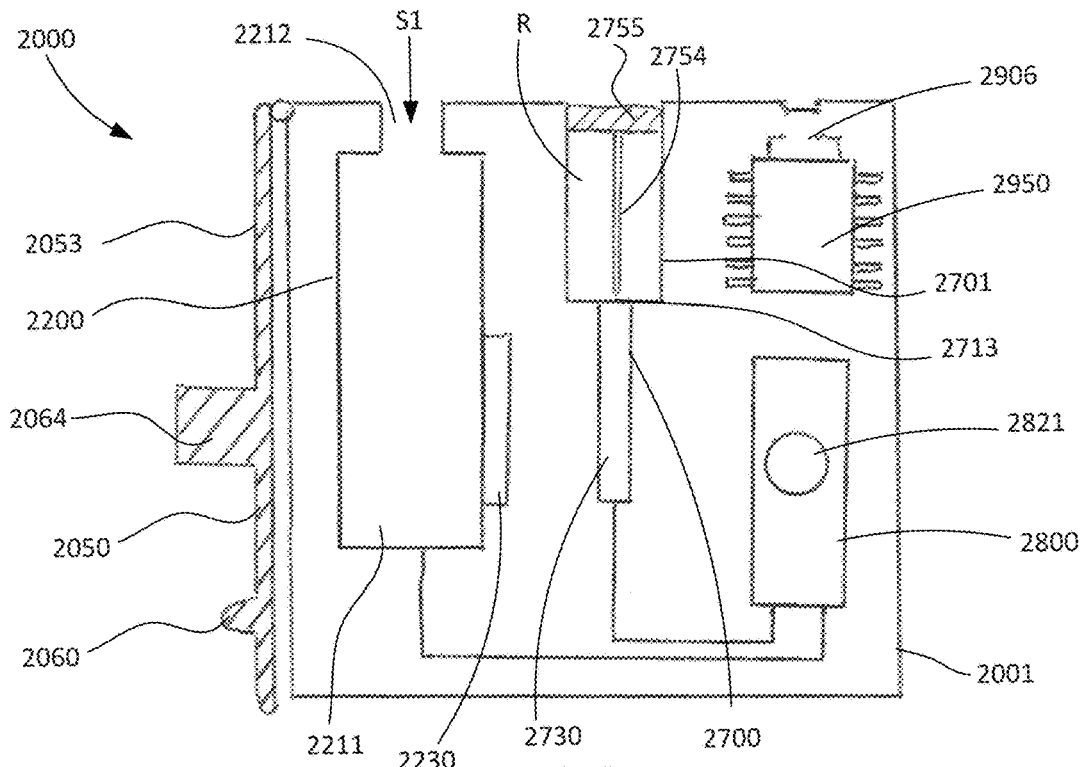
FIGS. 5 and 6 are schematic illustrations of a molecular diagnostic test device, according to an embodiment, in a first configuration and a second configuration, respectively.
Figure 6:
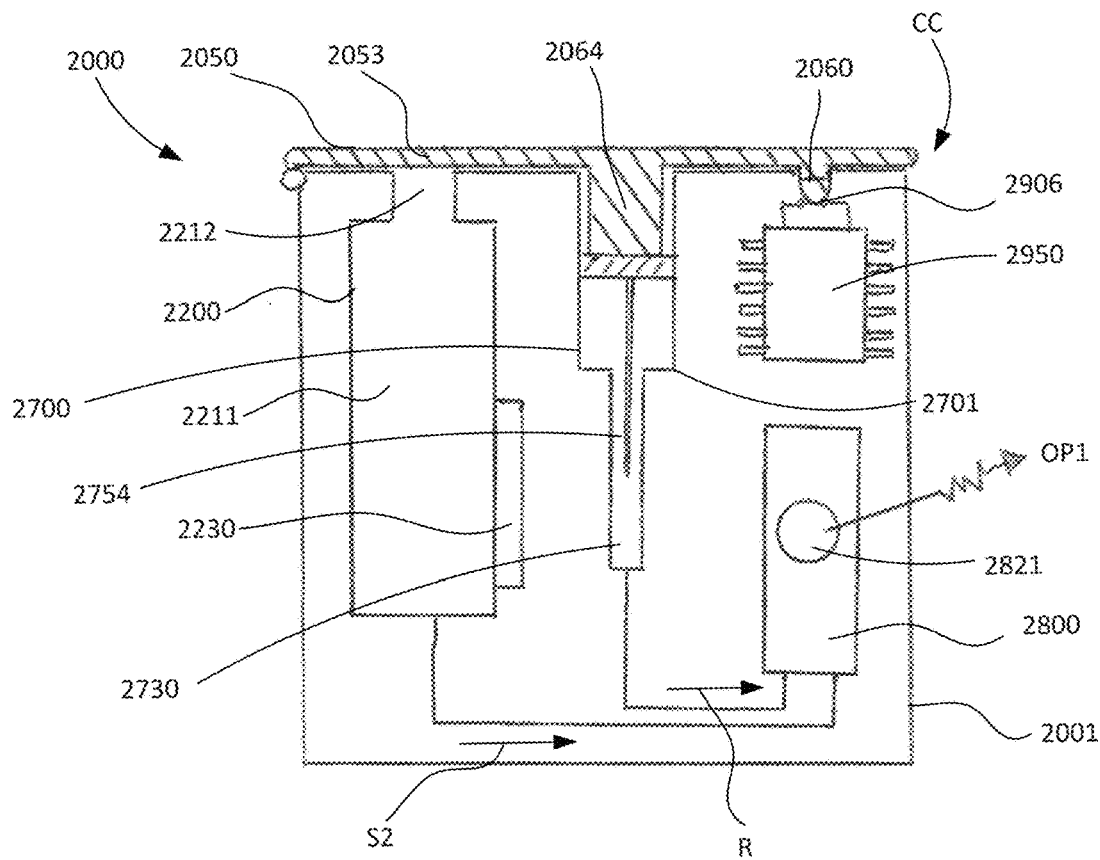

For example, FIGS. 5 and 6 are schematic illustrations of a molecular diagnostic test device 2000 (also referred to as a "test device" or "device"), according to an embodiment. The test device 2000 is configured to manipulate biological sample to produce one or more output signals associated with a target cell, according to any of the methods described herein. In some embodiments, the test device 2000 can be an integrated device that is suitable for use within a point-of-care setting (e.g., doctor's office, pharmacy or the like), decentralized test facility, or at the user's home. Similarly stated, in some embodiments, the modules of the device, described below, are contained within a single housing such that the test device can be fully operated without any additional instrument, docking station, or the like. Further, in some embodiments, the device 2000 can have a size, shape and/or weight such that the device 2000 can be carried, held, used and/or manipulated in a user's hands (i.e., it can be a "handheld" device). In some embodiments, the test device 2000 can be a self-contained, single-use device.

In some embodiments, the device 2000 (and any of the devices shown and described herein) can be a CLIA-waived device and/or can operate in accordance with methods that are CLIA waived. Similarly stated, in some embodiments, the device 2000 (and any of the other devices shown and described herein) is configured to be operated in a sufficiently simple manner and can produce results with sufficient accuracy to pose a limited likelihood of misuse and/or to pose a limited risk of harm if used improperly. In some embodiments, the device 2000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 2000 can be configured for long term storage in a manner that poses a limited likelihood of misuse (spoilage of the reagent(s), expiration of the reagents(s), leakage of the reagent(s), or the like). In some embodiments, the molecular diagnostic test device 2000 is configured to be stored for up to about 36 months, up to about 32 months, up to about 26 months, up to about 24 months, up to about 20 months, up to about 18 months, up to 12 months, up to 6 months, or any values there between.

The test device 2000 includes a housing 2001, a lid 2050, a sample preparation module 2200 (also referred to as a sample staging module), a reagent module 2700, a detection module 2800, and an electronic control module 2950. In some embodiments, the test device 2000 can include any other components or modules described herein, such as, for example, an amplification module (e.g., the amplification module 1600 or 6600), a rotary valve (e.g., to control flow of reagents and/or sample, such as the valve 6300), or a fluid transfer module (e.g., the fluid transfer module 6400). The housing 2001 can be any structure within which the sample preparation module 2200 or other components are contained (or partially contained) to form an integrated device for sample preparation and/or molecular testing.

The sample preparation module 2200 defines a sample input volume 2211 that receives a biological sample S1 and an input opening 2212 through which a biological sample S1 can be conveyed into the sample preparation module 2200. The sample preparation module 2200 includes a heater 2230 and is configured to manipulate the biological sample S1 for further diagnostic testing. For example, in some embodiments, the sample preparation module 2200 can extract nucleic acid molecules from the biological sample S1 and can produce an input solution S2 (see FIG. 6) that is optionally conveyed into an amplification module (not shown), or into the detection module 2800. The sample preparation module 2200 can include any other components described herein, such as, for example, a heater for lysis, a chamber within which RT-PCR can be performed, and/or an inactivation chamber (see, e.g., the lysing housing 6201).

The reagent module 2700 is disposed within the housing 2001 and includes a reagent container 2701, a plunger 2755, and a reagent reservoir 2730. The reagent module 2700 provides on-board storage of the reagent R used in connection with the molecular diagnostic tests described herein. The reagent R can be any reagent of the types shown and described herein. For example, in some embodiments, the reagent R can be a detection reagent formulated to facilitate production of a signal that indicates a presence of a target amplicon from the input solution S2. Thus, the reagent R can be formulated to include a binding moiety and any suitable enzyme such as horseradish peroxidase (HRP) or alkaline phosphates. In some embodiments, the HRP enzyme already conjugated to a streptavidin molecule. In some embodiments, the reagent R can be a substrate that, when catalyzed, produces color molecules. In other embodiments, the reagent R can be a wash buffer or a blocking agent, each of which can facilitate production of the signal (e.g., by reducing spurious output), as described herein.

Prior to actuation, the reagent R is sealed within the reagent container 2701. In some embodiments, the reagent R can be sealed by a frangible portion 2713 of the reagent container 2701. In other embodiments, the reagent container 2701 can include any suitable sealing mechanism. By sealing the reagent R within the reagent container 2701, the device 2000 can be suitable for long term storage and the reagent R can be protected from degradation, and the like. The reagent plunger 2755 includes a puncturer 2754. As shown in FIG. 5, prior to actuation, the puncturer is spaced apart from the frangible portion 2713, thereby maintaining the sealed arrangement of the container. As shown in FIG. 6, after the device is actuated, the puncturer pierces the frangible portion 2713, thereby allowing the reagent R to flow into the reagent reservoir 2730 for later use during the molecular diagnostic methods described herein. Specifically, as shown, the reagent plunger 2755 and the puncturer 2754 collectively move within the reagent container 2701 to pierce the frangible portion 2713 and push the reagent R towards the reagent reservoir 2730. Although the reagent module 2700 is shown as including a non-moving reagent container 2701 and a moving puncturer 2754, in other embodiments, the puncturer can be non-moving and the reagent container can move (see e.g., the reagent module 6700).

The detection module 2800 is configured to react the input solution S2 from the sample preparation module 2200 (or optionally an amplification module) with one or more reagents to produce a signal (or output) OP1 to indicate presence or absence of a target organism in the biological sample S1. Specifically, the detection module 2800 defines a detection channel and includes a detection surface 2821 within the detection channel. The detection channel is in (or can be placed in) fluid communication with each of the sample preparation module 2200 and the reagent module 2700. In this manner, the input solution S2 containing the target amplicon can be conveyed into the detection channel and across the detection surface 2821. Additionally, as shown in FIG. 6, the reagent R can also be conveyed into the detection channel and across the detection 2821. The detection surface 2821 includes a series of capture probes to which the target amplicon can be bound when the input solution S2 flows across the detection surface 2821. The capture probes can be any suitable probe of the types described herein formulated to capture or bind to the target amplicon. When the reagent R reacts with captured input solution S2, the signal OP1 is produced from the detection surface 2821.

The electronic control module 2950 is within the housing 2001 and can automatically control the heaters (e.g., the heater 223), valves, pumps, power delivery and/or any other components of the diagnostic device 2000 to facilitate the molecular testing as described herein. The electronic control module 2950 can include a memory, a processor, an input/output module (or interface), and any other suitable modules or software to perform the functions described herein. As shown in FIGS. 5 and 6, the electronic control module 2950 includes a switch 2906 that, when actuated, initiates the molecular diagnostic testing. The electronic control module 2950 can be powered by any suitable power source described herein, including the power source 1905 described above.

The lid 2050 is movably coupled to the housing 2001 and performs a variety of functions, thereby facilitating actuation of the device 2000 via a single action. As shown, the lid 2050 includes a seal portion 2053, a switch portion 2060, and reagent actuator 2064. As shown by the arrow CC, the lid 2050 is configured to move relative to the housing 2001 from a first (or opened) position (FIG. 5) to a second (or closed) position (FIG. 6). As shown in FIG. 5, the seal portion 2053 (also referred to as a cover portion) is spaced apart from the input opening 2212 when the lid 2050 is in the opened position. Similarly stated, when the lid 2050 is in the opened position, the input opening 2212 is exposed, thereby allowing the biological sample S1 to be conveyed into the sample preparation module 2200. After the biological sample S1 is loaded, the user can close the lid 2050 (i.e., can move the lid to its second position). As shown in FIG. 6, the seal portion 2053 covers the input opening 2212 when the lid 2050 is in the closed position. In some embodiments, the seal portion 2053 includes a seal, gasket, or other material to fluidically isolate the sample input volume 2211 when the lid 2050 is in the second lid position.

In addition to covering the input opening 2212, closing the lid 2050 also actuates other mechanisms within the device 2000. Specifically, as shown in FIG. 6, the switch portion 2060 actuates the switch 2906 to provide power to the electronic control module 2950 and/or the heater 2230 when the lid 2050 is moved from the opened position to the closed position. Additionally, the reagent actuator 2064 cause the reagent R to be released from the sealed reagent container 2701 when the lid 2050 is moved from the opened position to the closed position. Specifically, as shown in FIG. 6, the reagent actuator 2064 exerts a force on the reagent plunger 2755, thereby moving the reagent plunger 2755 and the puncturer 2754. As shown in FIG. 6, the puncturer pierces the frangible portion 2713, thereby allowing the reagent R to flow into the reagent reservoir 2730.

Figure 7:
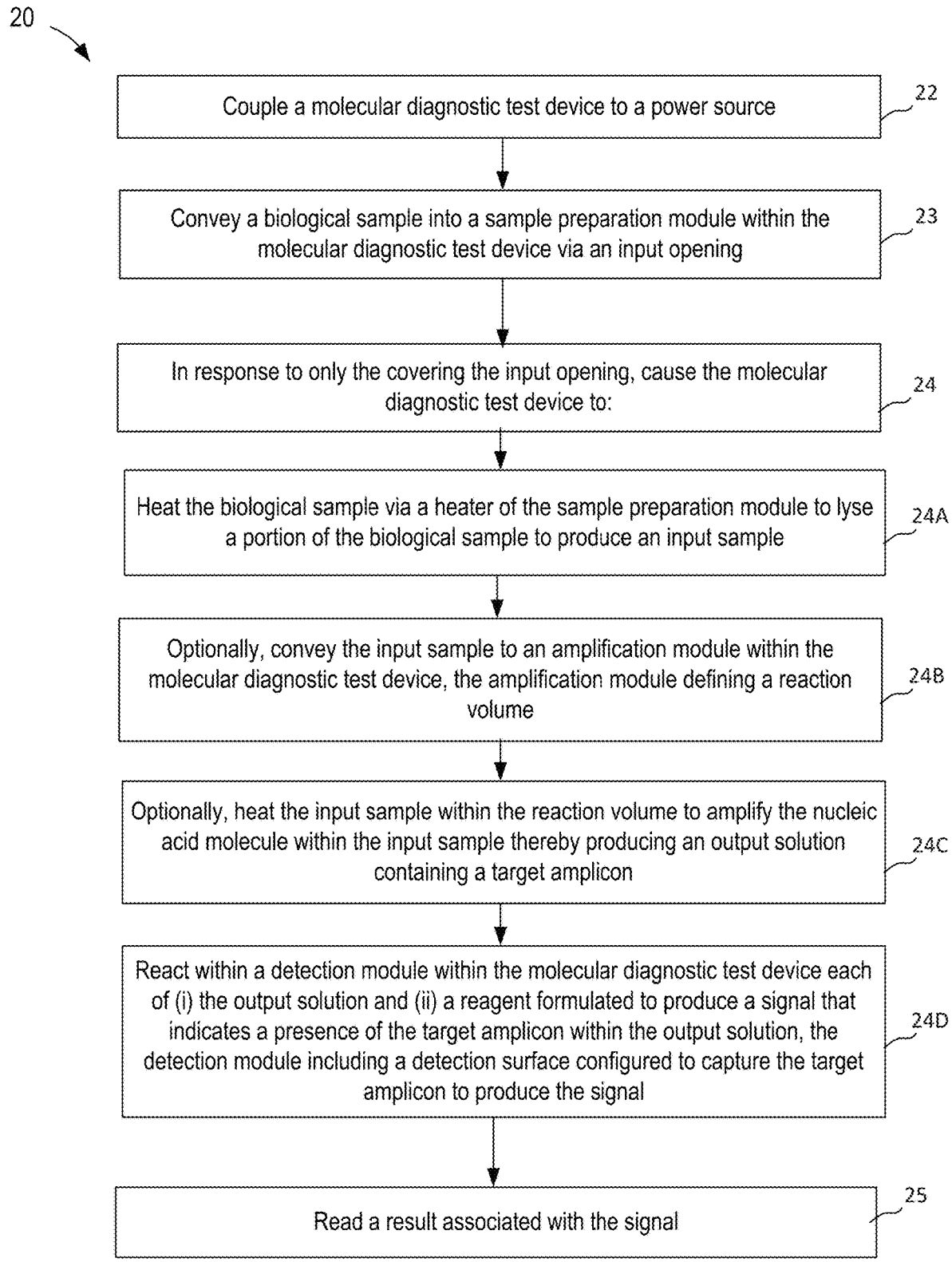
FIG. 7 is a flow chart of a method of detecting a nucleic acid, according to an embodiment.

The molecular diagnostic test device 2000 (and any of the molecular diagnostic test devices described herein) can perform any of the "one touch" actuation methods described herein. For example, FIG. 7 is a flow chart of a method 20 of detecting a nucleic acid, according to an embodiment. Although the method 20 is described as being performed on the device 2000, in other embodiments, the method 20 can be performed on any suitable device, such as the device 6000 described below. The method 20 includes coupling the molecular diagnostic test device to a power source, at 22. The power source (not shown in FIGS. 5 and 6) can be any suitable power source, such as an alternating current (A/C) power source, a direct current (D/C) power source (e.g., a battery), a fuel cell, or the like.

A biological sample is conveyed into a sample preparation module within the molecular diagnostic test device via an input opening, at 23. The biological sample S1 can be conveyed into the device by any suitable mechanism, such as the sample transfer device 1110 described above. The biological sample S1 can be any suitable sample, such as, for example, blood, urine, male urethral specimens, vaginal specimens, cervical swab specimens, nasal swab specimens, throat swab specimens, rectal swab specimens, or any other biological samples described herein. Thus, in some embodiments, the biological sample S1 can be a "raw" (or unprocessed) sample.

The molecular diagnostic test device is then actuated by single act of closing the lid to cover the input opening, at 24. This single action of closing the device causes the molecular diagnostic test device to perform a series of operations without any further user input. Referring to FIG. 6, the lid 2050 can be closed by rotating the lid relative the housing 2001. In other embodiments, the lid 2050 can be closed by a sliding action (see, e.g., the device 6000), depressing a portion of the lid or any other suitable closing mechanism. After being actuated by covering the opening, the molecular diagnostic test device can perform any of the methods described herein. Specifically, the act of closing the lid can also actuate an electronic control module (e.g., the electronic control module 2950), release one or more reagents for use in testing (e.g., releasing the reagent R into the reagent reservoir 2730), and/or actuate any other mechanisms within the device to facilitate the molecular diagnostic methods described herein. Specifically, the device can heat the biological sample via a heater of the sample preparation module to lyse a portion of the biological sample to produce an input sample, at 24A. Referring to FIG. 6, the biological sample S1 can be heated by the heater 2230 and the resulting lysed sample (i.e., the input sample S2) can be conveyed towards the detection module 2800 or an amplification module (not shown in FIG. 6). In some embodiments, the method 20 optionally includes conveying the input sample to an amplification module within the molecular diagnostic test device, at 24B. The input sample can then be heated within a reaction volume to amplify the nucleic acid within the input sample thereby producing an output solution containing a target amplicon, at operation 24C. The input solution can be amplified by using any suitable technique (e.g., PCR, isothermal amplification, etc.), as described herein.

After amplification, the device then reacts within a detection module within the molecular diagnostic test device each of (i) the output solution and (ii) a reagent formulated to produce a signal that indicates a presence of the target amplicon within the output solution, at 24D. As shown in FIG. 6, the detection module 2800 includes a detection surface 2821 configured to capture the target amplicon to produce the output signal OP1. The output signal OP1 can be any suitable signal. In some embodiments, the output signal OP1 can be a colorimetric signal that indicates the presence of bound amplicon: if the target pathogen, target amplicon and/or target organism is present, the color product is formed, and if the target pathogen, target amplicon and/or target organism is not present, the color product does not form.

The method further includes reading a result associated with the signal, at 25. In some embodiments, the reading can include visually inspecting the device and the detection surface 2821 for a colorimetric signal. In other embodiments, the signal OP1 produced by the detection surface 2821 need not be visible to the naked eye. For example, in some embodiments, the reading can include using a secondary device, such a mobile computing device to scan or otherwise receive the signal OP1. In yet other embodiments, the reading the result can include indirectly reading a secondary signal that conveys the results associated with (or describing) the primary output from the detection surface 2821.

In some embodiments, the method 20 optionally includes discarding, after the reading, the molecular test device. In some embodiments, the amount of sample and reagents can be such that the device can be disposed of via standard, non-regulated waste procedures. In other embodiments, the discarding includes disposing of the used device via standard medical waste procedures. In some embodiments, the method 20 optionally includes storing the molecular diagnostic test device including any reagents sealed therein for at least six months before use.

In some embodiments, a molecular diagnostic test device and associated methods involve using a multi-purpose reagent to perform both surface blocking and washing functions. In this manner, the quantity of reagents and the simplicity of the device can be improved, thereby facilitating point-of-care use, disposability of the device, and/or operation of the device in accordance with methods that are CLIA waived. Specifically, in some embodiments a multi-purpose reagent can include a blocking agent to reduce the background signals associated with adherence undesirable particles during a detection event. By improving signal quality, such devices and methods can be adaptable for use with limited sample preparation. In addition, the multi-purpose reagent can include a wash agent that removes an unbound constituent from within a detection module. Such methods can include delivering amounts of the multi-purpose reagent at different times in accordance with the desired function of the reagent.

FIGS. 8-11 are schematic illustrations of a molecular diagnostic test device 3000 (also referred to as a "test device" or "device") that includes a multi-purpose reagent, according to an embodiment. The test device 3000 is configured to manipulate biological sample to produce one or more output signals associated with a target cell, according to any of the methods described herein. In some embodiments, the test device 3000 can be an integrated device that is suitable for use within a point-of-care setting (e.g., doctor's office, pharmacy or the like), decentralized test facility, or at the user's home. Similarly stated, in some embodiments, the modules of the device, described below, are contained within a single housing such that the test device can be fully operated without any additional instrument, docking station, or the like. Further, in some embodiments, the device 3000 can have a size, shape and/or weight such that the device 3000 can be carried, held, used and/or manipulated in a user's hands (i.e., it can be a "handheld" device). In some embodiments, the test device 3000 can be a self-contained, single-use device.

In some embodiments, the device 3000 (and any of the devices shown and described herein) can be a CLIA-waived device and/or can operate in accordance with methods that are CLIA waived. Similarly stated, in some embodiments, the device 3000 (and any of the other devices shown and described herein) is configured to be operated in a sufficiently simple manner and can produce results with sufficient accuracy to pose a limited likelihood of misuse and/or to pose a limited risk of harm if used improperly. In some embodiments, the device 3000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 3000 can be configured for long term storage in a manner that poses a limited likelihood of misuse (spoilage of the reagent(s), expiration of the reagents(s), leakage of the reagent(s), or the like). In some embodiments, the molecular diagnostic test device 3000 is configured to be stored for up to about 36 months, up to about 32 months, up to about 28 months, up to about 24 months, up to about 20 months, up to about 18 months, up to 12 months, up to 6 months, or any values there between.

The test device 3000 includes a housing 3001, a sample preparation module 3200 (also referred to as a sample staging module), a reagent module 3700, and a detection module 3800. In some embodiments, the test device 3000 can include any other components or modules described herein, such as, for example, an amplification module (e.g., the amplification module 1600 or 6600), a rotary valve (e.g., to control flow of reagents and/or sample, such as the valve 6300), or a fluid transfer module (e.g., the fluid transfer module 6400). The housing 3001 can be any structure within which the sample preparation module 3200 or other components are contained (or partially contained) to form an integrated device for sample preparation and/or molecular testing.

The sample preparation module 3200 defines a sample input volume 3211 that receives a biological sample S 1. The sample preparation module 3200 can include any components as described herein to manipulate the biological sample S1 for further diagnostic testing and/or to produce a solution for detection of a nucleic acid. For example, in some embodiments, the sample preparation module 3200 can include one or more heaters, one or more chambers within which the biological sample S1 can be manipulated, one or more mixing chambers, and/or certain on-board reagents (e.g., a lysing buffer, an RT enzyme, a control organism, or the like). In some embodiments, the sample preparation module 3200 is configured to extract nucleic acid molecules from the biological sample S1 and can produce an input solution S2 (see FIG. 10) that is optionally conveyed into an amplification module (not shown), or into the detection module 3800.

The reagent module 3700 is disposed within the housing 3001 and includes a first reagent container 3701, a first reagent actuator 3755, a second reagent container 3702, and a second reagent actuator 3765. The reagent module 3700 provides on-board storage of a first reagent R1 (within the first reagent container 3701) and a second reagent R2 (within the second reagent container 3702) used in connection with the molecular diagnostic tests described herein. In some embodiments, the first reagent R1 is sealed within the first reagent container 3701 and the second reagent R2 is sealed within the second reagent container 3702. In some embodiments, the reagent module 3700 can include one or more puncturers (see, e.g., the puncturer of the reagent module 2700 or the puncturer of the reagent module 6700) that, upon device actuation, can release the reagents for use.

The first reagent R1 is a multi-purpose reagent and includes a blocking agent and a wash buffer. In some embodiments, the blocking agent includes bovine serum albumin and the wash buffer includes a detergent. Moreover, in some embodiments, the first reagent R1 includes between 0.02 percent and 5 percent bovine serum albumin and between 0.05 percent and 10 percent of the detergent. The inclusion of a blocking agent can facilitate achieving repeatable and accurate results in methods that, like those described herein, employ limited sample preparation (i.e., limited filtering, separation, or the like). Specifically, when the biological sample S1 is subject to limited sample preparation, molecules that are not desired for producing the output signal associated with the target nucleic acid (i.e., "unwanted molecules") can adhere to surfaces in the detection module 3800. The adherence of unwanted molecules, especially in non-detection surfaces result in the production of undesirable background signals. By including a blocking agent, the first reagent R1 can be used to convey the blocking agent into the detection module 3800 to limit the adherence of the unwanted molecules. Similarly stated, as described herein, the first reagent R1 can be used to apply a coating within the detection module to limit undesirable background signals. In other embodiments, the blocking agent within the first reagent R1 can be casein, nonfat milk solids, gelatin, or the like. In yet other embodiments, the blocking agent within the first reagent R1 can be a non-biological blocking agent. Further, by also including a detergent in the first reagent R1, the first reagent R1 can also be used (e.g., at a different time) to remove unbound constituents from the detection module 3800 during a detection event.

In some embodiments, the first reagent R1 can also include a wetting agent to improve the likelihood that the first reagent R1 will sufficiently coat the surfaces within the detection module 3800. In some embodiments, the first reagent R1 can also include an anti-microbial constituent to improve shelf-life of the device 3000.

The second reagent R2 can be a detection reagent formulated to facilitate production of a signal that indicates a presence of a target amplicon from the input solution S2. In some embodiments, the second reagent R2 can be formulated to include a binding moiety and any suitable enzyme such as horseradish peroxidase (HRP) or alkaline phosphates. In some embodiments, the HRP enzyme already conjugated to a streptavidin molecule. In other embodiments, the second reagent R2 can be a substrate that, when catalyzed, produces color molecules.

The detection module 3800 is configured to react the input solution S2 from the sample preparation module 3200 (or optionally an amplification module) with the second reagent R2 to produce one or more signals (or outputs) OP1, OP2 to indicate presence or absence of a target organism in the biological sample S1. Specifically, the detection module 3800 defines a detection channel and includes a first detection surface 3821 and a second detection surface 3822 within the detection channel. The detection module 3800 also includes non-detection surfaces 3826 that are adjacent to, surround, or contact either or both of the first detection surface 3821 and the second detection surface 3822. As discussed above, by limiting any background signal produced from the non-detections surfaces 3826, the overall accuracy of the device 3000 and associated molecular diagnostic methods can be improved.

The detection channel is in (or can be placed in) fluid communication with each of the sample preparation module 3200 and the reagent module 3700. In this manner, the input solution S2 containing the target amplicon can be conveyed into the detection channel and across the detection surface 3821. Additionally, as shown in FIG. 11, the second reagent R2 can also be conveyed into the detection channel and across the detection surfaces 3821, 3822. The detection surfaces 3821, 3822 include a series of capture probes to which the target amplicon can be bound when the input solution S2 flows across the detection surfaces 3821, 3822. The capture probes can be any suitable probe of the types described herein formulated to capture or bind to the target amplicon. When the second reagent R2 reacts with captured input solution S2, the first signal OP1 is produced from the first detection surface 3821 and the second signal OP2 is produced from the second detection surface 3822.

Figure 12:
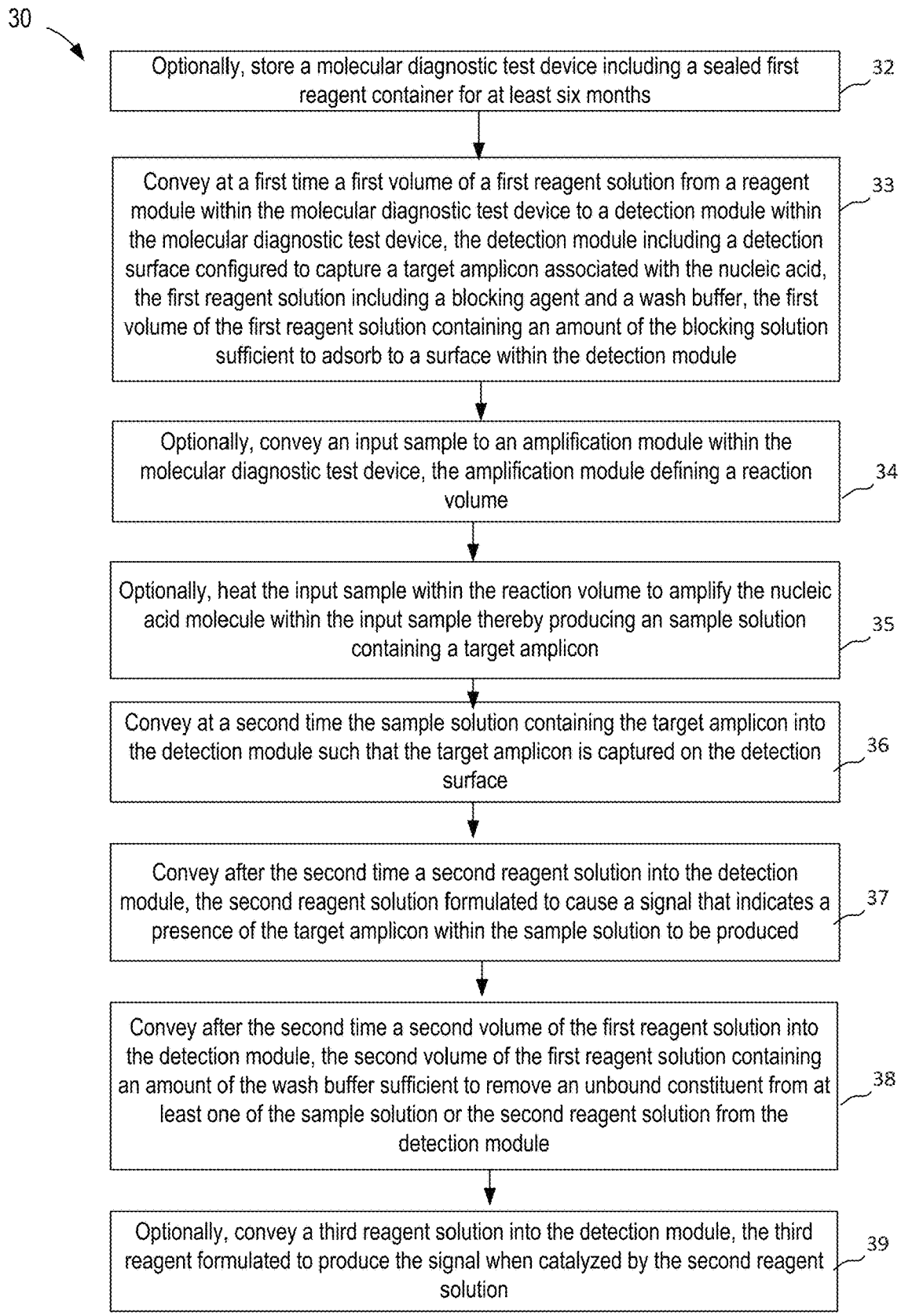
FIG. 12 is a flow chart of a method of detecting a nucleic acid that uses a multi-purpose reagent, according to an embodiment.

The molecular diagnostic test device 3000 (and any of the molecular diagnostic test devices described herein) can perform any of the methods described herein. For example, FIG. 12 is a flow chart of a method 30 of detecting a nucleic acid, according to an embodiment. Although the method 30 is described as being performed on the device 3000, in other embodiments, the method 30 can be performed on any suitable device, such as the device 6000 described below. The method 30 optionally includes storing the molecular diagnostic test device including any reagents sealed therein for at least six months before use, at 32. For example, the device 3000 including the first reagent R1 and the second reagent R2 can be stored for at least six months as part of a stockpiling program.

To initiate a molecular diagnostic test, the method 30 optionally includes conveying a biological sample into a sample preparation module within the molecular diagnostic test device. Referring to FIG. 8, the biological sample S1 can be conveyed into the device by any suitable mechanism, such as the sample transfer device 3110. The biological sample S1 can be any suitable sample, such as, for example, blood, urine, male urethral specimens, vaginal specimens, cervical swab specimens, nasal swab specimens, throat swab specimens, rectal swab specimens, or any other biological samples described herein. Thus, in some embodiments, the biological sample S1 can be a "raw" (or unprocessed) sample.

A first volume of a first reagent R1 is conveyed, at a first time, from a reagent module within the molecular diagnostic test device to a detection module within the molecular diagnostic test device, at 33. The detection module can be similar to the detection module 3800 and includes a detection surface 3821 configured to capture a target amplicon associated with the nucleic acid and one or more non-detection surfaces 3826. As described above, the first volume of the first reagent R1 contains an amount of the blocking solution sufficient to adsorb to a surface (including the detection surface 3821 and the non-detection surfaces 3826) within the detection module 3800. Referring to FIG. 9, the first volume can be conveyed by moving the first reagent actuator 3755 as shown by the arrow DD. The flow of the first volume of the first reagent R1 is shown by the arrows EE. In some embodiments, the first time (i.e., the time at which the first portion is conveyed into the detection module) occurs a sufficient before the remaining operations of the method to allow the blocking agent to sufficiently coat and adsorb within the detection module 3800. For example, in some embodiments, the first time occurs at least 3 minutes before subsequent steps involving flowing solutions into the detection module. In some embodiments, for example, the first volume of the first reagent R1 can be conveyed into the detection module 3800 while the biological sample S1 is being heated and/or processed within the sample input module 3200. In this manner, the "blocking operation" does not add to the total test duration.

The biological sample S1 can be heated within the sample preparation module 3200 and the resulting lysed sample (i.e., the input sample S2) can be conveyed towards the detection module 3800 or an amplification module (not shown in FIGS. 8-11). In some embodiments, the method 30 optionally includes conveying the input sample to an amplification module within the molecular diagnostic test device, at 34. The input sample can then be heated within a reaction volume to amplify the nucleic acid within the input sample thereby producing an output solution containing a target amplicon, at 35. The input solution can be amplified by using any suitable technique (e.g., PCR, isothermal amplification, etc.), as described herein.

After the optional amplification, the method includes conveying at a second time a sample solution containing the target amplicon into the detection module such that the target amplicon is captured on the detection surface, at 36. Referring to FIG. 10, the sample (or input) solution is shown by the arrow S2. As described above, the first detection surface 3821 and the second detection surface 3822 each include a series of capture probes to which the target amplicon can be bound when the input solution S2 flows across the detection surfaces 3821, 3822. Moreover, by applying the blocking agent to the surfaces within the detection module, the likelihood of adsorption of non-specific proteins is reduced. In some embodiments, the method can optionally include conveying an amount of the first reagent R1 into the detection module to wash unbound constituents from the detection module. Specifically, the first reagent solution contains an amount of the wash buffer sufficient to remove an unbound constituent from at least one of the sample solution or the second reagent solution from the detection module. As shown in FIG. 10, the first reagent R1 can be conveyed into the detection module by further actuating the first reagent actuator 3755.

Referring to FIG. 12, after the second time a second reagent is conveyed into the detection module, at 37. As shown in FIG. 11, the second reagent R2 can be conveyed by moving the second reagent actuator 3765 as shown by the arrow FF. The second reagent R2 can flow across the detection surfaces, as shown. The second reagent can be the reagent R2 described above, and is formulated to cause a signal that indicates a presence of the target amplicon within the sample solution to be produced. The method further includes conveying after the second time a second volume of the first reagent into the detection module, at 38. The second volume of the first reagent solution contains an amount of the wash buffer sufficient to remove an unbound constituent from at least one of the sample solution or the second reagent solution from the detection module.

In some embodiments, the method optionally includes conveying a third reagent into the detection module, at 39. The third reagent can be, for example, a substrate or other substance that is formulated to produce the signal when catalyzed by the second reagent R2. In this manner, the device can each of (i) the output solution and (ii) the reagents formulated to produce a signal that indicates a presence of the target amplicon within the output solution. In some embodiments, the method includes providing a continuous flow of the third reagent through the detection module. Specifically, in some embodiments, the third reagent includes a precipitating substrate formulated to produce color molecules when catalyzed by the second reagent R2 captured on the detection surface. Because the third reagent is a precipitating substrate, the color molecules produced will settle onto the detection surface. Moreover, by continuously replenishing the third reagent (i.e., the precipitating substrate), the reaction producing the color molecules will not be limited by the concentration (or amount) of the third reagent. Similarly stated, by continuously flowing the third reagent over the detection surfaces (and the captured second reagent R2), the reaction producing the color molecules will not be diffusion limited. Rather, the reaction will be kinetically (or rate) limited, and therefore will be faster than if a set amount of the third reagent is maintained within the detection module.

In some embodiments, the method optionally includes reading a result associated with the signal, as described herein.

Although FIGS. 9 and 10 show the first volume of the first reagent R1 and the second volume of the first reagent R1 being conveyed moving the first reagent actuator 3755 in the same direction, in other embodiments, any suitable mechanism for conveying the desired amount of the first reagent R1 can be applied. For example, in some embodiments, the first reagent can be recycled (or reused) within the device 3000 (or any other device). Specifically, a first volume of the first reagent can be applied for blocking purposes, and then can be returned to the reagent module for later reuse for washing purposes. By recycling the first reagent for multiple purposes, the amount of reagent needed is reduced, which allows for smaller packaging, lower cost, and the like.

Figure 13:
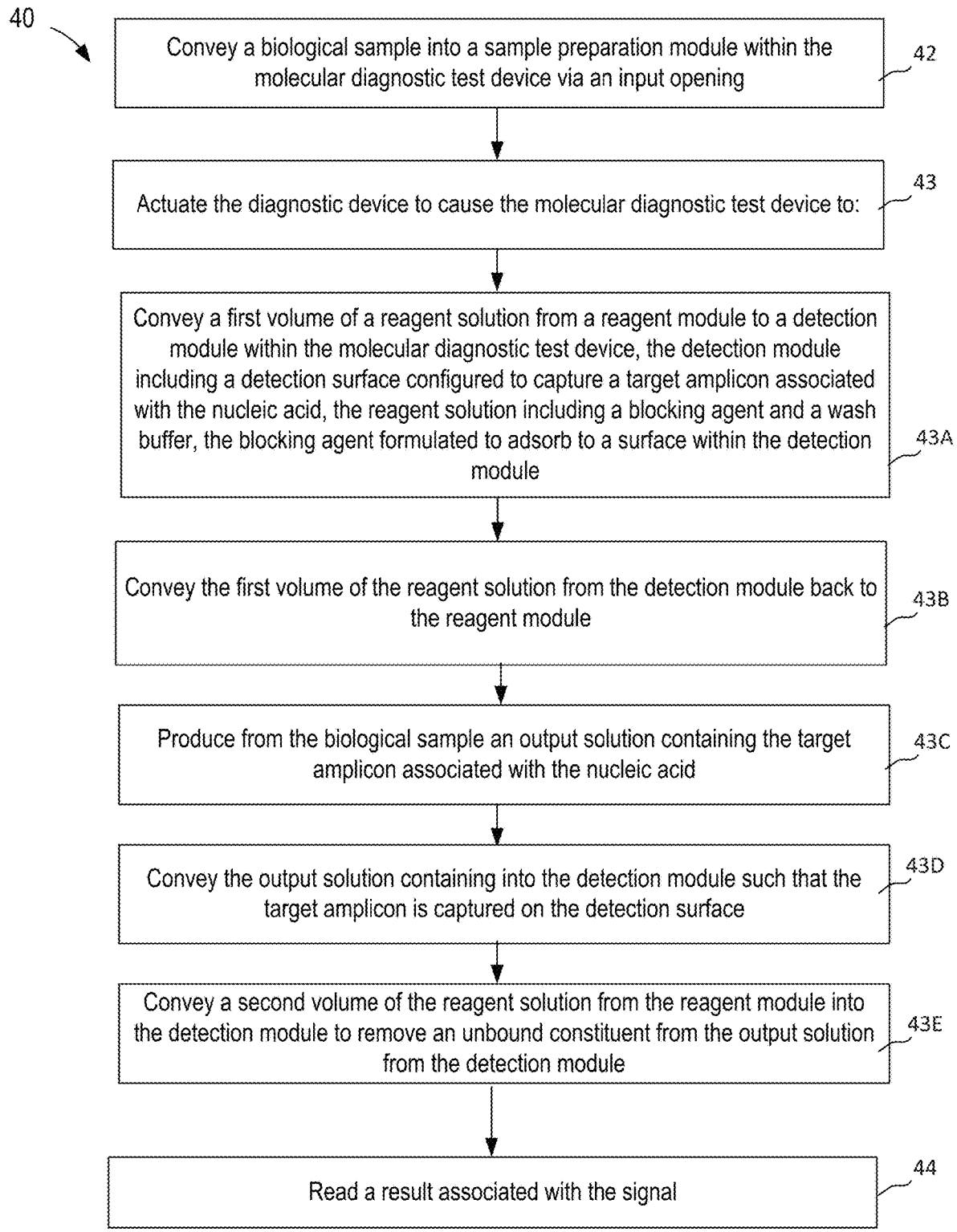
FIG. 13 is a flow chart of a method of detecting a nucleic acid that includes reusing a reagent, according to an embodiment.

For example, FIG. 13 is a flow chart of a method 40 of detecting a nucleic acid, according to an embodiment. Although the method 40 is described as being performed on the device 3000, in other embodiments, the method 40 can be performed on any suitable device, such as the device 6000 described below. To initiate a molecular diagnostic test, the method 40 includes conveying a biological sample into a sample preparation module within the molecular diagnostic test device, at 42. The biological sample S1 can be any suitable sample, such as, for example, blood, urine, male urethral specimens, vaginal specimens, cervical swab specimens, nasal swab specimens, or any other biological samples described herein. Thus, in some embodiments, the biological sample S1 can be a "raw" (or unprocessed) sample.

The molecular diagnostic test device is then actuated (e.g., in some embodiments, by a single action) to cause the molecular diagnostic test device to perform a series of operations, at 43. As a result of actuation, a first volume of a first reagent R1 is conveyed, at a first time, from a reagent module within the molecular diagnostic test device to a detection module within the molecular diagnostic test device, at 43A. The detection module can be similar to the detection module 3800 and includes a detection surface 3821 configured to capture a target amplicon associated with the nucleic acid and one or more non-detection surfaces 3826. As described above, the first volume of the first reagent R1 contains an amount of the blocking solution sufficient to adsorb to a surface (including the detection surface 3821 and the non-detection surfaces 3826) within the detection module 3800. The device then conveys the first volume of the first reagent R1 back towards the reagent module, at 43B. This can be accomplished, for example, by moving the first reagent actuator 3755 in a direction opposite that shown by the arrow DD in FIG. 9 to draw the first reagent R1 back into the reagent module 3700. In some embodiments, the method can include allowing the first volume of the first reagent to be maintained in the detection module for a dwell time to allow the blocking function (i.e., the adsorption) to occur. The dwell time can be, for example, at least 1 minute, 2 minutes, at least 3 minutes, or at least 4 minutes. In some embodiments, the method can include heating the detection module (e.g., to a temperature of at least 30 C, 40 C or 50 C) to facilitate adsorption.

The device can heat the biological sample via a heater to produce an output sample containing the target amplicon, at operation 43C. Said another way, the input sample can be heated within a reaction volume to amplify the nucleic acid within the input sample thereby producing an output solution containing a target amplicon. The input solution can be amplified by using any suitable technique (e.g., PCR, isothermal amplification, etc.), as described herein.

After the amplification, the method includes conveying at a second time a sample solution containing the target amplicon into the detection module such that the target amplicon is captured on the detection surface, at 43D. The device then conveys a second volume of the first reagent into the detection module, at 43E. The second volume of the first reagent solution contains an amount of the wash buffer sufficient to remove an unbound constituent from at least one of the sample solution or the second reagent solution from the detection module.

The method further includes reading a result associated with the signal, at 44. In some embodiments, the reading can include visually inspecting the device and the detection surfaces 3821, 3822 for a colorimetric signal. In other embodiments, the signal OP1 produced by the detection surfaces need not be visible to the naked eye. For example, in some embodiments, the reading can include using a secondary device, such a mobile computing device to scan or otherwise receive the signals OP1, OP2. In yet other embodiments, the reading the result can include indirectly reading a secondary signal that conveys the results associated with (or describing) the primary output from the detection surfaces.

Figure 14:
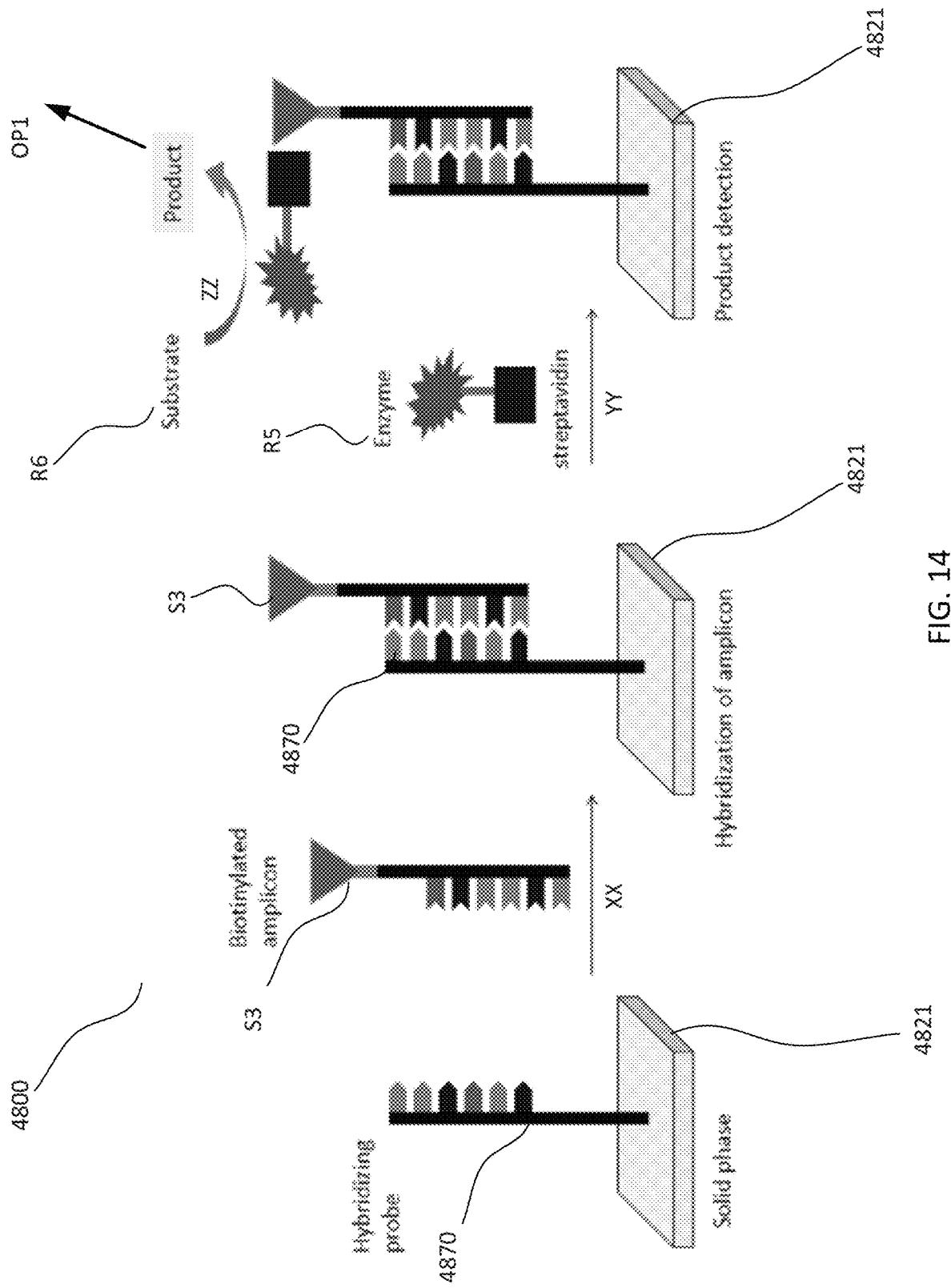
FIG. 14 is a diagram illustrating an enzyme linked reaction, according to an embodiment, resulting in the production a signal.

FIG. 14 illustrates a portion of the operations and/or features associated with an enzymatic reaction, according to an embodiment, that can be conducted by or within the detection module 3800, the detection module 4800, or any other detection module described herein (e.g., the detection module 6800). In some embodiments, the enzymatic reaction can be carried out to facilitate visual detection of a molecular diagnostic test result using the device 3000, the device 4000, the device 5000, the device 6000, or any other devices or systems described herein. In other embodiments, the enzymatic reaction need not be performed to produce visual detection. For example, as described herein, in some embodiments, the methods that employ the illustrated enzymatic reaction can employ alternative methods to read a result associated with signal produced.

In some embodiments, the reaction, the detection module 4800, and/or the remaining components within the device 4000 (or the device 6000) can be collectively configured such that the device is a single-use device that can be used in a point-of-care setting and/or in a user's home. Similarly stated, in some embodiments, the device 4000 (and any of the other devices shown and described herein) can be configured for use in a decentralized test facility. Further, in some embodiments, the reaction shown in FIG. 14 can facilitate the device 4000 (and any of the other devices shown and described herein) operating with sufficient simplicity and accuracy to be a CLIA-waived device. Similarly stated, in some embodiments, the reaction shown in FIG. 14 can provide the output signal OP1 in a manner that poses a limited likelihood of misuse and/or that poses a limited risk of harm if used improperly. In some embodiments, the reaction can be successfully completed within the device 4000 (or any other device described herein) upon actuation by a user with minimal (or no) scientific training, in accordance with methods that require little judgment of the user, and/or in which certain operational steps are easily and/or automatically controlled.

As shown, the detection module 4800 includes a detection surface 4821 within a read lane or flow channel. The detection surface 4821 is spotted and/or covalently bonded with a specific hybridizing probe 4870, such as an oligonucleotide. The hybridizing probe 4870 (also referred to as a capture probe) can be similar to any of the capture probes described herein, including those described in conjunction with the detection surface 3821. In some embodiments, the hybridizing probe 4870 is specific for a target organism, nucleic acid, and/or amplicon. The bonding of the hybridizing probe 4870 to the detection surface 4821 can be performed using any suitable procedure or mechanism. For example, in some embodiments, the hybridizing probe 4870 can be covalently bound to the detection surface 4821.

Figure 15:
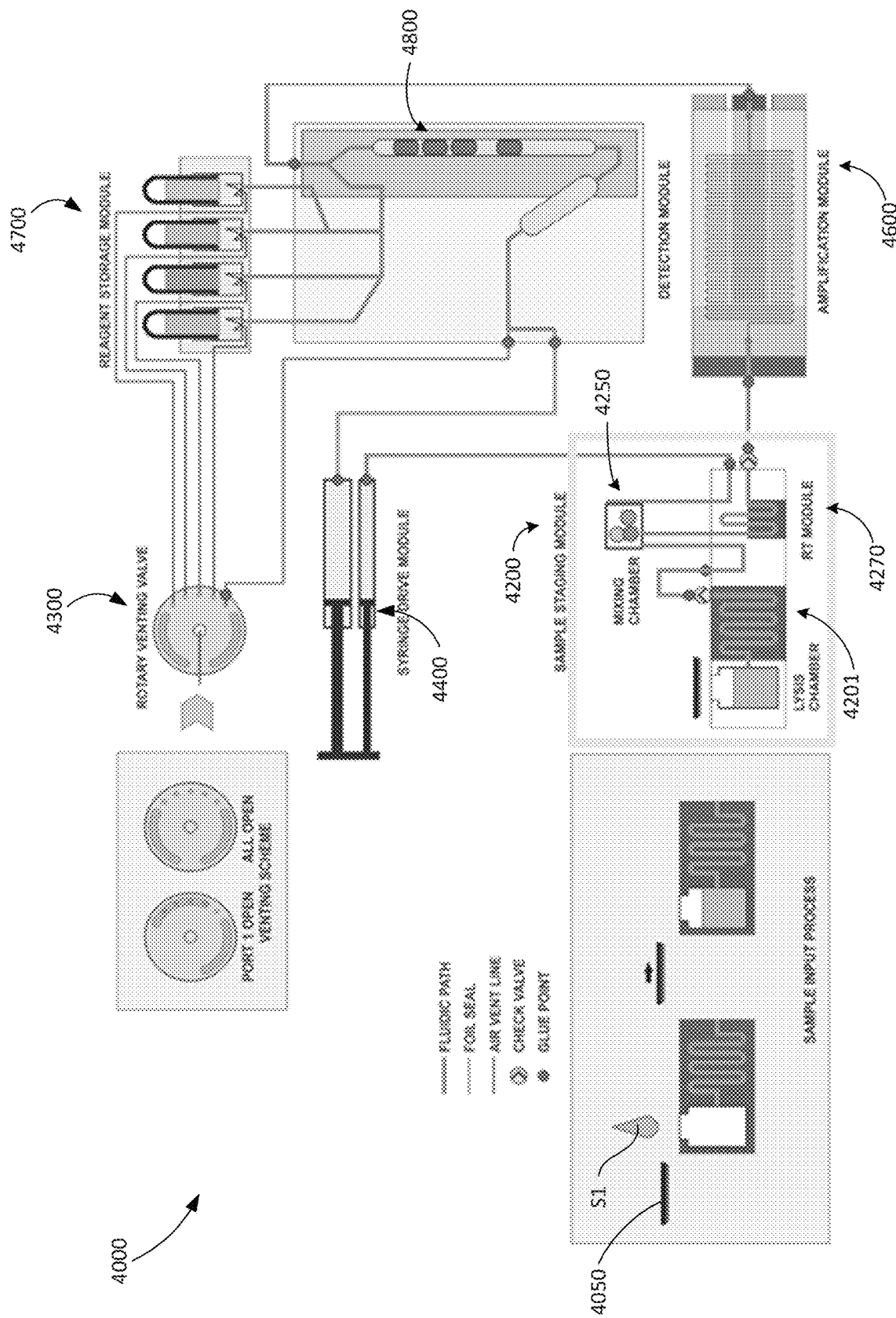
FIG. 15 is a schematic illustration of a molecular diagnostic test device, according to an embodiment.

Reference S3 illustrates the biotinylated amplicon that is produced from the amplification step such as, for example, by the amplification module 4600 of FIG. 15 (or any other amplification modules described herein). The biotin can be incorporated within the amplification operation and/or within the amplification module 4600 in any suitable manner. As shown by the arrow XX, the output from the amplification module, including the biotinylated amplicon S3 is conveyed within the read lane and across the detection surface 4821. The hybridizing probe 4870 is formulated to hybridize to the target amplicon S3 that is present within the flow channel and/or in proximity to the detection surface 4821. The detection module 4800 and/or the detection surface 4821 is heated to incubate the biotinylated amplicon S3 in the read lane in the presence of the hybridizing probe 4870 for a few minutes allowing binding to occur. In this manner, the target amplicon S3 is captured and/or is affixed to the detection surface 4821, as shown. Although disclosed as being labeled with biotin, in other embodiments, the target molecules can be labeled in any suitable manner that will allow binding of the complex comprising a sample molecule binding moiety and an enzyme capable of facilitating a colorimetric reaction. For example, in some embodiments, the target molecules can be labeled with one or more of the following: streptavidin, fluorescein, Texas Red, digoxigenin, or Fucose.

In some embodiments, a first wash solution (not shown in FIG. 14) can be conveyed across the detection surface 4821 and/or within the flow channel to remove unbound PCR products and/or any remaining solution. Such wash solution can be, for example, a multi-purpose reagent, as described above with reference to the device 3000 and the first reagent R1 of the method 30 and the method 40. In other embodiments, however, no wash operation is conducted.

As shown by the arrow YY, a detection reagent R5 is conveyed within the read lane and across the detection surface 4821. The detection reagent R5 can be any of the detection reagents described herein. In some embodiments, the detection reagent R5 can be a horseradish peroxidase (HRP) enzyme ("enzyme") with a streptavidin linker. In some embodiments, the streptavidin and the HRP are cross-linked to provide dual functionality. As shown, the detection reagent is bound to the captured amplicon S3. The detection module 4800 and/or the detection surface 4821 is heated to incubate the detection reagent R5 within the read lane in the presence of the biotinylated amplicon S3 for a few minutes to facilitate binding.

In some embodiments, a second wash solution (not shown in FIG. 14) can be conveyed across the detection surface 4821 and/or within the flow channel to remove unbound detection reagent R5. Such wash solution can be, for example, a multi-purpose reagent, as described above with reference to the device 3000 and the first reagent R1 of the method 30 and the method 40. In other embodiments, however, no second wash operation is conducted.

As shown by the arrow ZZ, a detection reagent R6 is conveyed within the read lane and across the detection surface 4821. The detection reagent R6 can be any of the detection reagents described herein. The detection reagent R6 can be, for example, a substrate formulated to enhance, catalyze and/or promote the production of the signal OP1 when reacted with the detection reagent R5. Specifically, the substrate is formulated such that upon contact with the detection reagent R5 (the HRP/streptavidin) color molecules are produced. As such, a colorimetric output signal OP1 is developed where HRP attaches to the amplicon. The color of the output signal OP1 indicates the presence of bound amplicon: if the target pathogen, target amplicon and/or target organism is present, the color product is formed, and if the target pathogen, target amplicon and/or target organism is not present, the color product does not form.

As described above with respect to the method 30, in some embodiments the detection reagent R6 can be continuously flowed across the detection surface 4821 to ensure that the reaction producing the color molecules does not become limited by the availability of the detection reagent. Moreover, in some embodiments, the detection reagent R6 can be a precipitating substrate.

In some embodiments, a method includes lysing a raw sample and performing a reverse transcription polymerase chain reaction (PCR) on the lysed sample to facilitate detection of target RNA, for example to detect a target virus. To facilitate such methods, in some embodiments, a device can include a reverse transcription module to facilitate such methods of isolating and detecting viruses. As one example, FIG. 15 is a schematic illustration of a molecular diagnostic test device 4000 (also referred to as a "test device" or "device") that includes a reverse transcription module 4270, according to an embodiment. The schematic illustration describes the primary components of the test device 4000.

The test device 4000 is an integrated device (i.e., the modules are contained within a single housing) that is suitable for use within a point-of-care setting (e.g., doctor's office, pharmacy or the like), decentralized test facility, or at the user's home. In some embodiments, the device 4000 can have a size, shape and/or weight such that the device 4000 can be carried, held, used and/or manipulated in a user's hands (i.e., it can be a "handheld" device). A handheld device may have dimensions less than 15 cm×15 cm×15 cm, or less than 15 cm×15 cm×10 cm, or less than 12 cm×12 cm×6 cm. In other embodiments, the test device 4000 can be a self-contained, single-use device. Similarly stated, the test device 4000 is a stand-alone device that includes all necessary substances, mechanisms, and subassemblies to perform any of the molecular diagnostic tests described herein. As such, the device 4000 does not require any external instrument to manipulate the biological samples, and only requires a connection to a power source (e.g., a connection to an A/C power source, coupling to a battery, or the like) to complete the methods described herein. In some embodiments, the test device 4000 can be configured with lock-outs or other mechanisms to prevent re-use or attempts to re-use the device.

Further, in some embodiments, the device 4000 can be a CLIA-waived device and/or can operate in accordance with methods that are CLIA waived. Similarly stated, in some embodiments, the device 4000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 4000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 4000 can be configured for long term storage in a manner that poses a limited likelihood of misuse (spoilage of the reagent(s), expiration of the reagents(s), leakage of the reagent(s), or the like). In some embodiments, the molecular diagnostic test device 4000 is configured to be stored for up to about 36 months, up to about 32 months, up to about 26 months, up to about 24 months, up to about 20 months, up to about 48 months, or any values there between.

The test device 4000 is configured to manipulate a biological sample S1 to produce one or more output signals associated with a target cell. Specifically, the device 4000 includes an actuator 4050, a sample preparation (or staging) module 4200, a fluidic drive (or fluid transfer) module 4400, a mixing module 4250, an amplification module 4600, a detection module 4800, a reagent module 4700, a valve 4300, and a power and control module (not shown). The test device and certain components therein can be similar to many of the components of the device 6000 shown and described with reference to FIG. 19. Accordingly, the actuator 4050, the fluidic drive (or fluid transfer) module 4400, the mixing module 4250, the amplification module 4600, the detection module 4800, the reagent module 4700, and the valve 4300 are not described in detail herein. Moreover, the device including a reverse transcription module is similar the reverse transcription devices shown and described in International Patent Publication No. WO2018/005870, entitled "Devices and Methods for Nucleic Acid Extraction," each of which is incorporated herein by reference in its entirety.

The device 4000 differs from the device 1000, the device 2000, the device 3000, and the device 6000 in that the sample preparation module 4200 includes a lysing chamber 4201 and a reverse transcription module 4270. The lysing chamber 4201 can be similar to the lysing chambers shown and described in International Patent Publication No. WO2018/005710, entitled "Devices and Methods for Detection of Molecules Using a Flow Cell," which is incorporated herein by reference in its entirety. Specifically, the lysing module 4300 includes a chamber body and a heater. In use, the sample (either a filtered sample or the raw biological sample S1) is conveyed into the chamber body and can be heated to a first temperature within a lysing temperature range to release a ribonucleic acid (RNA) molecule. The heater can convey thermal energy into the lysing module 4300 to produce a lysing temperature zone within any desired portion of the lysing module 4300 and for any of the time periods described herein. Accordingly, the lysing module can lyse the cells within the biological sample and also lyse the target virus that may be resident within the cells to produce the RNA suitable for a reverse transcription process.

Upon completion of the lysing, the lysed sample can then be mixed with a reverse transcriptase to form a reverse transcription solution. The mixing can be performed in any suitable portion of the device, such as, for example, in the flow paths between the lysing module 4201 and the reverse transcription module 4270. Alternatively, in some embodiments, the mixing of the lysed sample with the reverse transcriptase can occur within the mixing module 4250.

The reverse transcription module 4270 is integrated within the device and includes a flow member and a heater. The flow member defines a reverse transcription flow path through which the lysed sample containing the RNA can be conveyed. The reverse transcription module 4270 is configured to heat the reverse transcription solution to a second temperature within a reverse transcription temperature range to produce a complementary deoxyribonucleic acid (cDNA) molecule. In some embodiments, the reverse transcription module 4270 is configured to heat the reverse transcription solution to a third temperature above an inactivation temperature to cause inactivation of the reverse transcriptase. The reverse transcription solution can then be conveyed to the mixing module 4250 and mixed with the PCR reagents. After mixing, the solution can then be conveyed to the amplification module 4600 and amplified in a manner described herein.

Figure 16:
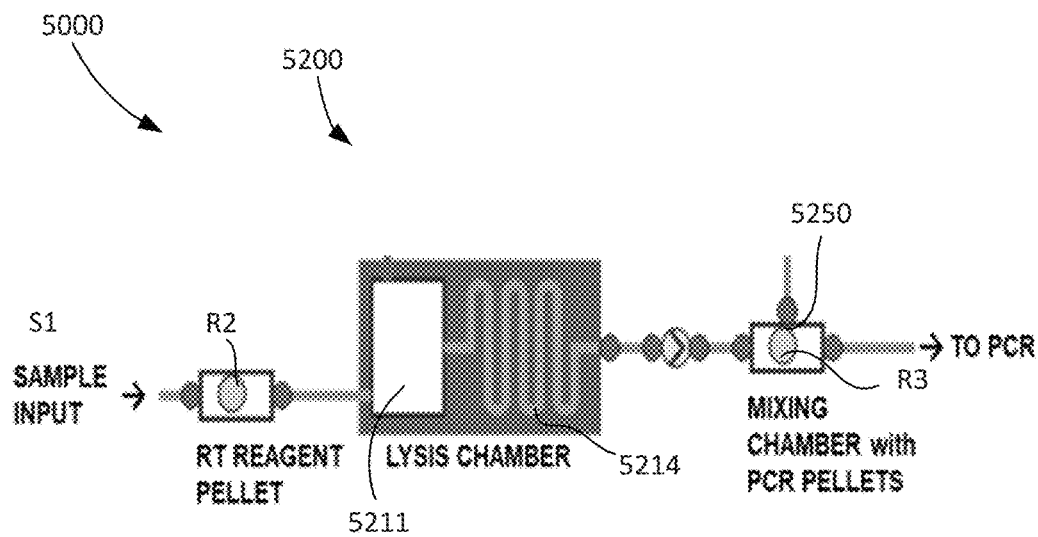
FIG. 16 is a schematic illustration of a portion of a molecular diagnostic test device that includes a single lysis and RT-PCR module, according to an embodiment.

Although the device 4000 is shown and described as including a lysing module 4300 that is separate from the reverse transcription module 4270, in other embodiments, a device and molecular diagnostic methods can include a single chamber or module within which A) a sample can be lysed to produce RNA, B) the RNA can be heated to produce complementary deoxyribonucleic acid (cDNA), and C) the solution can be heated further to inactivate the reverse transcriptase (i.e., the RT enzymes). Similarly stated, in some embodiments, a method includes lysing a raw sample and performing a reverse transcription polymerase chain reaction (PCR) on the lysed sample in the same environment. Said another way, in some embodiments, a device includes a single lysing/RT-PCR module to facilitate methods that include lysing a raw sample and performing a fast RT-PCR in a single chamber. Such methods can be performed in a manner that limits the degradation of the target RNA after lysing, thereby producing an accurate result. Accordingly, such methods are suitable for being performed by point-of-care device that is CLIA waived FIG. 16 is a schematic illustration of a portion of a molecular diagnostic test device 5000 (also referred to as a "test device" or "device") that includes a sample preparation (or staging) module 5200 that can perform lysing, RT-PCR, enzyme inactivation in a single environment (or module). The test device 5000 can have similar characteristics as the device 4000 described above, and is an integrated device (i.e., the modules are contained within a single housing) that is suitable for use within a point-of-care setting (e.g., doctor's office, pharmacy or the like), decentralized test facility, or at the user's home. The sample preparation module 5200 includes an input (or holding) reservoir 5211 and a flow channel 5214 within which the input sample S1 can be heated to perform RT-PCR, among other methods. The sample preparation module also includes the reverse transcriptase R2, which is mixed with the biological sample S1. After completion of the RT-PCR process, the solution is then conveyed to the mixing module 5250 where the solution is mixed with the amplification reagents R3 suitable for performing the desired amplification (e.g., PCR or other methods of amplification). All or portions of the device 5000 can be included within any of the devices described herein. Moreover, the device 5000 can be used to perform any of the RT-PCR methods described herein.

Figure 17A:
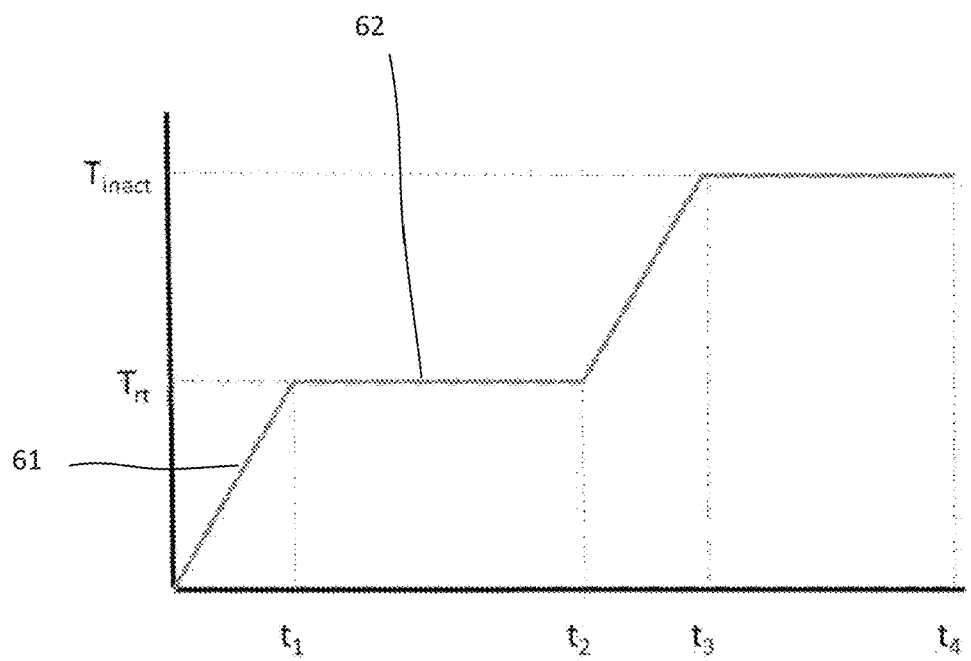
FIGS. 17A-17C are graphs showing a temperature vs. time profile for various methods of lysis and RT-PCR, according to embodiments.
Figure 18:
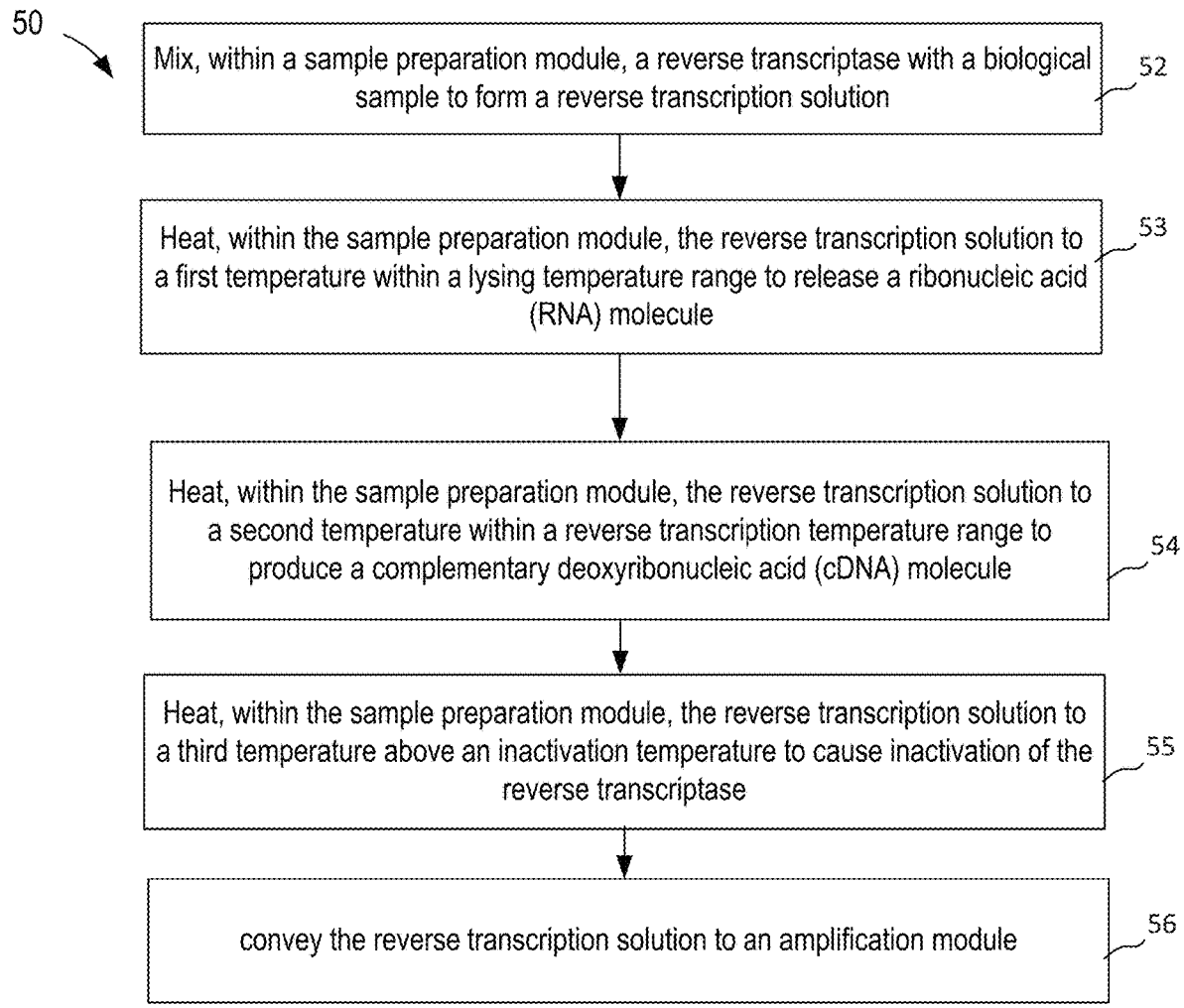
FIG. 18 is a flow chart of a method of detecting a nucleic acid that includes performing lysis and RT-PCR in a single environment, according to an embodiment.

FIG. 17A shows a graph of temperature as a function of time, and FIG. 18 is a flow chart of a method 50 of performing a lysing, reverse transcription and inactivation process in a single module within a hand-held, single-use device. Although the method 50 is described in connection with the temperature performance chart of FIG. 17A, the device 5000, and the device 6000 (described below), in other embodiments, the RT-PCR method 50 can be performed with any suitable device as described herein. The method 50 includes mixing, within a sample preparation module, a reverse transcriptase with a biological sample to form a reverse transcription solution, at 52. The sample preparation module can be a single environment or module, like the sample preparation module 6200 described below. In some embodiments, the reverse transcriptase can be a lyophilized or solid form reagent R4 that is captively maintained in a holding or mixing volume of the sample preparation module (e.g., the holding volume 6211). In some embodiments, the biological sample can be a raw and/or unfiltered sample. In some embodiments, the reverse transcription solution can be devoid of a ribonuclease inhibitor. Specifically, as described herein, in some embodiments, the method 50 can be performed in a manner such that the released RNA undergoes the reverse transcription rapidly so that degradation of the RNA by ribonuclease is limited.

The reverse transcription solution is then heated, within the sample preparation module, to a first temperature within a lysing temperature range to release a ribonucleic acid (RNA) molecule, at 53. The lysing temperature range can be any of the ranges described herein. For example, in some embodiments, the first temperature range can be between about 25 C and about 40 C. In some embodiments, the heating can be performed by a segmented or "multi-zone" heater (e.g., the heater 6230) that conveys thermal energy into the initial volume 6211 of the sample preparation module. Referring to FIG. 17A, in some embodiments, the heating to a first temperature can include heating the reverse transcription solution along a ramp rate, as shown by the region 61 in FIG. 17A. Said another way, in some embodiments, the reverse transcription solution can be heated along a ramp from an initial temperature towards a reverse transcription temperature Trt, and need not be maintained at a constant lysing temperature for a set time period. In this manner, the solution can pass through a lysing temperature range (e.g., 25C to 35C) while being heated towards a target reverse transcription temperature. In other embodiments, however, the method 50 can include maintaining the reverse transcription solution at a constant lysing temperature for a set time period.

The reverse transcription solution is then heated, within the sample preparation module, to a second temperature within a reverse transcription temperature range to produce a complementary deoxyribonucleic acid (cDNA) molecule from the released RN, at 54. The reverse transcription temperature range can be any of the ranges described herein. For example, in some embodiments, the first temperature range can be between about 40 C and about 60 C. In some embodiments, the heating can be performed by a segmented or "multi-zone" heater (e.g., the heater 6230) that conveys thermal energy into the initial volume 6211 of the sample preparation module. In other embodiments, the reverse transcription solution can be conveyed through a serpentine flow channel (e.g., the channel 6214) to facilitate heating by the heater 6230. Referring to FIG. 17, in some embodiments, the heating to the second temperature can include heating the reverse transcription solution and then maintain the solution at a substantially constant target reverse transcription temperature Trt for a time period between t1 and t2, as shown by the region 62 in FIG. 17. In other embodiments, however, the reverse transcription solution can be continuously heated such that the temperature increases along a second ramp rate towards an inactivation temperature Enact, and need not be maintained at a constant reverse transcription temperature for a set time period.

In some embodiments, the solution can be maintained at the second temperature (e.g., Trt) fora suitable time period (e.g., referring to FIG. 17A, between the first time (t1) and the second time (t2) to complete the reverse transcription reaction. In some embodiments, the time can be about 30 seconds, at least 1 minute, at least 2 minutes, at least 3, at least 4 minutes, and at least 5 minutes.

The method further includes heating, within the sample preparation module, the reverse transcription solution to a third temperature above an inactivation temperature to cause inactivation of the reverse transcriptase, at 55. The inactivation temperature range can be any of the ranges described herein. For example, in some embodiments, the first temperature range can be above about 92 C, 93 C, 94 C, 95 C, 96 C, 97 C, 98 C, and about 99 C. In other embodiments, the RT enzyme can be inactivated at much lower temperatures, and the first temperature range can be above about 56 C, 58 C, 60 C, 62 C, 64 C, 68 C, 75 C, and about 80 C. In some embodiments, the third temperature can be maintained for a suitable time period (referring to FIG. 17A, from time t3 to time t4, which provides a suitable amount of time to inactive the RT enzyme). In some embodiments, the heating can be performed by a segmented or "multi-zone" heater (e.g., the heater 6230) that conveys thermal energy into the initial volume 6211 of the sample preparation module. In other embodiments, the reverse transcription solution can be conveyed through a serpentine flow channel (e.g., the channel 6214) to facilitate heating by the heater 6230.

The reverse transcription solution is then conveyed to an amplification module, at 56. Any additional methods for detection of nucleic acid, such as further amplification of the cDNA, can be completed according the methods described herein.

Although FIG. 17A shows the lysing and RT-PCR as being performed in distinct steps, in some embodiments, a method can include performing these operations in a continuous fashion. Similarly stated, in some embodiments, a method can include lysing a cell and/or virus to release RNA and producing, from the released RNA, a cDNA in a continuous, substantially simultaneous operation. In this manner, the time between the releasing of the RNA and the transcription process to produce the cDNA can be minimized such that the potential degradation of the RNA by resident ribonuclease is limited. This further allows any of the methods described herein to be completed without the use of ribonuclease inhibitors or other RNA protection mechanisms (e.g., bead capture, additional filtering or the like). Such methods have been advantageously found to be effective for certain viruses, including the MS bacteriophage and influenza A virus. In other embodiments, such continuous lysing/RT-PCR methods may be performed in detection assays for HIV and all species of Hantavirus.

Figure 17B:
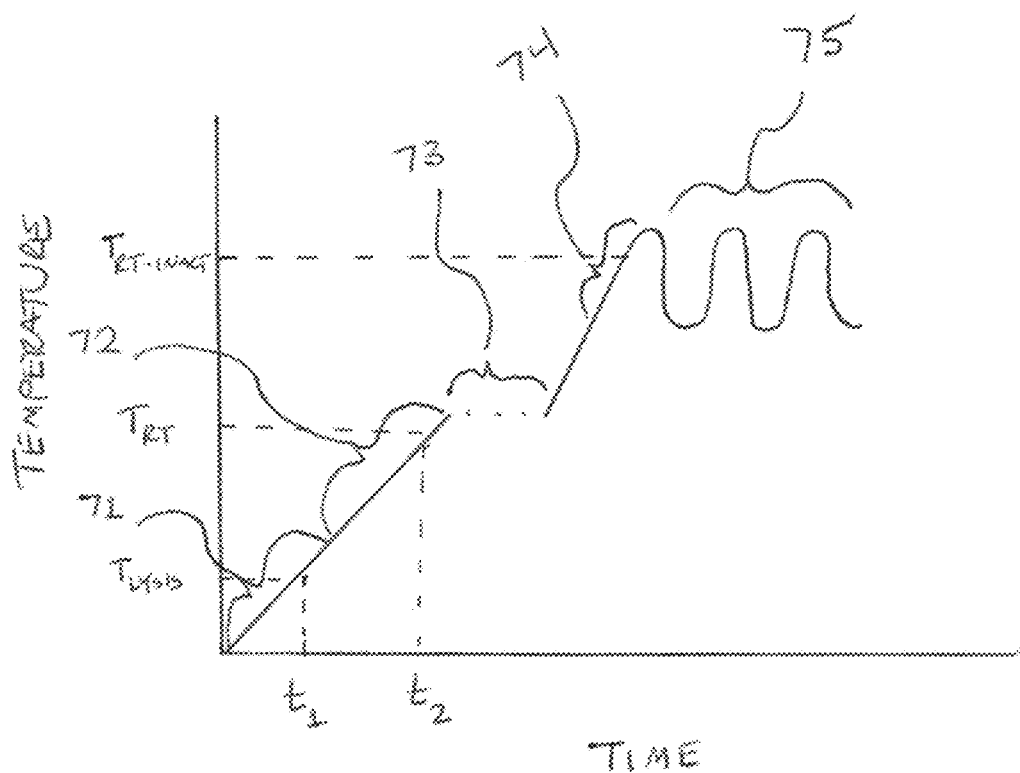

FIG. 17B shows a temperature/time performance chart of a method according to an embodiment. The RT-PCR method can be performed with any suitable device as described herein, and can include mixing, within a sample preparation module, a reverse transcriptase with a biological sample to form a reverse transcription solution. The sample preparation module can be a single environment or module, like the sample preparation module 6200 described below. In some embodiments, the reverse transcriptase can be a lyophilized or solid form reagent R4 that is captively maintained in a holding or mixing volume of the sample preparation module (e.g., the holding volume 6211). In some embodiments, the biological sample can be a raw and/or unfiltered sample. In some embodiments, the reverse transcription solution can be devoid of a ribonuclease inhibitor. Specifically, as described herein, the method can be performed in a manner such that the released RNA undergoes the reverse transcription rapidly so that degradation of the RNA by ribonuclease is limited.

The reverse transcription solution is then heated, within a reaction volume of the sample preparation module, to a first temperature within a lysing temperature range to release a ribonucleic acid (RNA) molecule. The lysing temperature range can be any of the ranges described herein. For example, in some embodiments, the first temperature range can be between about 25 C and about 40 C. Referring to FIG. 17B, in some embodiments, the heating to a first temperature can include heating the reverse transcription solution along a ramp rate, as shown by the region 71. Said another way, in some embodiments, the reverse transcription solution can be heated along a ramp from an initial temperature towards a reverse transcription temperature TRT, and need not be maintained at a constant lysing temperature for a set time period. In this manner, the solution can pass through a lysing temperature range (e.g., 25C to 35C) and/or a specific lysing temperature $T_{LYSIS}$ while being heated towards a target reverse transcription temperature.

The reverse transcription solution is then heated, within the reaction volume, to a second temperature within a reverse transcription temperature range to produce a complementary deoxyribonucleic acid (cDNA) molecule from the released RNA. The reverse transcription temperature range can be any of the ranges described herein. For example, in some embodiments, the first temperature range can be between about 40 C and about 60 C. In some embodiments, the heating can be performed by a segmented or "multi-zone" heater (e.g., the heater 6230) that conveys thermal energy into the initial volume 6211 of the sample preparation module. In other embodiments, the reverse transcription solution can be conveyed through a serpentine flow channel (e.g., the channel 6214) to facilitate heating by the heater 6230. Referring to FIG. 17B, in some embodiments, the reverse transcription solution can be continuously heated such that the temperature increases along a second ramp rate towards and/or through the reverse transcription temperature, as shown by the region 72, and need not be maintained at a constant reverse transcription temperature for a set time period.

In some embodiments, the heating to the first temperature and the heating to the second temperature are performed continuously such that the cDNA is produced within less than 1 minute of when the RNA molecule is released. In some embodiments, the heating to the first temperature and the heating to the second temperature are performed continuously such that the cDNA is produced within less than 30 seconds of when the RNA molecule is released.

In some embodiments, the solution can then be conveyed to a mixing module (e.g., the mixing assembly 6250) in which the DNA polymerase is mixed into the solution. This is shown by the region 73 in FIG. 17B. In some embodiments, the solution can then be conveyed to an amplification module (e.g., the amplification module 6600) in which the solution can be heated further to A) activate the DNA polymerase and B) deactivate the RT enzymes. This is shown by the region 74 in FIG. 17B. The solution can then undergo thermal cycling in accordance with the methods described herein, as shown by the region 75 in FIG. 17B.

Figure 17C:
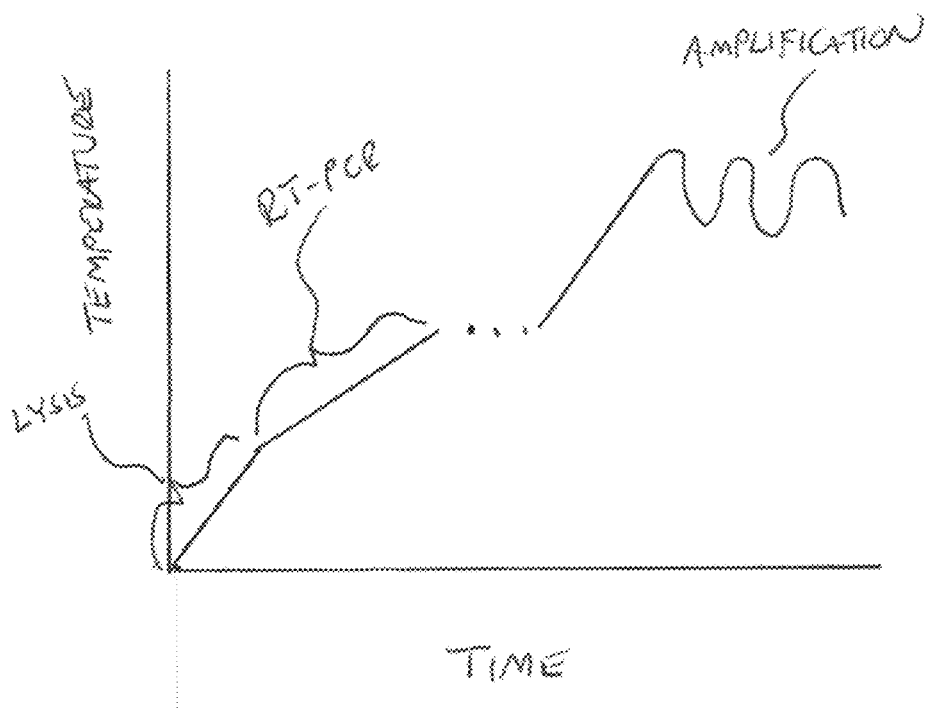

In some embodiments, the heating to the first temperature (for lysing) and the heating to the second temperature (for RT-PCR) can be performed at different ramp rates, as shown in FIG. 17C.

Figure 19:
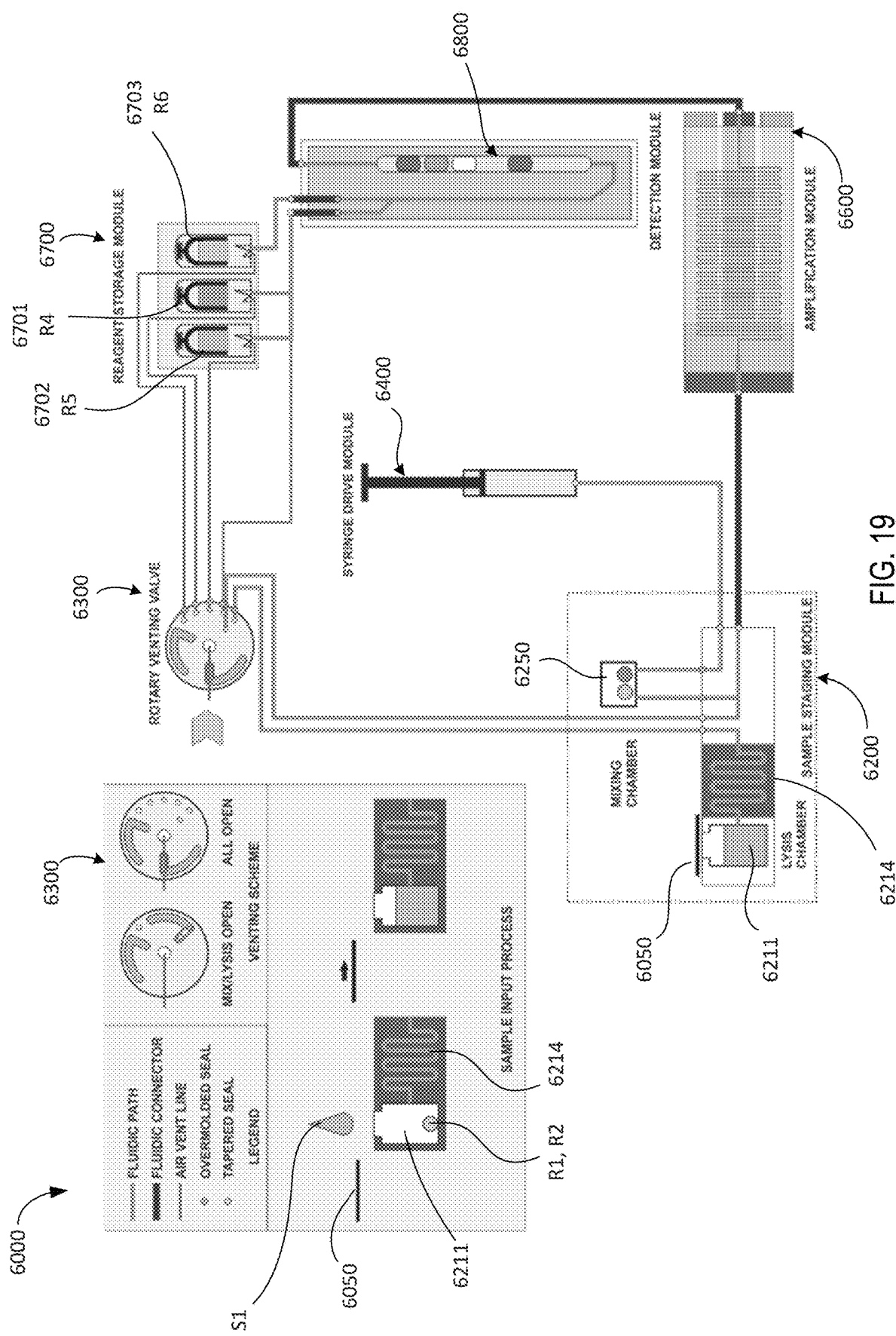
FIG. 19 is a schematic illustration of a molecular diagnostic test device, according to an embodiment.

FIG. 19 is a schematic illustration of a molecular diagnostic test device 6000, according to an embodiment. The schematic illustration describes the primary components of the test device 6000 as shown in FIGS. 20-52. The test device 6000 is an integrated device (i.e., the modules are contained within a single housing) that is suitable for use within a point-of-care setting (e.g., doctor's office, pharmacy or the like), decentralized test facility, or at the user's home. In some embodiments, the device 6000 can have a size, shape and/or weight such that the device 6000 can be carried, held, used and/or manipulated in a user's hands (i.e., it can be a "handheld" device). A handheld device may have dimensions less than 15 cm×15 cm×15 cm, or less than 15 cm×15 cm×10 cm, or less than 12 cm×12 cm×6 cm. In other embodiments, the test device 6000 can be a self-contained, single-use device. Similarly stated, the test device 6000 is a stand-alone device that includes all necessary substances, mechanisms, and subassemblies to perform any of the molecular diagnostic tests described herein. As such, the device 6000 does not require any external instrument to manipulate the biological samples, and only requires a connection to a power source (e.g., a connection to an A/C power source, coupling to a battery, or the like) to complete the methods described herein. In some embodiments, the test device 6000 can be configured with lock-outs or other mechanisms to prevent re-use or attempts to re-use the device.

Further, in some embodiments, the device 6000 can be a CLIA-waived device and/or can operate in accordance with methods that are CLIA waived. Similarly stated, in some embodiments, the device 6000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 6000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 6000 can be configured for long term storage in a manner that poses a limited likelihood of misuse (spoilage of the reagent(s), expiration of the reagents(s), leakage of the reagent(s), or the like). In some embodiments, the molecular diagnostic test device 6000 is configured to be stored for up to about 36 months, up to about 32 months, up to about 26 months, up to about 24 months, up to about 18 months, up to about 6 months, or any values there between.

The test device 6000 is configured to manipulate a biological sample S1 to produce one or more output signals associated with a target cell. Specifically, the device 6000 includes a sample preparation module 6200, a fluidic drive (or fluid transfer) module 6400, an amplification module 6600, a detection module 6800, a reagent module 6700, a valve 6300, and a control module (not shown). The test device and certain components therein can be similar to any of the molecular test devices shown and described herein or in International Patent Publication No. WO2016/109691, entitled "Devices and Methods for Molecular Diagnostic Testing," which is incorporated herein by reference in its entirety. Accordingly, a detailed description of certain modules (e.g., the fluidic drive module 6400) is not provided herein. A description of each of the modules is provided below.

FIGS. 20-53C show various views of the molecular diagnostic test device 6000. The test device 6000 is configured to manipulate an input sample to produce one or more output signals associated with a target cell, according to any of the methods described herein. The diagnostic test device 6000 includes a housing 6001 (including a top portion 6010 and a bottom portion 6030), within which the modules described herein are fully or partially contained. Similarly stated, the housing 6001 (including the top portion 6010 and/or the bottom portion 6030) at least partially surround and/or enclose the modules. FIGS. 22-25 are various views that show the sample preparation module 6200, the fluidic drive (or fluid transfer) module 6400, the amplification module 6600, the detection module 6800, the reagent module 6700, the fluid transfer valve 6300, and the electronic control module 6900 situated within the housing 6001. A description of the housing assembly 6001 if followed by a description of each module and/or subsystem.

The housing assembly 6001 includes a top housing 6010, a bottom housing 6030, and a lid 6050 (which functions as a cover and an actuator). As shown, the top housing 6010 defines a detection opening (or window) 6011 and a series of status light openings 6012. The top housing 6010 also includes a sample input portion 6020 and a label 6013. The status light openings 6012 are aligned with one or more light output devices (e.g., LEDs) of the electronic control module 6950. In this manner, a light output produced by such status lights is visible through the status light openings 6012. Such light outputs can indicate, for example, whether the device 6000 is receiving power from the power source, whether an error has occurred (e.g., an error associated with insufficient sample volume or the like), and whether the test has been successfully completed.

The detection opening (or window) is aligned with the detection module 6800. In this manner, the signal produced by and/or on each detection surface of the detection module 6800 is visible through the detection opening 6011. In some embodiments, the top housing 6010 and/or the label 6013 is opaque (or semi-opaque), thereby "framing" or accentuating the detection opening. In some embodiments, for example, the top housing 6010 can include markings (e.g., thick lines, colors or the like) to highlight the detection opening 6011. For example, in some embodiments, the top housing 6010 can include indicia 6014 identifying the detection opening to a specific disease (e.g., *Chlamydia trachomatis* (CT), *Neisseria gonorrhea* (NG) and *Trichomonas vaginalis* (TV)) or control. In other embodiments, the top housing 6010 need not include a detection opening 6011. For example, in such embodiments, the signal produced by the detection module 6800 is not visible to the naked eye, but instead is read using another method. For example, in some embodiments, the reading can include using a secondary device, such a mobile computing device to scan or otherwise receive the signal OP1. In yet other embodiments, the reading the result can include indirectly reading a secondary signal that conveys the results associated with (or describing) the primary output from the detection module 6800.

Figure 20:
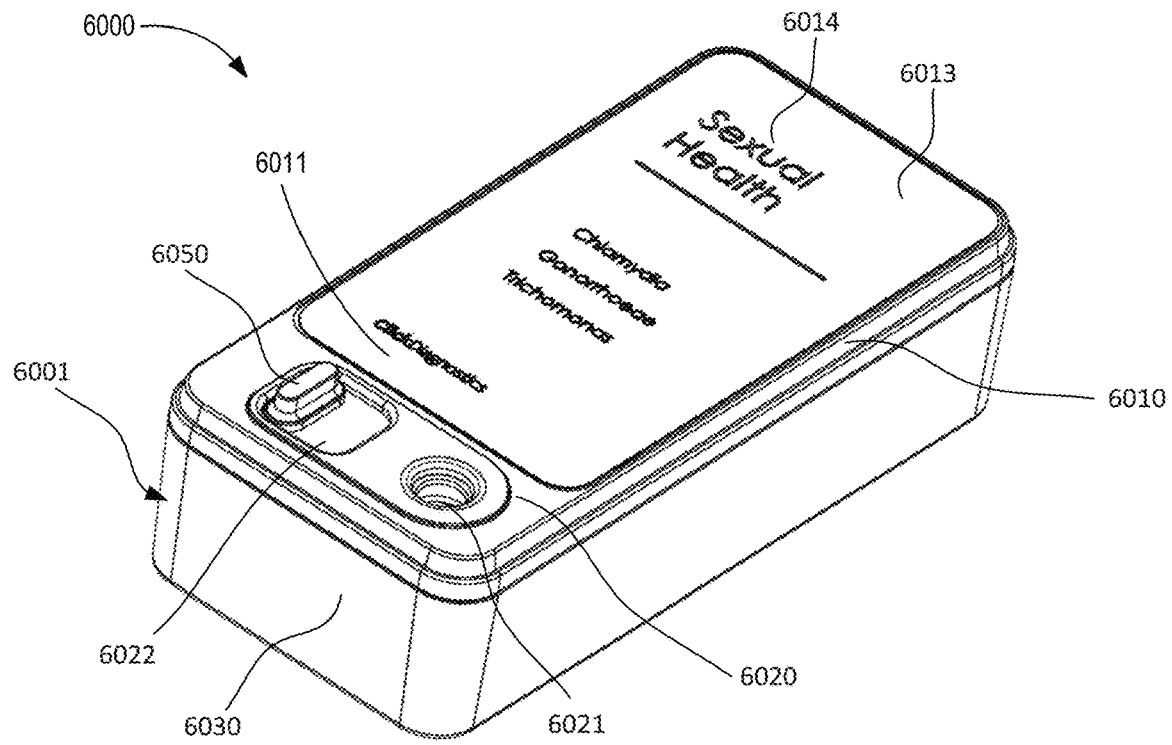
FIGS. 20 and 21 are a perspective view and a top view, respectively, of a molecular diagnostic test device, according to an embodiment.
Figure 21:
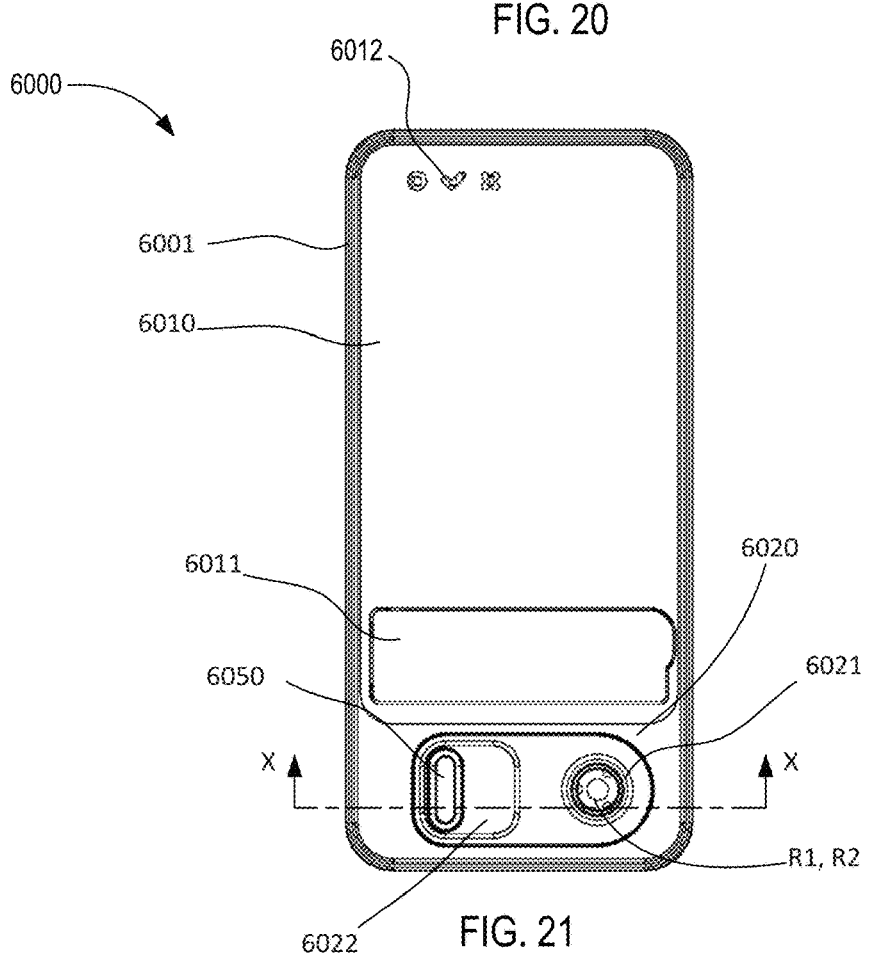
Figure 22:
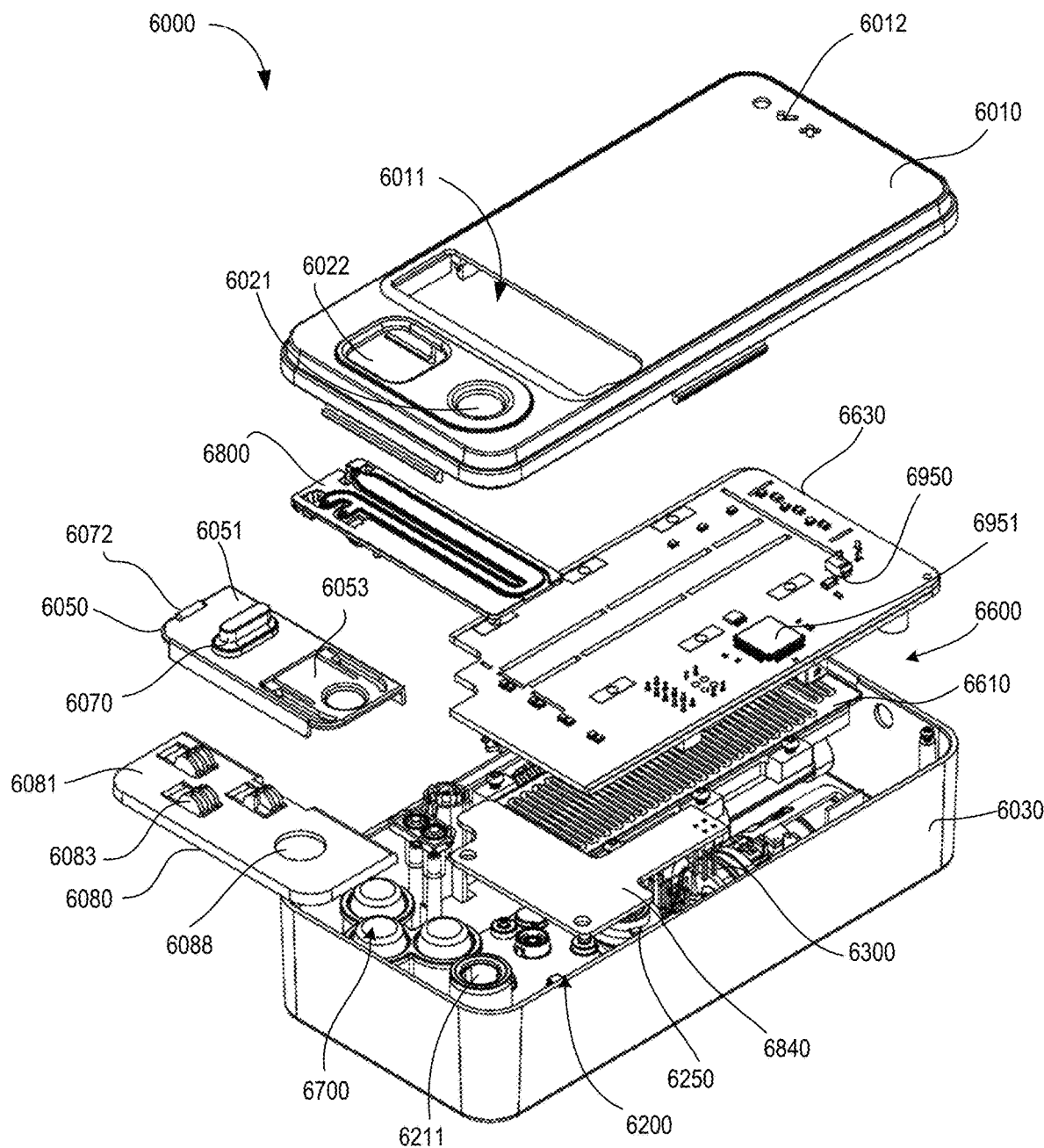
FIGS. 22 and 23 are exploded views of the molecular diagnostic test device shown in FIGS. 20 and 21.
Figure 23:
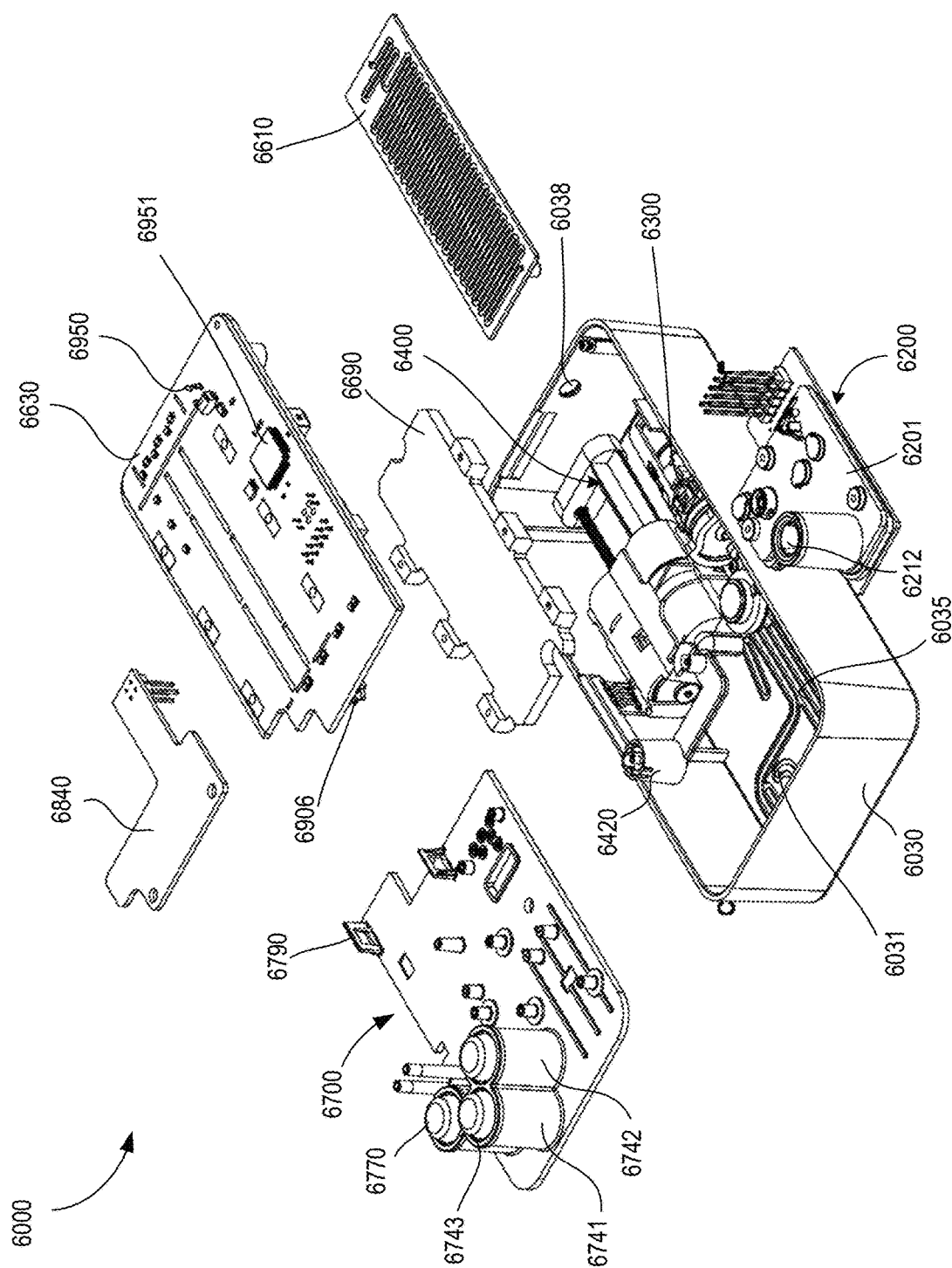
Figure 24:
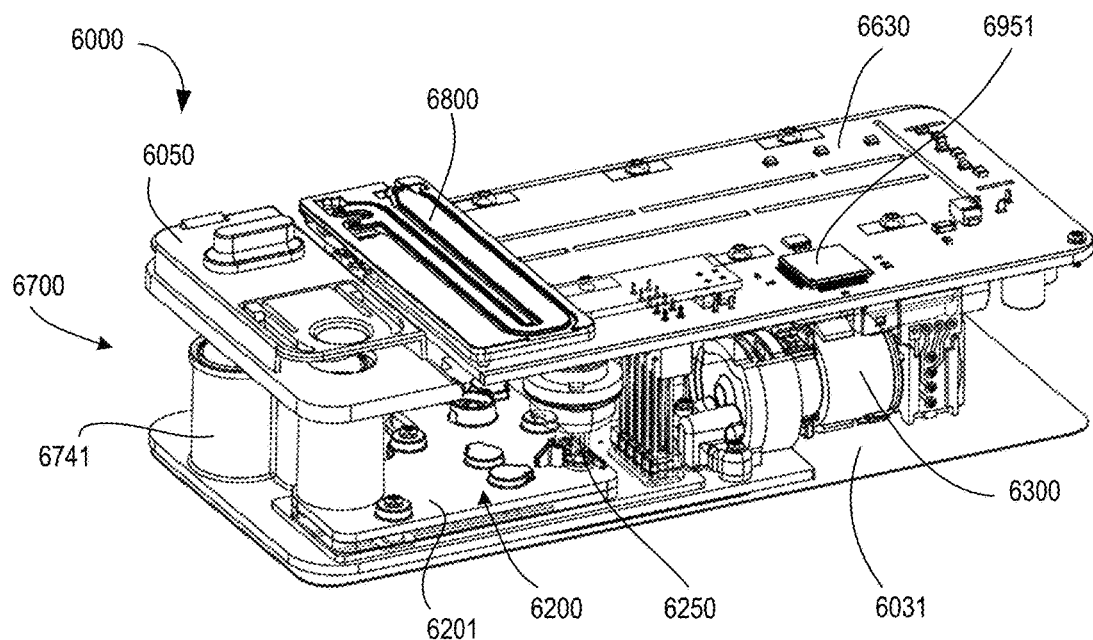
FIGS. 24 and 25 are a front perspective view (FIG. 24) and a rear perspective view (FIG. 25) of the molecular diagnostic test device shown in FIGS. 20 and 21, with the housing removed to show the modules therein.
Figure 25:
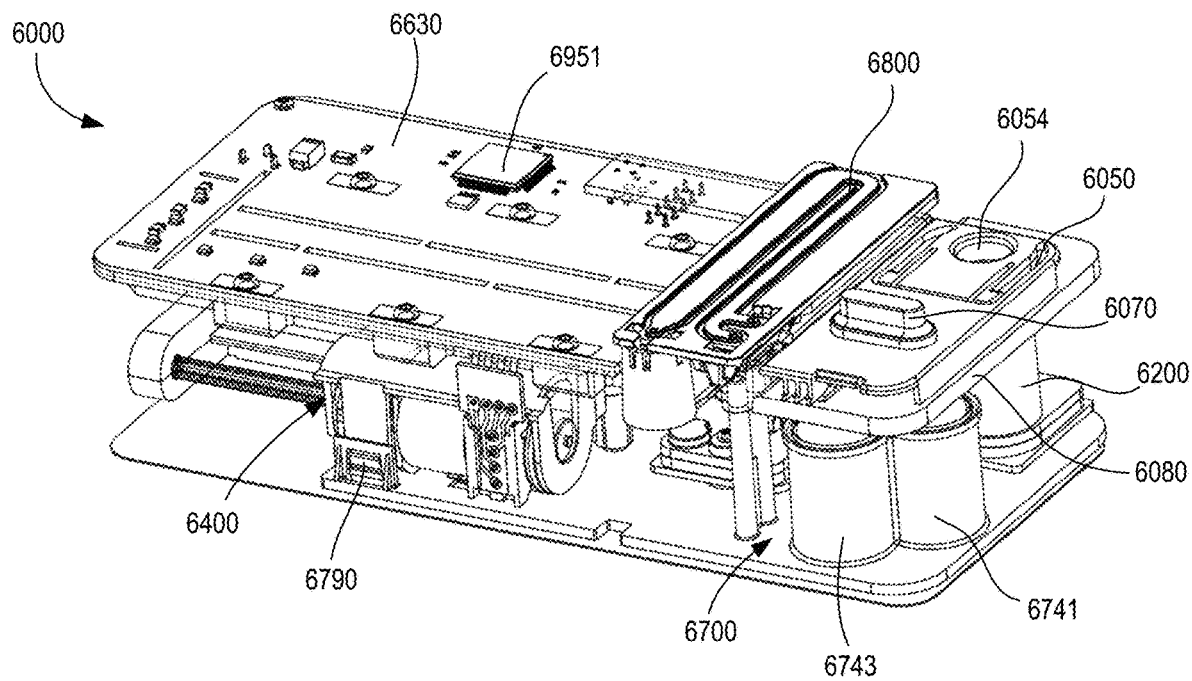
Figure 26:
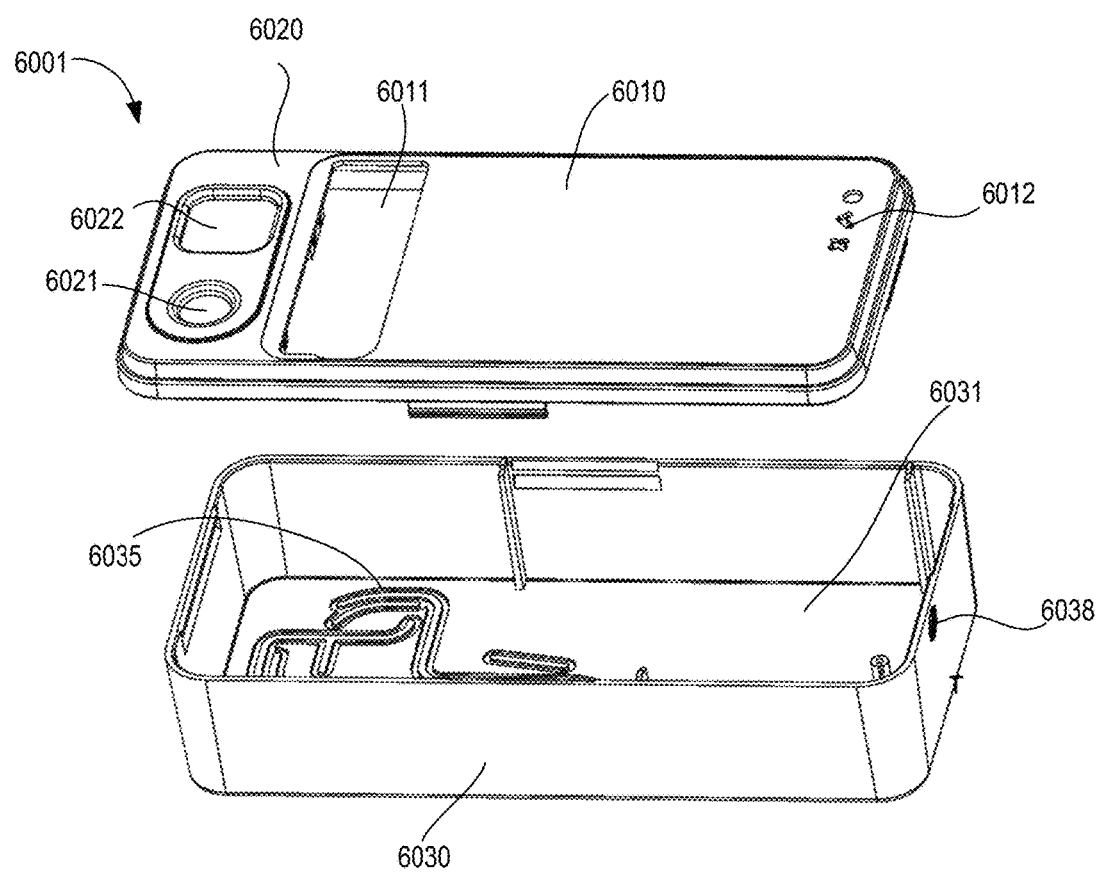
FIG. 26 is an exploded perspective view of the housing assembly of the molecular diagnostic test device shown in FIGS. 20 and 21.
Figure 27:
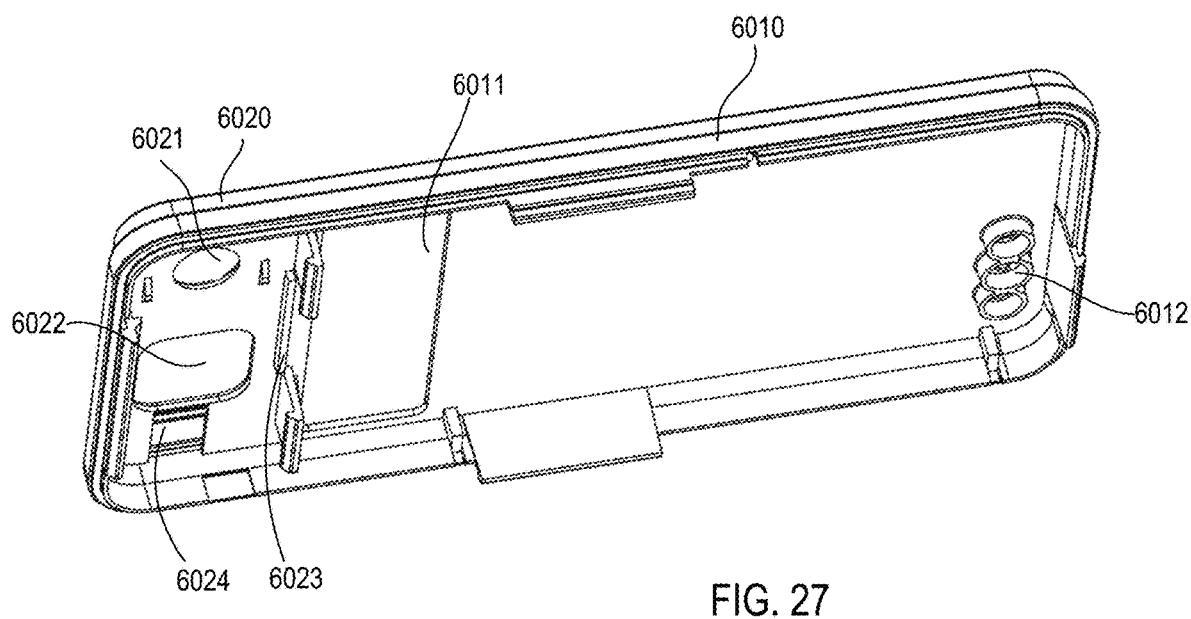
FIG. 27 is a bottom perspective view of the top housing of the molecular diagnostic test device shown in FIGS. 20 and 21.
Figure 33:
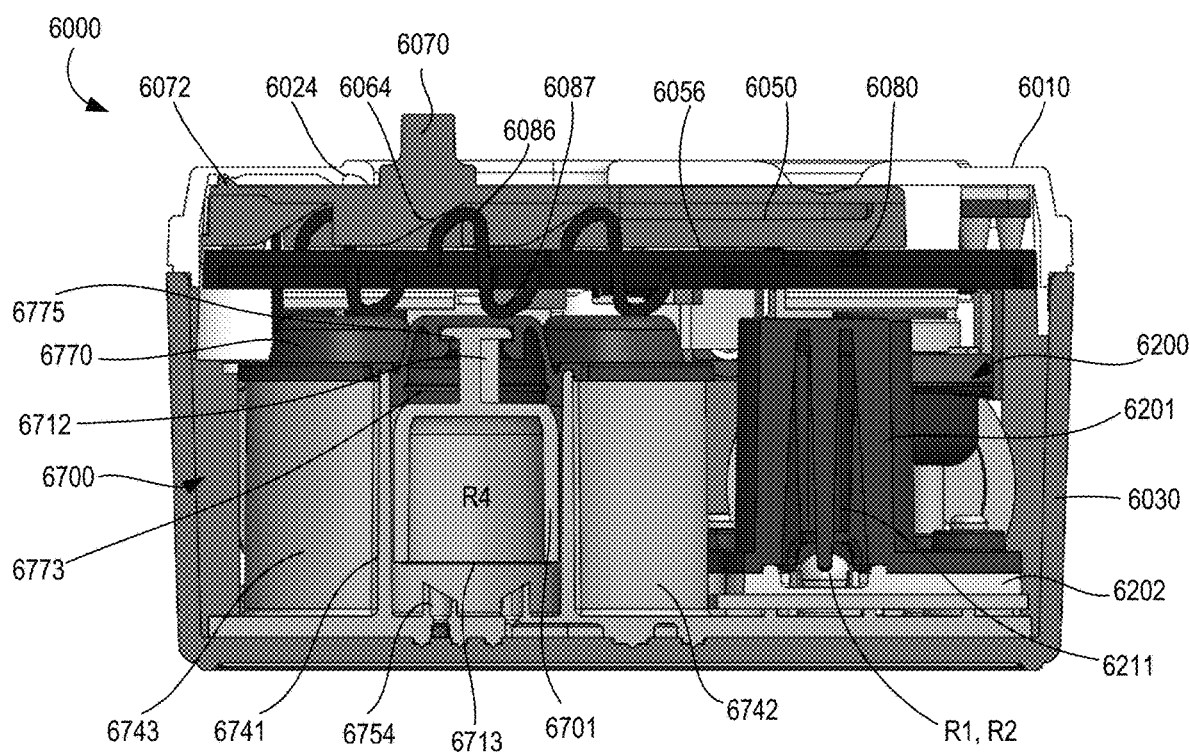
FIGS. 33 and 34 are side cross-sectional views taken along line X-X in FIG. 21, showing the molecular diagnostic test device in a first (pre-actuated) configuration and a second (post-actuated) configuration, respectively.
Figure 34:
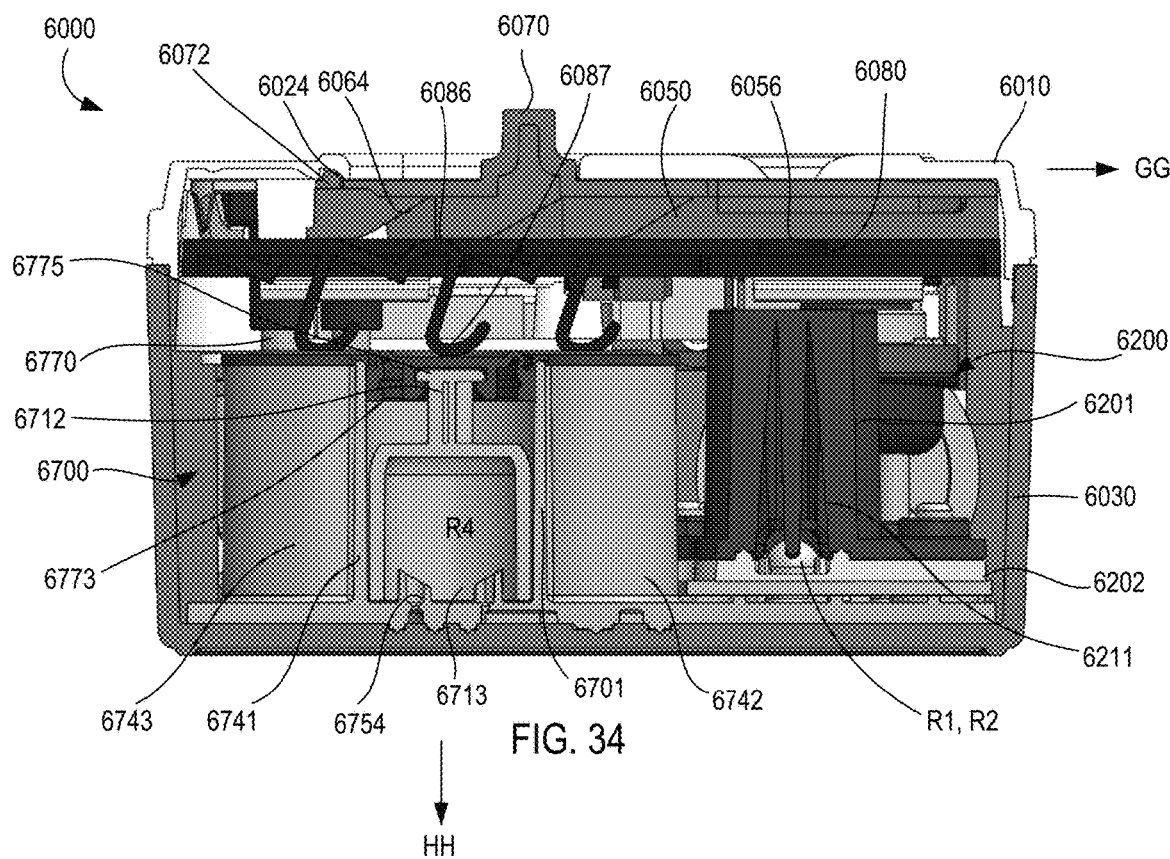

Referring to FIGS. 26 and 27, the sample input portion 6020 includes a set of guide rails 6023 and a lock recess 6024, both on the bottom (or inside) surface of the top housing 6010. The sample input portion 6020 also defines a sample input opening 6021 and an actuator opening 6022. The sample input opening 6021 is aligned with the input opening 6212 (of the sample preparation module 6200) and provides an opening through which a biological sample S1 can be conveyed into the device 6000. Additionally, the sample input portion also allows the lid (or actuator) 6050 to be movably coupled to the top housing 6010. Specifically, as shown in FIGS. 20, 33, and 34, the lid 6050 is coupled to the top housing 6010 such that the handle 6070 of the actuator extends through the actuator opening 6022. The actuator opening 6022 is elongated to allow for sliding movement of the lid 6050 relative to the top housing 6010, as described herein. Additionally, the guide rails 6023 are coupled to corresponding guide slots 6055 of the lid 6050 (see FIGS. 28 and 29) to facilitate the sliding movement of the lid 6050. As shown in FIGS. 33 and 34, the lock recess 6024 of the top housing 6010 is configured to receive the lock protrusion 6072 of the lid 6050 (see FIGS. 28 and 29) when the lid is in the second (or closed) position to prevent movement of the lid. In this manner, the top housing 6010 includes a lock mechanism that maintains the lid 6050 in its second (or closed) position to prevent reuse of the diagnostic device 6000, transfer of additional samples into the device 6000, or attempts to actuate the lid 6050 multiple times.

Figure 45:
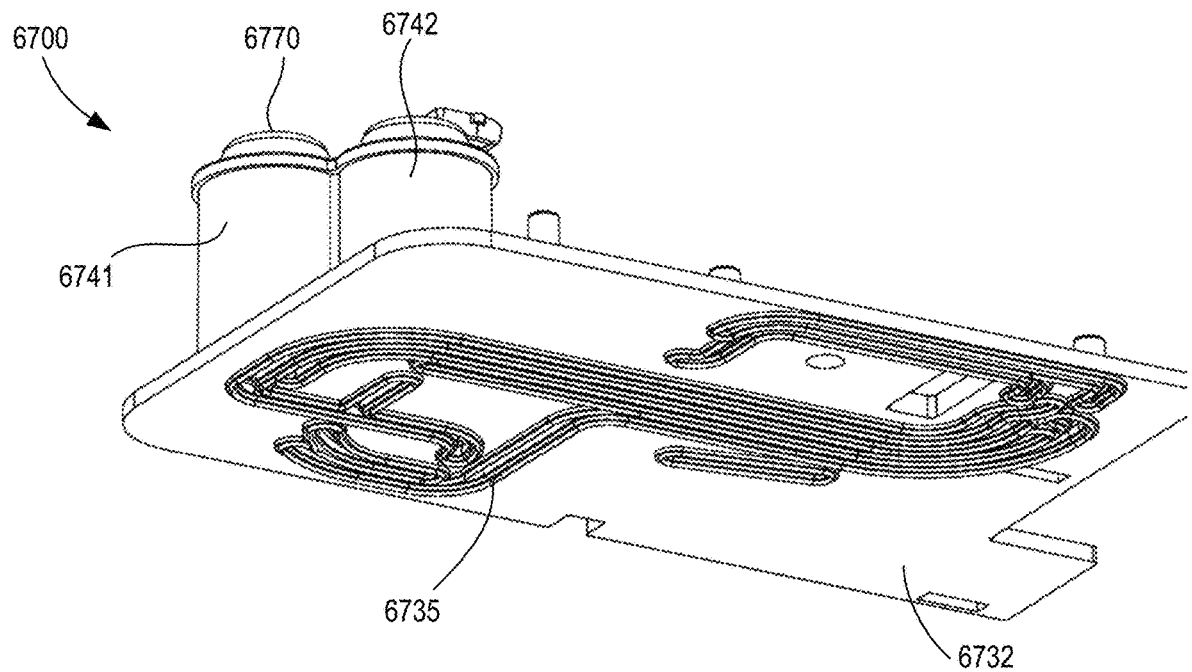
Figure 46:
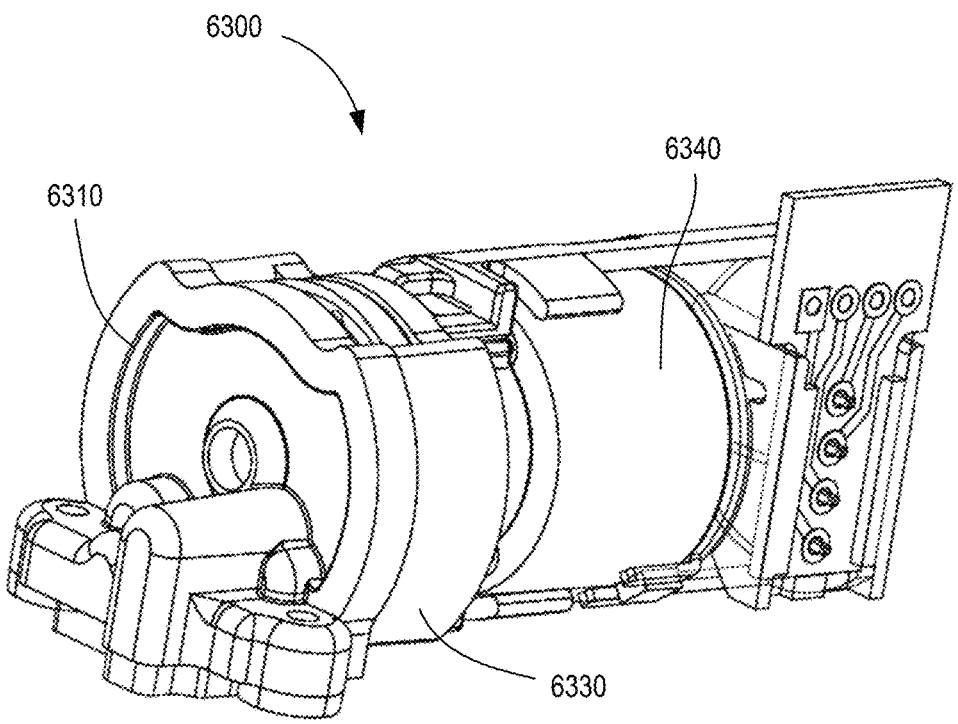
FIG. 46 is a front perspective view of rotary valve assembly of the molecular diagnostic test device shown in FIGS. 20 and 21.

The lower housing 6030 includes a bottom plate 6031 and defines a volume within which the modules and or components of the device 6000 are disposed. As shown in FIG. 26, the bottom plate 6031 defines a series of flow channels 6035 that are aligned with flow channels of other components within the device to allow for fluid transfer between the various modules and components without the need for tubing, clamps and the like. Specifically, as shown in FIG. 45, the bottom of the reagent module 6700 defines a series of flow channels 6735 that correspond to the flow channels 6035 in the bottom plate 6031 and thus facilitate transfer of fluids within the device. As shown in FIG. 26, the lower housing 6030 defines an opening 6038 that is aligned with a power input port of the electronic control module 6950. In use, an end of a power cord can be coupled to the electronic control module 6950 via the opening 6038 (see e.g., the coupling of the power cord 6905 in FIG. 53C).

Figure 28:
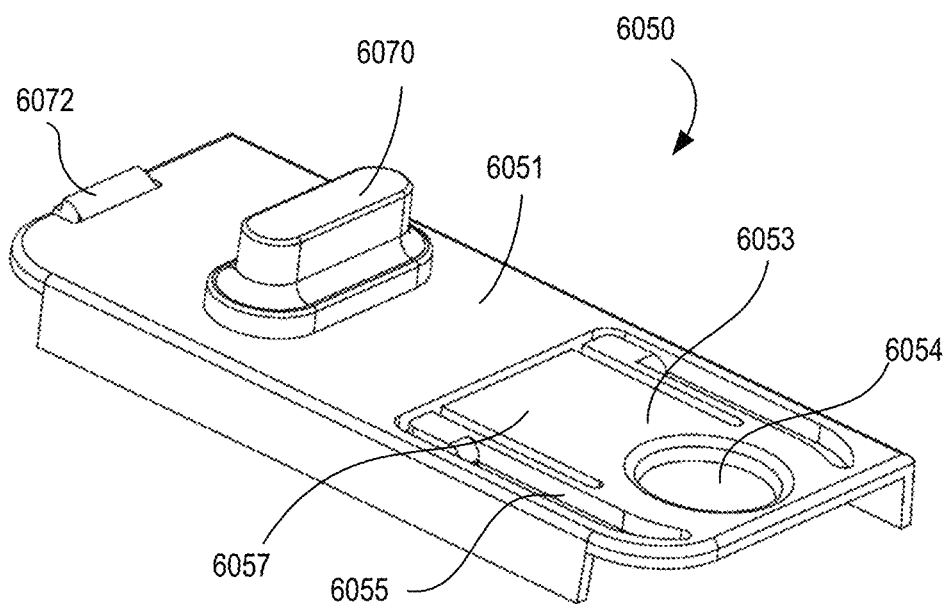
FIGS. 28-30 are a front perspective view (FIG. 28), a rear perspective view (FIG. 29), and a bottom perspective view (FIG. 30) of the lid of the molecular diagnostic test device shown in FIGS. 20 and 21.
Figure 29:
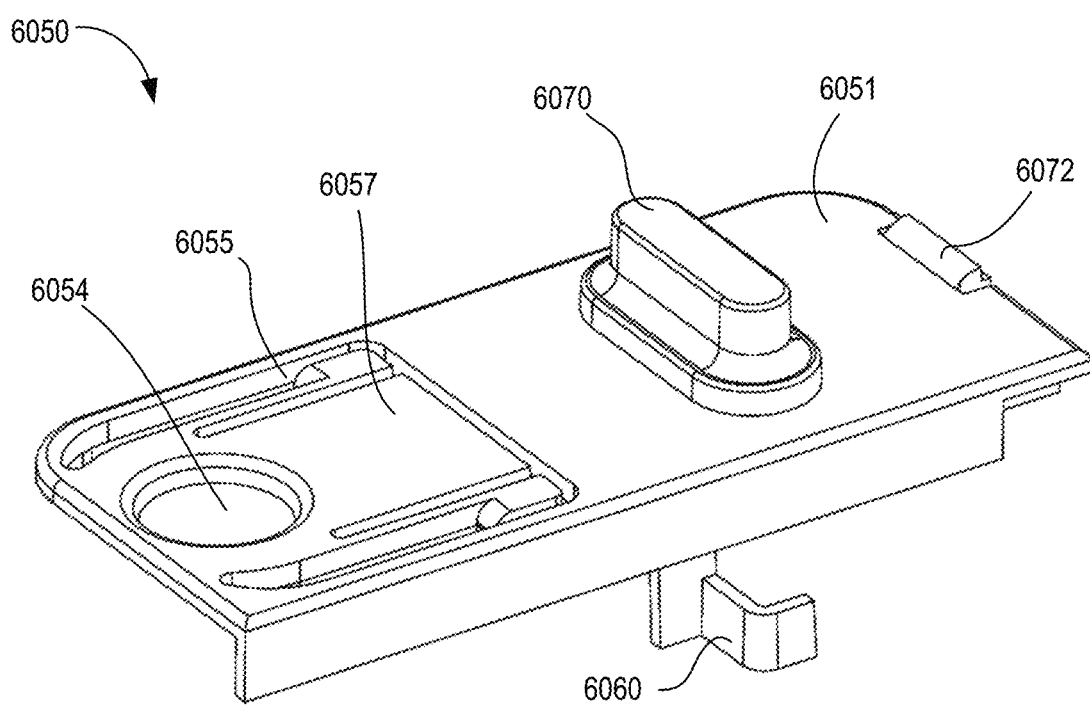
Figure 30:
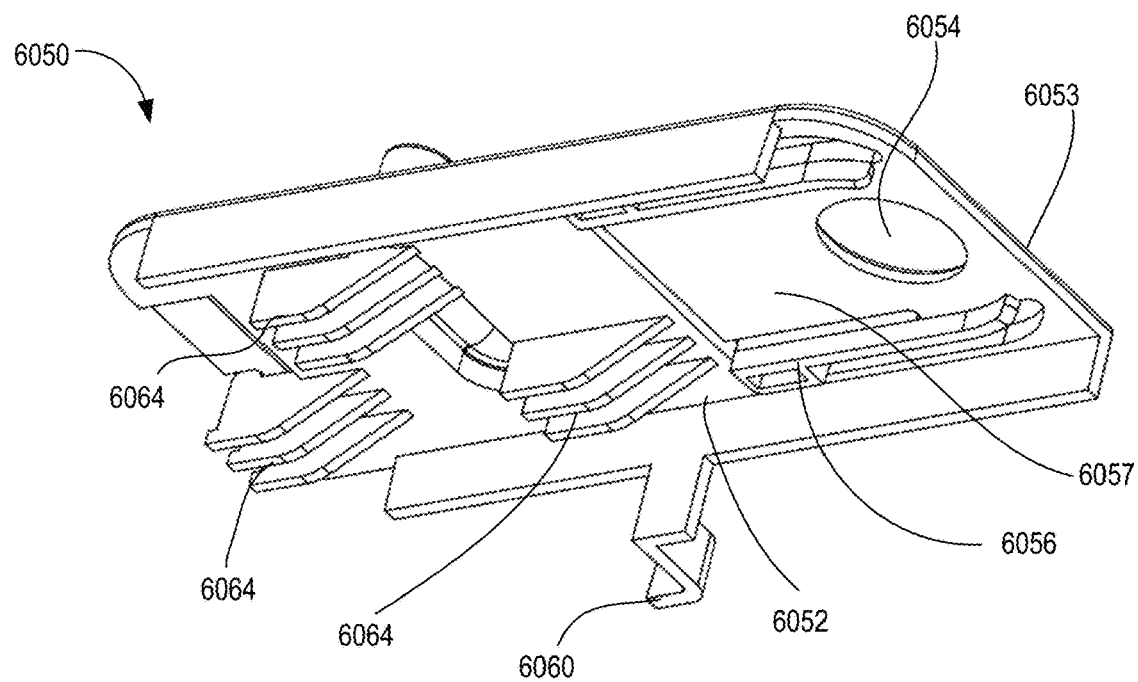

As shown in FIGS. 28-30, the lid 6050 includes a first (or outer) surface 6051 and a second (or inner) surface 6052. Referring to FIGS. 33 and 34, the lid 6050 is coupled to the housing 6001 and is positioned between the top housing 6010 and the flexible plate 6080. As described below, the lid 6050 and the flexible plate 6080 collectively actuate the reagent module 6700 when the lid 6050 is moved relative to the housing 6001. As shown in FIG. 30, the inner surface 6052 defines a pair of guide slots 6055 and includes a pair of guide rails 6056. As described above, the guide slots 6055 are coupled to corresponding guide rails 6023 of the housing 6001 to facilitate the sliding movement of the lid 6050. The guide rails 6056 of the lid 6050 are configured to engage with the flexible plate 6080, and thus also facilitate sliding movement of the lid 6050 (relative to the flexible plate 6080). As shown by the arrow GG in FIG. 34, the lid 6050 is configured to move relative to the housing 6001 from a first (or opened) position (FIG. 33) to a second (or closed) position (FIG. 34).

Similar to the lid 2050 described above, the lid 6050 is configured to perform a variety of functions when moved relative to the housing 6001, thereby facilitating actuation of the device 6000 via a single action. Specifically, the lid 6050 includes a seal portion 6053, a switch portion 6060, and three reagent actuators 6064. The seal portion 6053 (also referred to as a cover portion) includes a cover surface 6057 and defines an input opening 6054. When the lid 6050 is in the opened position (see e.g., FIGS. 20, 21, and 53A), the input opening 6054 is aligned with each of the sample input opening 6021 of the top housing 6010 and the input opening 6212 of the sample preparation module 6200 and thus provides an opening through which the biological sample S1 can be conveyed into the device 6000. The cover surface 6057 is a flat surface that covers (or obstructs each of the sample input opening 6021 of the top housing 6010 and the input opening 6212 when the lid is in the closed position (see FIGS. 53B and 53C). Specifically, the cover surface 6057 is spaced apart from the input opening 6212 and/or the sample input opening 6021 when the lid 6050 is in the opened position, but covers the input opening 6212 and/or the sample input opening 6021 when the lid 6050 is in the closed position. In some embodiments, the seal portion 6053 and/or the cover surface 6057 includes a seal, gasket, or other material to fluidically isolate the sample input volume 6211 (of the sample preparation module 6200) when the lid 6050 is in the closed position.

In addition to covering the input opening 6212, closing the lid 6050 also actuates other mechanisms within the device 6000. Specifically, as shown in FIGS. 29 and 30, the switch portion 6060 includes a protrusion that actuates the switch 6906 (FIG. 23) when the lid 6050 is moved from the opened position to the closed position. When the switch is actuated (i.e., is moved from a first state to a second state), power from the power source (e.g., the power source 6905) can be provided to the electronic control module 6950 and any other components within the device 6000 that require power for operation. For example, in some embodiments, power is provided to any of the heaters (e.g., the heater 6230 of the sample preparation module 6200, the heater 6630 of the amplification module 6600, and the heater 6840 of the detection module 6800) directly or via the electronic control module 6950. For example, this allows the heater 6230 to begin preheating for a lysis operation after the lid 6050 is closed and the device 6050 is coupled to the power source 6905 without requiring further user action. Although the switch 6906 is shown as being a rocker switch that is actuated directly by the protrusion of the switch portion 6060, in other embodiments, the switch 6906 (and the corresponding switch portion 6060) can be any suitable switch that performs the functions described herein. For example, in some embodiments, the switch can be an isolation member that electrically isolates the power source 6905 from the remaining components of the electronic control module 6950. In such embodiments, the switch portion 6060 can be coupled to, and can remove, the isolation member (thereby electrically coupling the power source 6905 to the electronic control module 6950). In other embodiment, the switch portion 6060 is the isolation member, and no separate switch is included in the electronic control module 6950.

Figure 31:
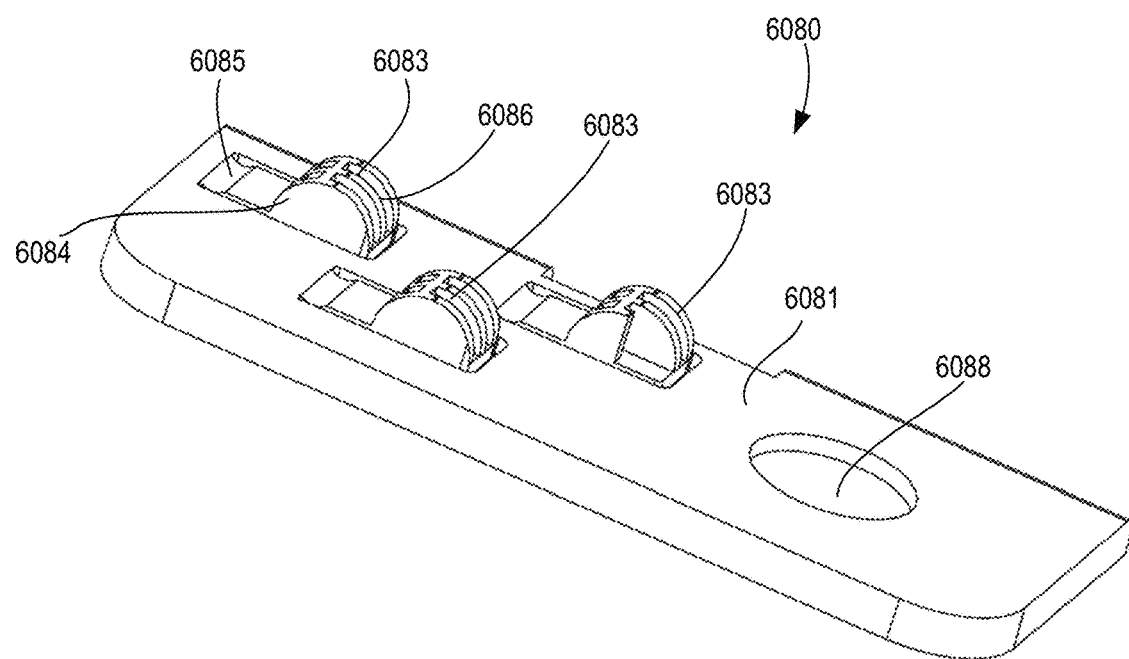
FIGS. 31 and 32 are a top perspective view (FIG. 31) and a bottom perspective view (FIG. 32) of the flexible plate of the molecular diagnostic test device shown in FIGS. 20 and 21.
Figure 32:
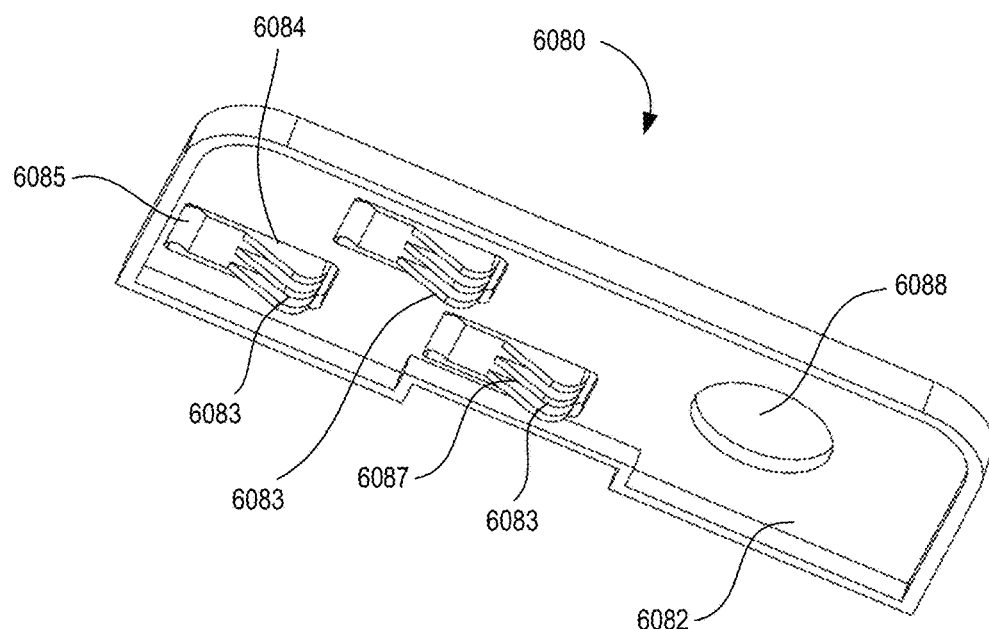

Referring to FIGS. 30 and 31, the reagent actuators 6064 include a series of ramped surfaces that exert an actuation force on a corresponding set of deformable actuators 6083 of the flexible plate 6080 when the lid 6050 is moved from the opened position (FIG. 33) to the closed position (FIG. 34). In this manner, the reagent actuators 6064 (and the deformable actuators 6083 of the flexible plate 6080) cause the reagent to be released from the sealed reagent containers within the reagent module 6700, as described in more detail below.

The outer surface 6051 of the lid 6050 includes a handle 6070 and a lock protrusion 6072. The handle 6070 extends through the actuator opening 6022 of the top housing 6010 and provides a structure that can be manipulated by the user to move the lid 6050 from the opened position to the closed position. The lock protrusion 6072 has a ramped (or angled) protrusion that is maintained in sliding contact with the inner surface of the top housing 6010 (see the inner surface shown in FIG. 27). Because the ramped surface of the lock protrusion 6072 forms an acute angle, the lock protrusion can be moved in the direction shown by the arrow GG in FIG. 34 to close the lid 6050. Additionally, the continuous contact between the lock protrusion 6072 and the top housing 6010 prevents inadvertent closure of the lid 6050 by providing some resistance (i.e., a friction force) to closing the lid. As shown in FIG. 34, when the lid 6050 is in the closed position, lock protrusion 6072 is received within the lock recess 6024 of the top housing 6010. The surface of the lock protrusion 6072 opposite the ramped surface forms a substantially 90-degree angle and thus prevents movement of the lid 6050 in the opposite direction when the lock protrusion 6072 is within the recess 6024. In this manner, the lid 6050 is irreversibly locked after being closed to prevent reuse of the device 6000 and/or the addition of supplemental sample fluids.

The flexible plate 6080 (shown in FIGS. 31 and 32) includes an outer surface 6081 and an inner surface 6082. As described above, the lid 6050 is movably disposed between the top housing 6010 and the flexible plate 6080. Similarly stated, the outer surface 6051 of the lid 6050 faces the inner surface of the top housing 6010 and the inner surface 6052 of the lid 6050 faces the outer surface 6081 of the flexible plate 6080. The flexible plate includes three deformable actuators 6083, each of which is aligned with a corresponding reagent actuator 6064 of the lid 6050 and one of the reagent containers 6701, 6702, 6703. Thus, when the lid 6050 is moved relative to the housing 6001, the reagent actuators 6064 and the deformable actuators 6083 actuate the reagent module 6700. In particular, as described in detail below, the reagent actuators 6064 and the deformable actuators 6083 move the reagent containers 6701, 6702, 6703 within the reagent manifold 6730 to release the reagents that are sealed within the containers.

The flexible plate 6080 defines a channel 6084 for the surrounds at least three sides of each of the deformable actuators 6083. Thus, each of the deformable actuators 6083 remains coupled to the flexible plate 6080 by a small strip of material (or living hinge) 6085. Accordingly, when the reagent actuator 6064 exerts an inward force on the outer surface 6086 of deformable actuator 6083, the deformable actuator bends or deforms inwardly towards the reagent module 6700 as shown by the arrow HH in FIG. 34. This action causes the inner surface 6087 of each of the deformable actuators 6083 to apply an inward force on the reagent containers (and the deformable support member 6770 thereby moving the reagent containers downward within the reagent manifold 6730, as shown by the arrow HH in FIG. 34.

Figure 35:
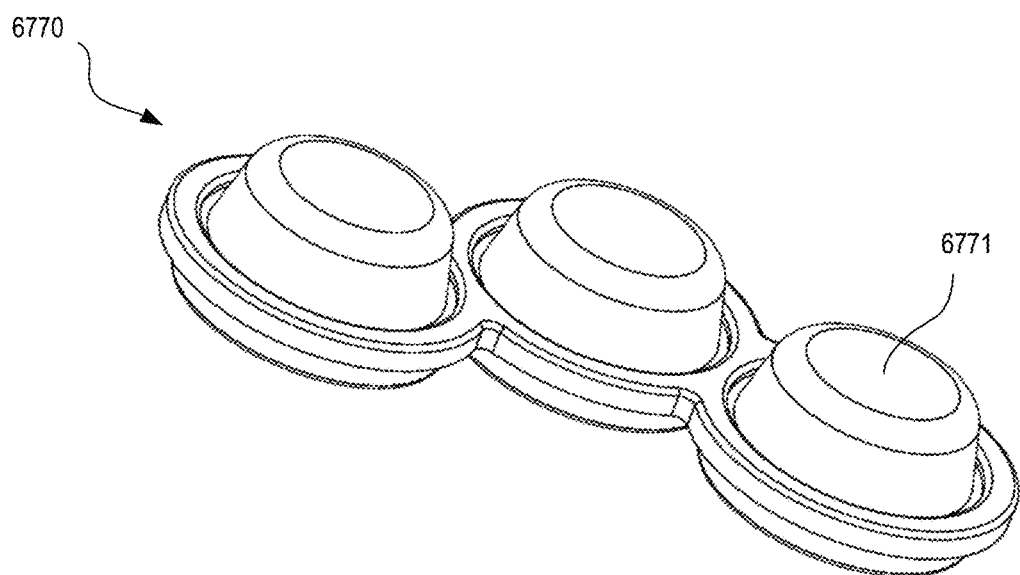
FIGS. 35 and 36 are a top perspective view (FIG. 35) and a bottom perspective view (FIG. 36) of the deformable support member of the molecular diagnostic test device shown in FIGS. 20 and 21.
Figure 36:
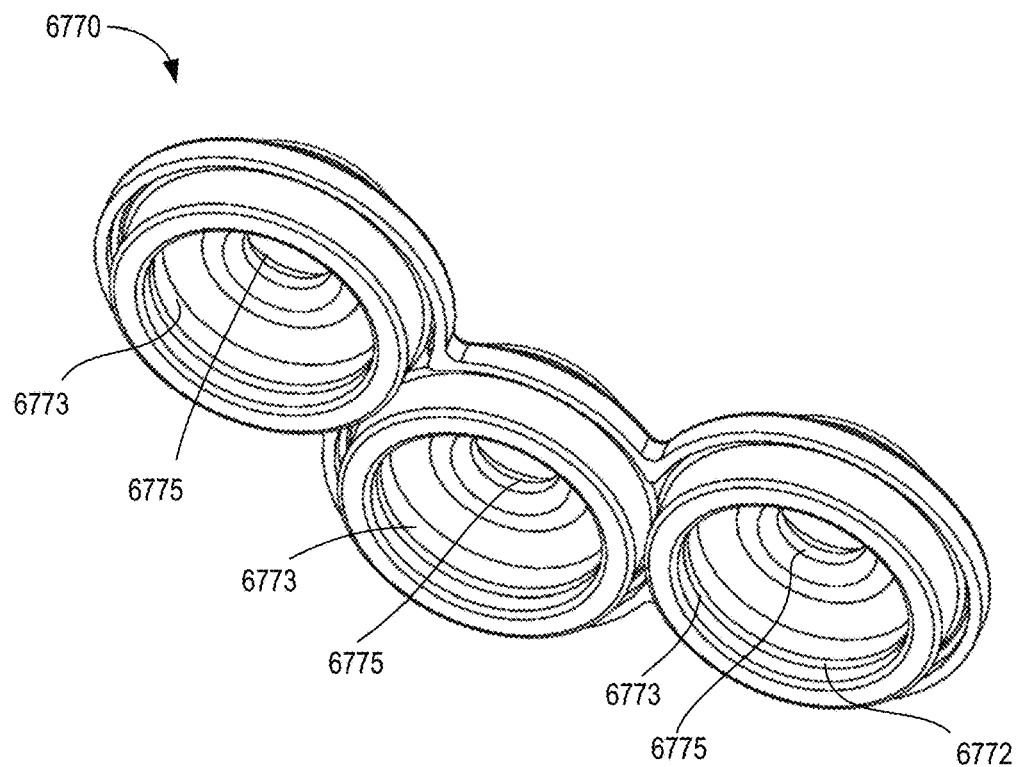
Figure 37:
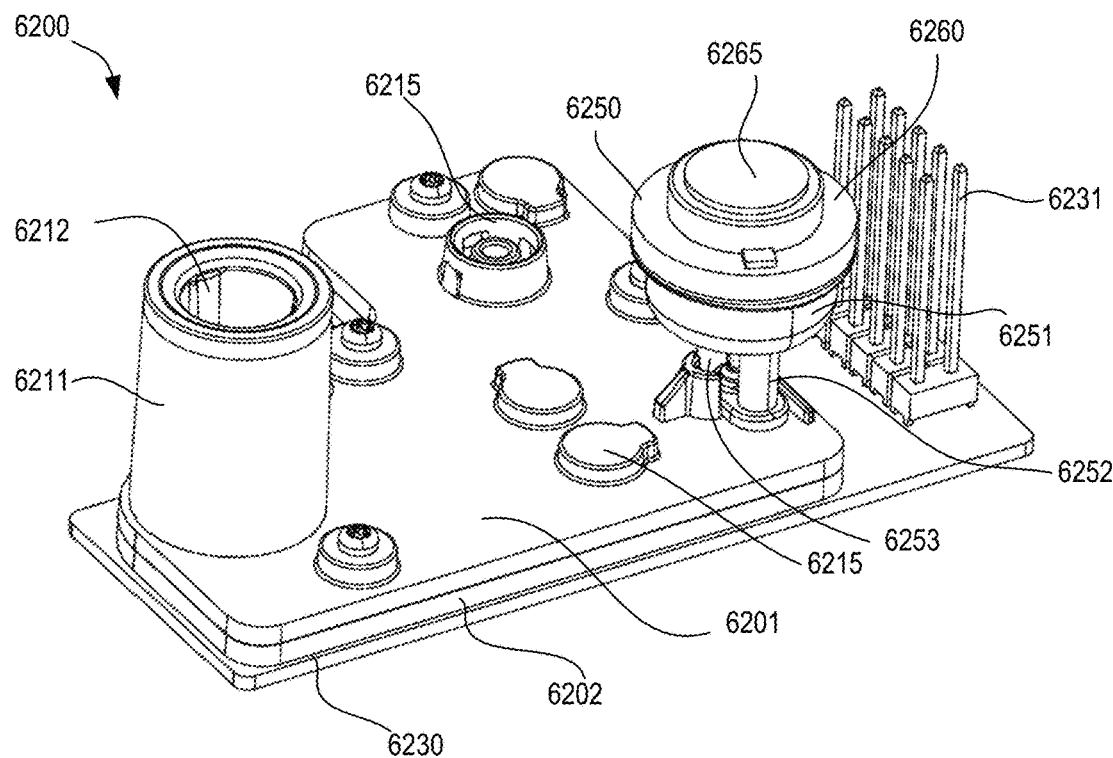
FIGS. 37 and 38 are a perspective view (FIG. 37) and a top view (FIG. 38) of the sample preparation (or staging) module of the molecular diagnostic test device shown in FIGS. 20 and 21.

Referring to FIGS. 33, 34, 44, and 45, the reagent module 6700 includes a reagent manifold (or housing) 6730, three reagent containers 6701, 6702, 6703, and a deformable support member 6770 (see FIGS. 35 and 36). The reagent module 6700 provides mechanisms for long-term storage of reagents within the sealed reagent containers, actuation of the reagent containers to release the reagents from the reagent containers for use during the methods described herein. In addition to providing storage and actuating functions, the reagent module 6700 also provides fluid interconnections to allow the reagents and/or other fluids to be conveyed within the device 6000. Specifically, as described herein, the reagent module 6700 is fluidically coupled to the fluid transfer valve 6300 in a manner that allows selective venting, fluid coupling, and/or conveyance of the reagents and substances within the device 6000.

The reagent module 6700 stores packaged reagents, identified herein as reagent R4 (a dual-purpose blocking and wash solution), reagent R5 (an enzyme reagent), and reagent R6 (a substrate), and allows for easy un-packaging and use of these reagents in the detection module 6800. As shown schematically in FIG. 19, the reagent module 6700 includes a first reagent container 6701 (containing the reagent R4), a second reagent container 6702 (containing the reagent R5), and a third reagent container 6703 (containing the reagent R6). Each of the reagent containers includes a connector at a first end portion and a frangible seal at a second, opposite end portion. Specifically, as shown in FIGS. 33 and 34, the first reagent container 6701 includes a connector 6712 and a frangible seal 6713. The connector 6712 connects the first reagent container 6701 to the mating coupling portion 6775 of the deformable support member 6770. The frangible seal 6713 is any suitable seal, such as, for example, a heat-sealed BOPP film (or any other suitable thermoplastic film). Such films have excellent barrier properties, which prevent interaction between the fluids within the reagent container and external humidity, but also have weak structural properties, allowing the films to be easily broken when needed. When the reagent container is pushed into the puncturers, as described below, the frangible seal breaks, allowing the liquid reagent to flow into the appropriate reagent reservoir when vented by the fluid transfer valve 6300. Although only the details of the first reagent container 6701 are shown and described herein, the second reagent container 6702 and the third reagent container 6703 have similar structure and function.

Figure 44:
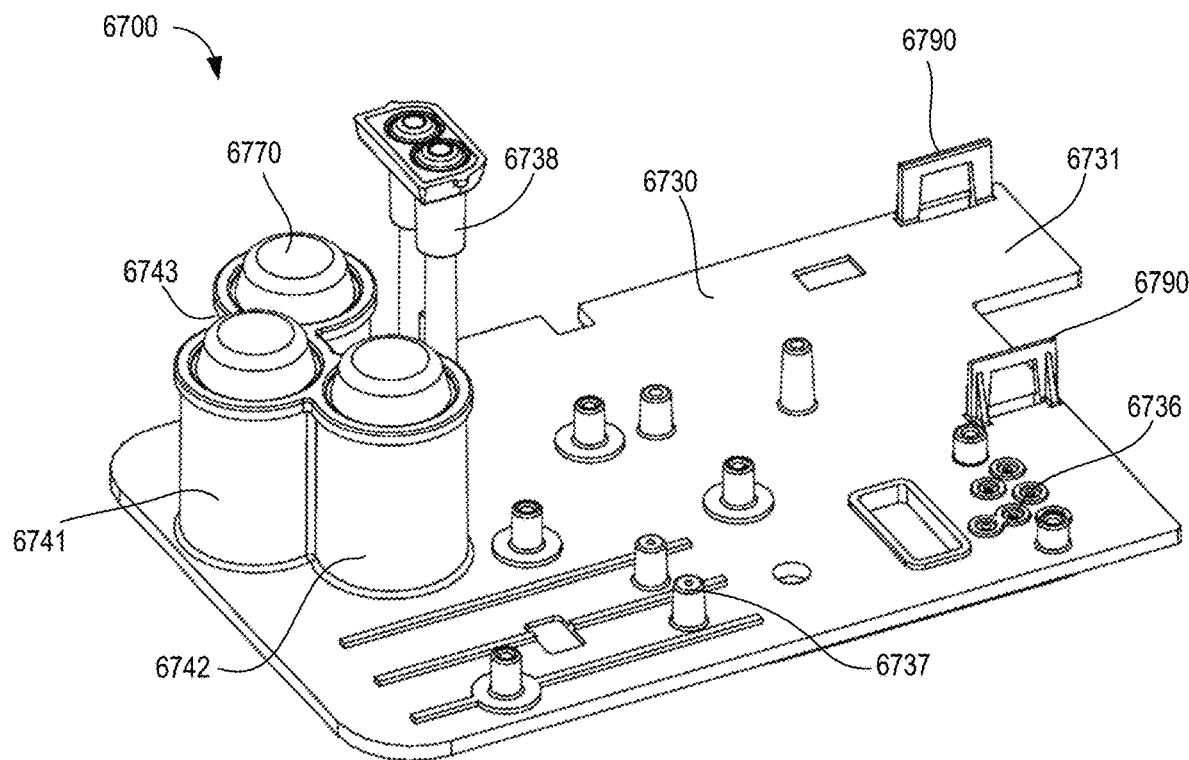
FIGS. 44 and 45 are a top perspective view (FIG. 44) and a bottom perspective view (FIG. 45) of the reagent module of the molecular diagnostic test device shown in FIGS. 20 and 21.

Referring to FIGS. 44 and 45, the reagent manifold 6730 includes a top (or outer) surface 6731 and a bottom (or inner) surface 6732. The reagent manifold 6730 includes three reagent tanks extending from the top surface 6731 and within which the reagent containers are disposed. Specifically, the reagent manifold includes a first reagent tank 6741 within which the first reagent container 6701 is disposed, a second reagent tank 6742 within which the second reagent container 6702 is disposed, and a third reagent tank 6743 within which the third reagent container 6703 is disposed. The reagent housing 6730 includes a pair of puncturers in the bottom portion of each reagent tank. The puncturers are configured to pierce the frangible seal of the respective reagent container when the reagent container is moved downward within the reagent housing 6730. Similarly stated, the reagent housing 6730 includes a set of puncturers that pierce a corresponding frangible seal to open a corresponding reagent container when the reagent module 6700 is actuated. Referring to FIGS. 33 and 34 as an example, the reagent housing 6730 includes a set of puncturers 6754 within the first reagent tank 6741. The reagent housing 6730 includes similar puncturers in the second reagent tank 6742 and the third reagent tank 6743. Further, the puncturers define a flow path that places the internal volume of the reagent container and/or the reagent tank in fluid communication with an outlet port of the reagent module 6700 after the frangible seal is punctured.

The deformable support member 6770 includes an outer surface 6771 and an inner surface 6772. As described above, the outer surface 6771 includes actuation regions that are aligned with one of the deformable actuators 6083 of the flexible plate 6080. The inner surface 6772 includes three seal portions 6773 and three coupling portions 6775. As shown in FIGS. 33 and 34, each of the seal portion 6773 is coupled to the reagent housing 6730 to fluidically isolate the internal volume (i.e., the reagent reservoir) of the corresponding reagent tank. The coupling portions 6775 are each coupled to one of the connectors of the corresponding reagent container. As an example, one of the seal portions 6773 is coupled to the top portion of the first reagent tank 6741 to fluidically isolate (or seal) the internal volume of the first reagent tank 6741. Additionally, one of the coupling portions 6775 is coupled to the connector 6712 of the first reagent container 6701.

The deformable support member 6770 is configured to deform from a first configuration (FIG. 33) to a second configuration (FIG. 34) in response to an actuation force exerted thereon (e.g., by the deformable actuator 6083). Moreover, the deformable support member 6770 is biased in the first (or undeformed) configuration. In this manner, the deformable support member 6770 supports each of the reagent containers in a "storage state" when the deformable support member 6770 is in the first configuration. Similarly stated, the deformable support member 6770 maintains the puncturer 6754 spaced apart from the frangible seal 6713 of the reagent container 6701 when the deformable support member is in the first configuration.

When the lid 6050 is moved, the downward force exerted by the deformable actuators 6083 cause the deformable support member 6770 to transition to the second (or deformed) configuration (FIG. 34). Similarly stated, when the downward force is sufficient to overcome the opposite, biasing force of the deformable support member 6770, the deformable support member 6770 is transitioned to the second configuration, as shown by the arrow HH in FIG. 34. This causes each of the reagent containers to move downward within the corresponding reagent tank, bringing the puncturers into contact with the frangible seal of each reagent container. Similarly stated, when the deformable support member 6770 is in the second configuration, the puncturers 6754 pierce the frangible seal 6713 of the reagent container 6701, thereby release the reagent R4 from within the reagent container 6701. Although FIG. 34 shows the actuation for only the first reagent container 6701, when the reagent module 6700 is actuated, each of the first reagent container 6701, the second reagent container 6702, and the third reagent container 6703 are actuated in this manner. Thus, in addition to covering the sample input opening and providing power to the electronic control module 6950, closing the lid 6050 also actuates all of the reagent containers.

Although shown as including three reagent containers, in other embodiments, the reagent module 6700 (or any of the reagent modules described herein) can have any suitable number of reagent containers. For example, in some embodiments, a reagent module can include only one reagent container, similar the reagent module 2700 described herein.

Referring to FIG. 44, the outer surface 6731 of the reagent manifold 6730 includes a set of valve fluid interconnects 6736, a set of mixing chamber fluid interconnects 6737, and a set of detection module fluid interconnects 6738. Each of these fluid interconnects is coupled to one of the reagent tanks and/or other components within the device 6000 by the flow channels 6735 defined in the inner surface 6732. Additionally, the outer surface 6731 includes multiple mounting clips 6790. Thus, the valve fluid interconnects 6736 (and the appropriate channels 6735) provide fluidic coupling to the fluid transfer valve 6300, which is coupled to the top surface 6731 by one of the clips 6790. The mixing chamber fluid interconnects 6737 (and the appropriate channels 6735) provide fluidic coupling to the mixing assembly 6250, which is coupled to the top surface 6731. The detection module fluid interconnects 6738 (and the appropriate channels 6735) provide fluidic coupling to the detection module 6800.

FIGS. 37-41 show various views of the sample preparation module 6200. As described herein, the sample preparation (or staging) module 6200 can perform any or all of A) receiving the biological sample S1, B) mixing the biological sample with desired reagents (e.g., a positive control reagent R1 and a reverse transcriptase R2), C) performing lysing operations to release target RNA from the biological sample S1, D) performing a reverse transcription reaction to produce cDNA, and E) heating the resulting solution to inactivate the reverse transcriptase. Thus, in some embodiments, the sample preparation module enables an efficient, fast RT-PCR to be performed within a single environment or module. By eliminating the need for external sample preparation and a cumbersome instrument, the device 6000 is suitable for use within a point-of-care setting (e.g., doctor's office, pharmacy or the like) or at the user's home and can receive any suitable biological sample S1. The biological sample S1 (and any of the input samples described herein) can be, for example, blood, urine, male urethral specimens, vaginal specimens, cervical swab specimens, and/or nasal swab specimens gathered using a commercially available sample collection kit.

The sample preparation module 6200 includes a top body 6201, a bottom body 6202, a heater 6230, and a mixing assembly 6250. The top body 6201 and the bottom body 6202 can be referred to collectively as a sample preparation housing, a flow member or a reverse transcription chamber. Although the flow member is shown as being constructed from two pieces (the top body 6201 and the bottom body 6202) that are coupled together, in other embodiments, the flow member can be monolithically constructed. The sample preparation housing (i.e., the top body 6201 and the bottom body 6202) define a sample input opening 6212, a first (or holding) volume 6211, and a serpentine flow channel 6214. In some embodiments, the top body 6201 and/or the bottom body 6202 can define one or more vents. Such vents can allow air to flow into or out of the sample preparation module 6200 (including the first volume 6211 and the serpentine flow channel 6214) as sample is conveyed into and/or out of the sample preparation module 6200. Additionally, the top body 6201 includes a set of fluid interconnects 6215 that allow for fluidic coupling of the sample preparation module 6200 to the fluid transfer valve 6300 and other components within the device 6000.

The sample input opening 6212 is an opening through which the first (or holding) volume 6211 can be accessed. As described above, when the lid 6050 is in the opened position, the biological sample S1 can be conveyed into the holding volume 6211 via the sample input opening 6212. The first (or holding) volume 6211 is a volume within which the biological sample S1 can be mixed with reagents and also heated. For example, in some embodiments the biological sample S1 can be collected in the holding volume 6211 and mixed with either or both of a control organism (identified as reagent R1) and a reverse transcriptase (identified as reagent R2). The control organism and the reverse transcriptase can each be lyophilized or otherwise in solid form. Moreover, the reagents R1 and R2 can be secured within the holding volume 6211 to prevent the reagents R1 and R2 from inadvertently falling out of the device 6000, for example during storage, transportation, or use. For example, in some embodiments, the reagents can be secured within the holding volume 6211 by a cover, basket, or other structure within the holding volume 6211.

In some embodiments, the reagent R1 is a positive control organism, such as *Aliivibrio fischeri, N. subflava*, or any other suitable organism. Specifically, *Aliivibrio fischeri* is suitable because it is gram negative, nonpathogenic, bio safety level 1, not harmful to the environment, and is extremely unlikely to be found on a human. The positive control surface within the detection module contains capture probes for both the control organism (e.g., *A. fischeri*) as well as each of the target organisms. This arrangement ensures that the positive control surface always produces color if the device functions correctly. If only the control organism were present, a very strong positive for one of the target organisms could "swamp out" or "outcompete" the amplification of the control organism during PCR. Under such circumstances, the positive control spot would not produce a color change which would be confusing for the user. This arrangement facilitates the detection method and the device 6000 being operated by a user with minimal (or no) scientific training, in accordance with methods that require little judgment.

In some embodiments, the reagent R2 contains the reverse transcriptase enzymes and other constituents to facilitate the RT-PCR methods described herein. For example, in some embodiments, the reagent R2 includes the salts needed to create the correct buffering environment for the RT-PCR. The reagent R2 is formulated to dissolve in the biological sample within the holding volume 6211.

The biological sample can be heated within the holding volume 6311 to lyse the cells within the biological sample S1 and further lyse (or release) the target RNA from any viruses contained with the biological sample S1. In other words, the biological sample S1 can be heated to both break apart the cells and also disrupt the viruses there to release target RNA for detection. Specifically, the heater 6230 is coupled to the sample preparation housing and/or the bottom body 6202 such that a first portion of the heater 6230 can convey thermal energy into the holding volume 6211. The first portion of the heater 6230 can maintain the biological sample S1 at any suitable temperature and for any of the time periods described herein. For example, in some embodiments, the biological solution can be maintained at a temperature within a lysing temperature range to release a ribonucleic acid (RNA) molecule. The lysing temperature range can be, for example, between about 25 C and about 70 C. In other embodiments, the lysing temperature range can be between about 25 C and about 50 C.

Figure 39:
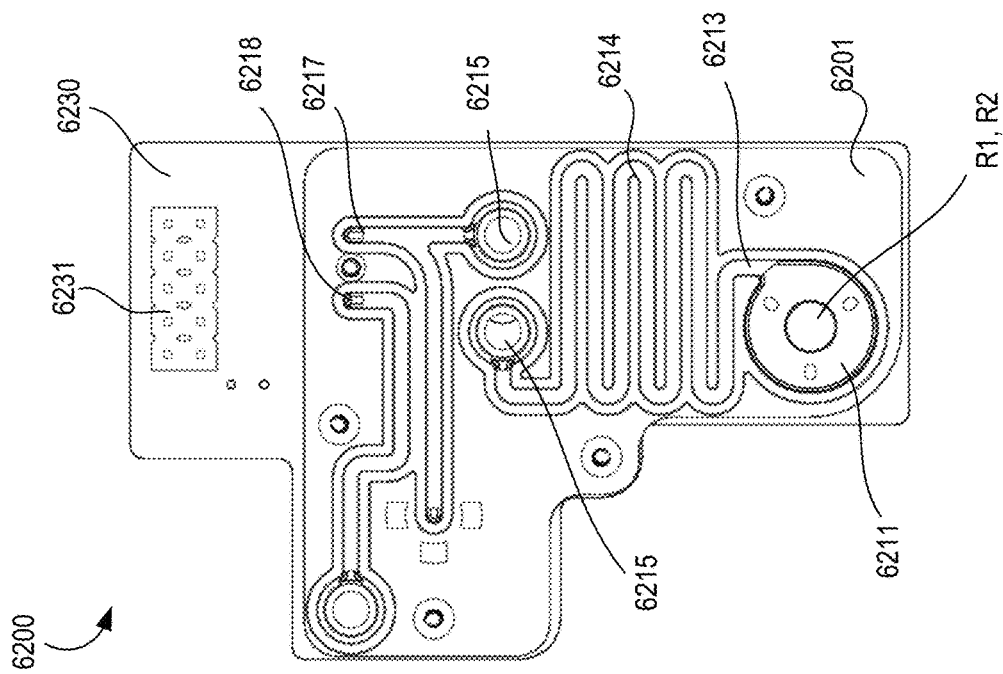
FIGS. 39 and 40 are a cross-sectional view (FIG. 39) and an exploded view (FIG. 40) of the sample preparation module shown in FIGS. 37 and 38.
Figure 38:
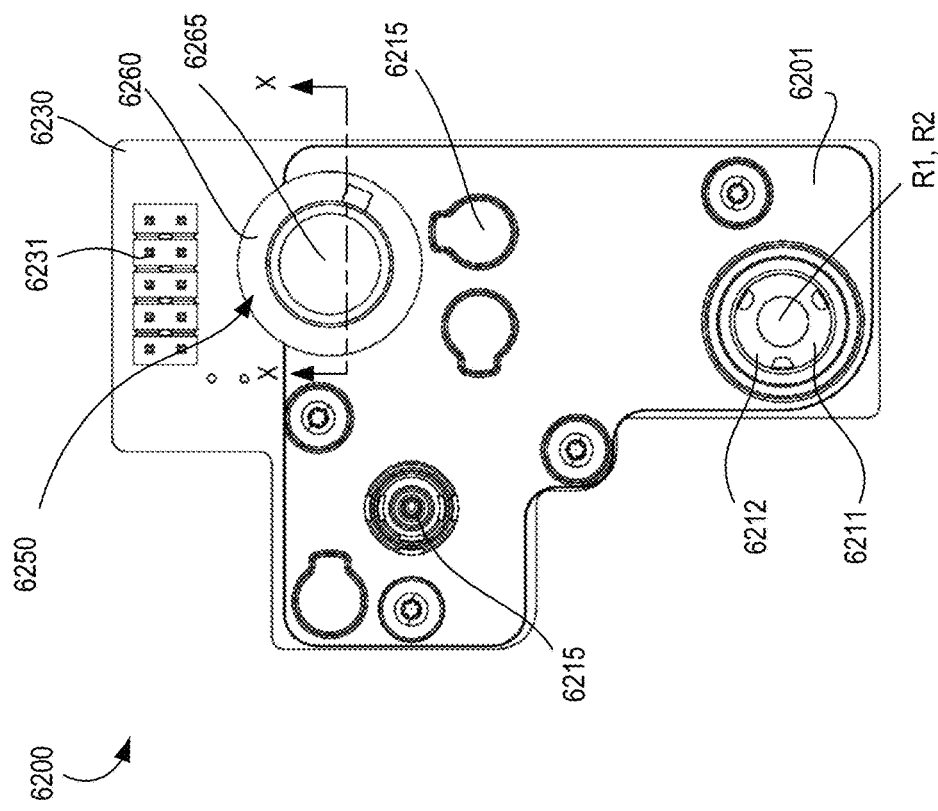

Referring to FIG. 39, which shows a top view cross-section of the sample preparation housing, the first volume 6211 is in fluid communication with the serpentine flow channel 6214, via the inlet opening 6213. In this manner, the lysed biological sample that is mixed with the RT enzyme (also referred to as a reverse transcription solution) can flow from the first (or holding) volume 6211 through the serpentine flow channel 6214. More specifically, when a pressure gradient is applied across the inlet opening 6213 and the output opening 6215 (e.g., via the fluidic drive module 6400), the reverse transcription solution can flow from the holding volume 6211 (first volume) through the serpentine flow channel 6214. The serpentine channel provides a high surface area to volume ratio, and thus allows for rapid RT-PCR and inactivation of the lysis and/or RT enzymes in the solution.

In use, the reverse transcription solution can be heated as it flows through the serpentine flow channel 6214 to perform RT-PCR and further inactivate the enzymes. Specifically, the heater 6230 is coupled to the sample preparation housing and/or the bottom body 6202 such that a second portion of the heater 6230 can convey thermal energy into the serpentine flow channel 6214. The second portion of the heater 6230 can maintain the reverse transcription solution at any suitable temperature and for any of the time periods described herein. For example, in some embodiments, the reverse transcription solution can be maintained at a temperature within a reverse transcription temperature range to produce complementary deoxyribonucleic acid (cDNA) molecules. By rapidly progressing to the reverse transcription, the dwell time during which released RNA are present in the reverse transcription solution can be minimized. Reducing the dwell time can reduce the likelihood that the released RNA will be degraded by ribonuclease (RNase). Limiting such potential degradation by performing the lysing and RT-PCR in a single environment can reduce inconsistencies due to variation in the RNA degradation. Further, the rapid and single-environment methods enabled by the sample preparation module 6200 can allow the RT-PCR methods described herein to be completed without the use of a ribonuclease inhibitor and/or on an unfiltered sample. The reverse transcription temperature range can be, for example, between about 30 C and about 80 C. In other embodiments, the reverse transcription temperature range can be between about 50 C and about 60 C.

In addition to enabling a rapid RT-PCR, the sample preparation module 6200 can also heat the reverse transcription solution to a temperature sufficient to inactivate the one or more lysis or RT enzymes contained therein. For example, the heating element may heat the reverse transcription solution within the channel 6214 to about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C. or greater than 100° C. By heating the reverse transcription solution to a high temperature, the enzymes can be deactivated. In some embodiments, the sample can be heated to about 95 C for about 4 minutes.

As described above, the flow member is in contact with a heating element 6230, which can be, for example, a printed circuit board (PCB) heater. The heating element 6230 includes connectors 6231 and multiple, segmented portions, and thus can independently produce thermal energy into the holding volume 6211 and the serpentine flow channel 6214. In some embodiments, the heating element 6230 is designed to heat the serpentine portion 6214 of the sample preparation module 6200 while not heating the holding volume 6211, and vice-versa.

To minimize the heat energy that can inadvertently transfer between the holding volume 6211 and various portions of the serpentine channel 6214, or even between different portions of the serpentine channel 6214, one or more slots 6232 can be cut in the PCB 6330 to isolate various portions of the heater 6230. For example, in some embodiments, the heater 6230 can include a series of slots and/or openings as described in U.S. Patent Publication No. 2017/0304829 entitled, entitled "Printed Circuit Board Heater for an Amplification Module," which is incorporated herein by reference in its entirety. Moreover, in some embodiments, the heating element of the heater 6230 is located on an internal layer so the top copper pour (not shown) can be used as a heat spreader to minimize temperature variation along the serpentine path.

The reverse transcription solution, after being flowed through the inactivation process, may be flowed via the output port 6215 through the fluid control valve 6300 and into the inlet port 6217 of the mixing assembly 6250. The mixing assembly 6250 mixes the output from the serpentine flow channel 6214 with the reagents (identified as R3) to conduct a successful amplification reaction. Similarly stated, the mixing module 6250 is configured to reconstitute the reagent R3 in a predetermined input volume, while ensuring even local concentrations of reagents R3 in the entirety of the volume. In some embodiments, the mixing assembly 6250 is configured to produce and/or convey a sufficient volume of liquid for the amplification module 6600 to provide sufficient volume output to the detection module 6800.

Figure 41:
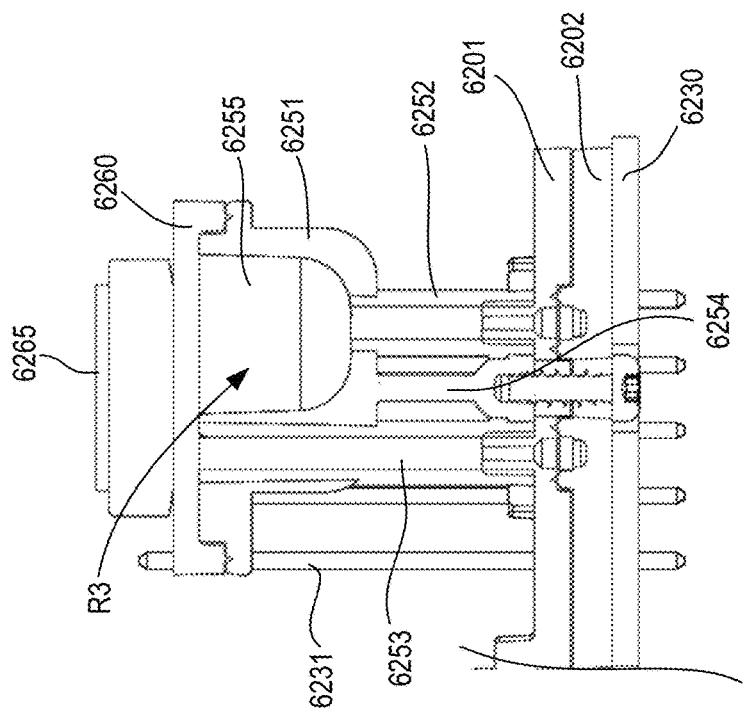
FIG. 41 is a cross-sectional view taken along line X-X in FIG. 38 of the mixing assembly of the sample preparation module shown in FIGS. 37 and 38.
Figure 40:
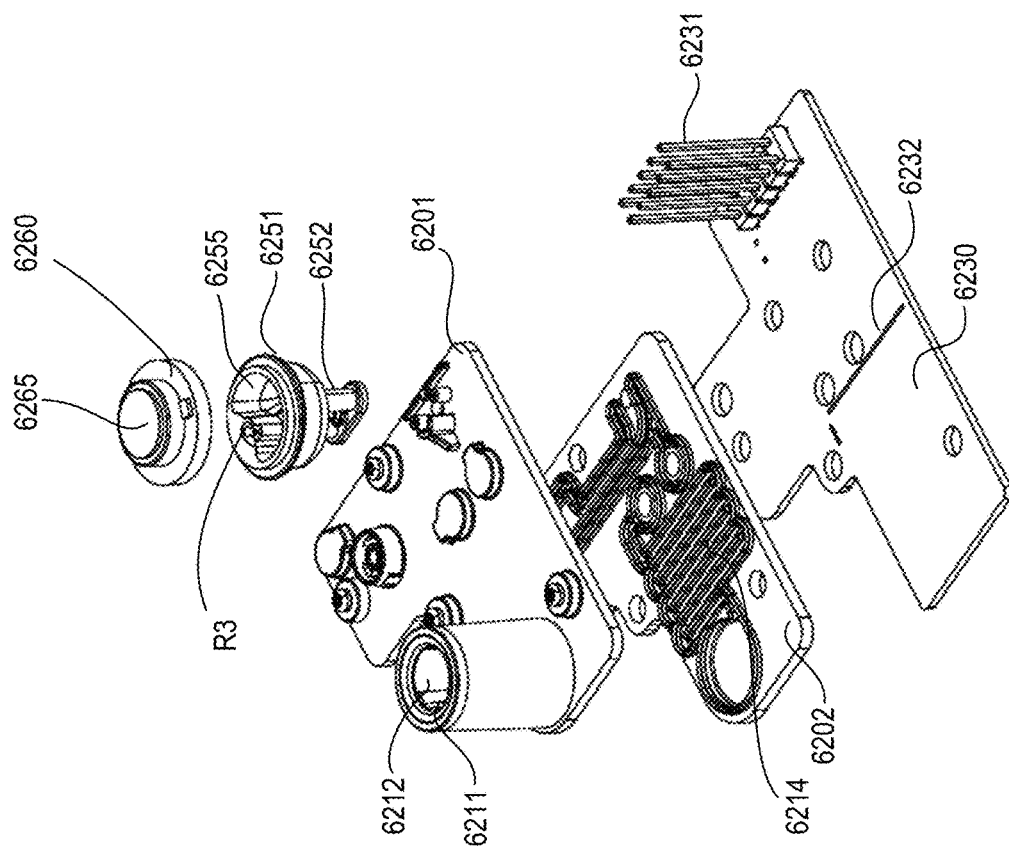
Figure 42:
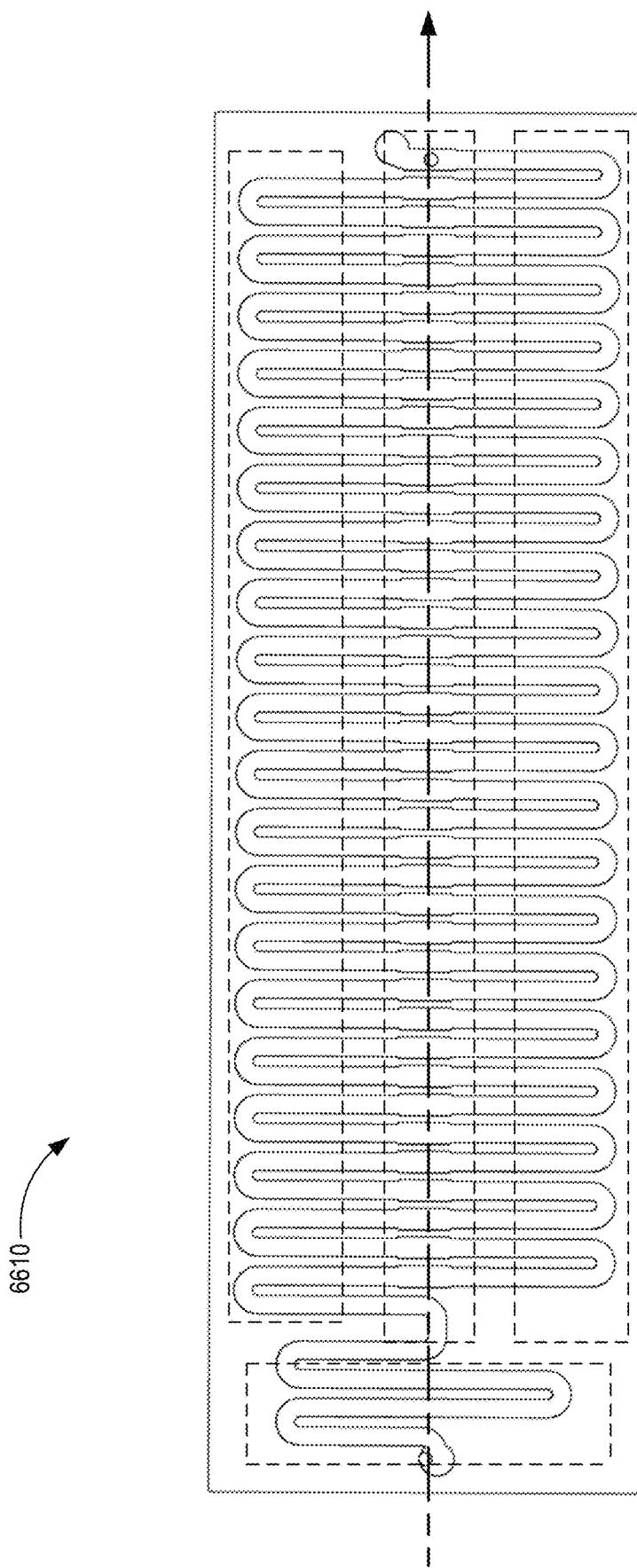
FIG. 42 is a top view of a flow member of the amplification module of the molecular diagnostic test device shown in FIGS. 20 and 21.

Referring to FIGS. 40 and 41, the mixing assembly 6250 is coupled to the top body 6201 and includes a bottom housing 6251, a top housing 6260, and a vibration motor 6265. The bottom housing 6251 defines a mixing reservoir 6255 and contains the amplification reagents R3 therein. The bottom housing 6251 includes an inlet coupling 6252 and an outlet coupling 6253, and is coupled to the top body 6201 by a support member 6254. The top housing 6260 encloses the mixing reservoir 6255 and provides a surface to which the vibration motor 6265 is mounted. The inlet coupling 6252, the outlet coupling 6253, and the support member 6254 can be constructed from any suitable material and can have any suitable size. For example, in some embodiments, the inlet coupling 6252, the outlet coupling 6253, and the support member 6254 are constructed to limit the amount of vibration energy from the motor 6265 that is transferred into the remaining portions of the sample preparation module 6200. For example, in some embodiments, the inlet coupling 6252, the outlet coupling 6253, and/or the support member 6254 can be constructed from a resilient or elastomeric material to allow vibratory movement of the bottom housing 6251 and the top housing 6260 while transferring such energy to the top body 6201.

After being mixed within the mixing assembly 6250, the prepared sample is then conveyed to the amplification module 6600. The transfer of fluids, including the reverse transcription solution, the reagents or the like is caused by the fluidic drive (or transfer) module 6400. The fluidic drive (or transfer) module 6400 can be a pump or series of pumps configured to produce a pressure differential and/or flow of the solutions within the diagnostic test device 6000. Similarly stated, the fluid transfer module 6400 is configured to generate fluid pressure, fluid flow and/or otherwise convey the biological sample and the reagents through the various modules of the device 6000. The fluid transfer module 6400 is configured to contact and/or receive the sample flow therein. Thus, in some embodiments, the device 6000 is specifically configured for a single-use to eliminate the likelihood that contamination of the fluid transfer module 6400 and/or the sample preparation module 6200 will become contaminated from previous runs, thereby negatively impacting the accuracy of the results. As shown, the fluid transfer module 6400 can be a piston pump that is coupled to the reagent module 6700 by one of the clips 6790. The fluid drive module 6400 can be driven by and/or controlled by the electronic control module 6950. For example, in some embodiments, the fluid drive module 6400 can include a DC motors, the position of which can be controlled using rotary encoders (not shown). In other embodiments, the processor 6951 of the electronic control module 6950 can include code to and/or be configured to implement a closed loop method of tracking motor position by monitoring the current draw of motor, as described in International Patent Publication No. WO2016/109691, entitled "Devices and Methods for Molecular Diagnostic Testing," which is incorporated herein by reference in its entirety.

The amplification module 6600 includes a flow member 6610, a heater 6630, and a heat sink 6690. The flow member 6610 can be any suitable flow member that defines a volume or a series of volumes within which the that prepared solution S3 can flow and/or be maintained to amplify the target nucleic acid molecules within the solution S3. The heater 6630 can be any suitable heater or group of heaters coupled to the flow member 6610 that can heat the prepared solution within the flow member 6610 to perform any of the amplification operations as described herein. For example, in some embodiments, the amplification module 6600 (or any of the amplification modules described herein) can be similar to the amplification modules shown and described in U.S. Patent Publication No. 2017/0304829 entitled "Printed Circuit Board Heater for an Amplification Module," which is incorporated herein by reference in its entirety.

In some embodiments, the flow member 6610 defines a single volume within which the prepared solution is maintained and heated to amplify the nucleic acid molecules within the prepared solution. In other embodiments, the flow member 6610 can define a "switchback" or serpentine flow path through which the prepared solution flows. Similarly stated, the flow member 6610 defines a flow path that is curved such that the flow path intersects the heater 6630 at multiple locations. In this manner, the amplification module 6600 can perform a "flow through" amplification reaction where the prepared solution flows through multiple different temperature regions.

The flow member 6610 (and any of the flow members described herein) can be constructed from any suitable material and can have any suitable dimensions to facilitate the desired amplification performance for the desired volume of sample. For example, in some embodiments, the amplification module 6600 (and any of the amplification modules described herein) can perform 6000× or greater amplification in a time of less than 15 minutes. For example, in some embodiments, the flow member 6610 (and any of the flow members described herein) is constructed from at least one of a cyclic olefin copolymer or a graphite-based material. Such materials facilitate the desired heat transfer properties into the flow path. Moreover, in some embodiments, the flow member 6610 (and any of the flow members described herein) can have a thickness of less than about 0.5 mm. In some embodiments, the flow member 6610 (and any of the flow members described herein) can have a volume about 150 microliters or greater, and the flow can be such that at least 10 microliters of sample is amplified. In other embodiments, at least 20 microliters of sample are amplified by the methods and devices described herein. In other embodiments, at least 30 microliters of sample are amplified by the methods and devices described herein. In yet other embodiments, at least 50 microliters of sample are amplified by the methods and devices described herein.

The heater 6630 can be any suitable heater or collection of heaters that can perform the functions described herein to amplify the prepared solution. In some embodiments, the heater 6630 can establish multiple temperature zones through which the prepared solution flows and/or can define a desired number of amplification cycles to ensure the desired test sensitivity (e.g., at least 30 cycles, at least 34 cycles, at least 36 cycles, at least 38 cycles, or at least 60 cycles). The heater 6630 (and any of the heaters described herein) can be of any suitable design. For example, in some embodiments, the heater 6630 can be a resistance heater, a thermoelectric device (e.g. a Peltier device), or the like. In some embodiments, the heater 6630 can be one or more linear "strip heaters" arranged such that the flow path crosses the heaters at multiple different points. In other embodiments, the heater 6630 can be one or more curved heaters having a geometry that corresponds to that of the flow member 6610 to produce multiple different temperature zones in the flow path.

Although the amplification module 6600 is generally described as performing a thermal cycling operation on the prepared solution, in other embodiment, the amplification module 6600 can perform any suitable thermal reaction to amplify nucleic acids within the solution. In some embodiments, the amplification module 6600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

The detection module 6800 is configured to receive output from the amplification module 6600 and reagents from the reagent module 6700 to produce a colorimetric change to indicate presence or absence of target organism in the initial input sample. The detection module 6800 also produces a colorimetric signal to indicate the general correct operation of the test (positive control and negative control). In some embodiments, color change induced by the reaction is easy to read and binary, with no requirement to interpret shade or hue. The detection module 6800 can be similar to the detection modules shown and described in International Patent Publication No. WO2016/109691, entitled "Devices and Methods for Molecular Diagnostic Testing," which is incorporated herein by reference in its entirety.

Figure 43:
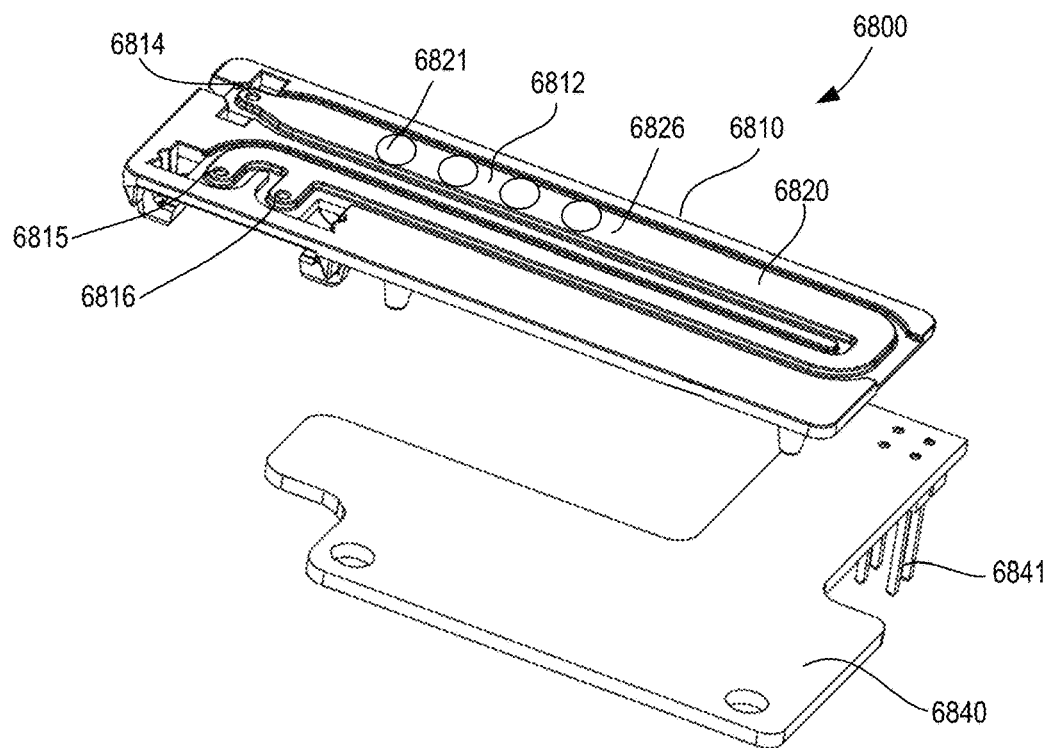
FIG. 43 is an exploded view of the detection module of the molecular diagnostic test device shown in FIGS. 20 and 21.

Referring to FIG. 43, the detection module includes a lid (not shown), a detection housing 6810 and a heater 6840. The heater 6840 can be similar to any of the circuit board heaters described herein and also shown and described in International Patent Publication No. WO2016/109691, entitled "Devices and Methods for Molecular Diagnostic Testing," which is incorporated herein by reference in its entirety. The lid and the detection housing 6810 form a flow cell for detection. The housing 6810 defines a detection chamber/channel 6812 having a sample inlet port 6814, a first reagent inlet/outlet port 6815, a second reagent inlet/outlet port 6816. The sample inlet port 6814 is fluidically coupled to the outlet of the amplification module 6600 and receives the amplified sample. The first reagent port 6815 and the second reagent port are coupled to the reagent module 6700 via the fluid interconnect 6738. Thus, in use a wash/blocking reagent (e.g., previously identified as R4) can be conveyed into the detection channel 6812 via the first reagent port 6815 or the second reagent port 6816. Similarly, a detection enzyme (e.g., previously identified as R5) and a detection substrate (e.g., previously identified as R6) can be conveyed into the detection channel 6812 via the first reagent port 6815 or the second reagent port 6816. Additionally, the first reagent port 6815 or the second reagent port 6816 can also be used to receive waste or excess reagents or flows out of the first reagent port 6815 or the second reagent port 6816.

The detection channel 6812 is surrounded or defined by a surface 6820 that includes one or more detection surfaces 6821, as well as non-detection surfaces 6826. The detection surfaces 6821 include a series of capture probes to which the target amplicon can be bound when the detection solution flows across the detection surface 6821. The capture probes can be any suitable probes formulated to capture or bind to the target amplicon. Specifically, in some embodiments, the detection portion 6821 includes five detection surfaces. Each of the detection surfaces are chemically modified to contain a desired capture probe configuration. Specifically, in some embodiments, a first detection surface can include a hybridization probe specific to *Neisseria gonorrhea* (NG). A second detection surface can include a hybridization probe specific to *Chlamydia trachomatis* (CT). A third detection surface can include a hybridization probe specific to *Trichomonas vaginalis* (TV). A fourth detection surface can include non-target probe for a negative control. A fifth detection surface can include a hybridization probe for a positive control (*A. fischeri, N. subflava*, or the like).

The non-detection surfaces 6826 can be those surfaces surrounding the detection surfaces 6821. As described above with reference to the detection module 3800, in some embodiments, the entire surface 6820 (including the detection surfaces 6821 and the non-detection surfaces 6826) can be coated with a blocking solution as a part of the methods described herein.

The fluid transfer valve 6300 is shown in FIG. 19 (schematically) and 46. FIGS. 47-52 show the fluid transfer valve 6300 in several different operational configurations, with the flow (or vent) housing 6310 shown in transparent lines so that the position of the valve disk 6320 can be seen. The fluid transfer valve 6300 includes a flow housing 6310, a valve body (or disk) 6320, a main housing 6330, and a motor 6340. The flow housing 6310 defines a valve pocket within which the valve disk 6320 is rotatably disposed. The flow housing 6310 includes a flow structure that defines at least six transfer (or vent) flow paths, shown in FIGS. 47-52. Specifically, the flow paths include a sample inlet path 6312, a sample outlet path 6313, an amplification path 6314, a wash solution (reagent R4) vent path 6315, a detection enzyme (reagent R5) vent path 6316, and a detection substrate (reagent R6) vent path 6317. The flow housing 6310 includes connection portions where each of the transfer or vent paths can be coupled to the respective modules via the interconnects described herein. Each of the fluid connection/vent ports described above opens into the valve pocket. In this manner, when the valve body 6320 rotates around the center of the valve pocket (as shown by the arrow JJ), the slot channel 6321 of the valve body 6320 can connect various central ports to the other ports depending on their radial and angular position. The use of multiple radii allows not only a single port, but multiple ports at once to be fluidically coupled or vented depending on the configuration.

Figure 47:
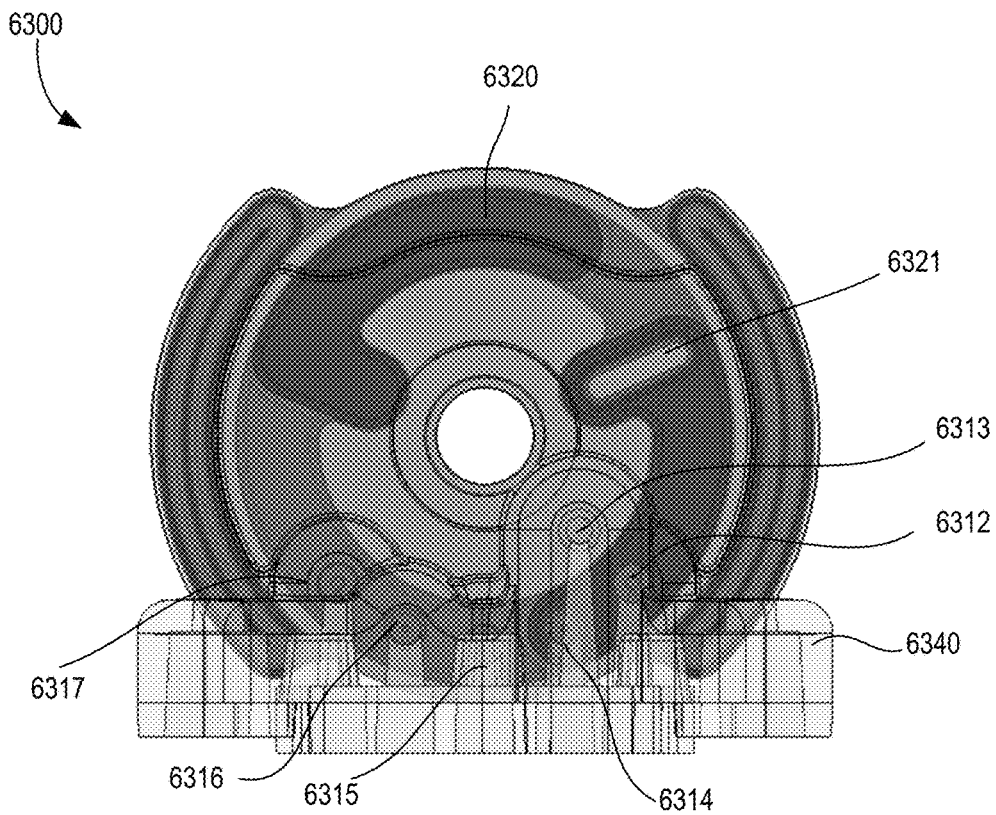
FIGS. 47-52 are front views of the rotary valve assembly shown in FIG. 46 with the vent housing being "transparent" to show the valve disc in each of six different operational configurations.
Figure 48:
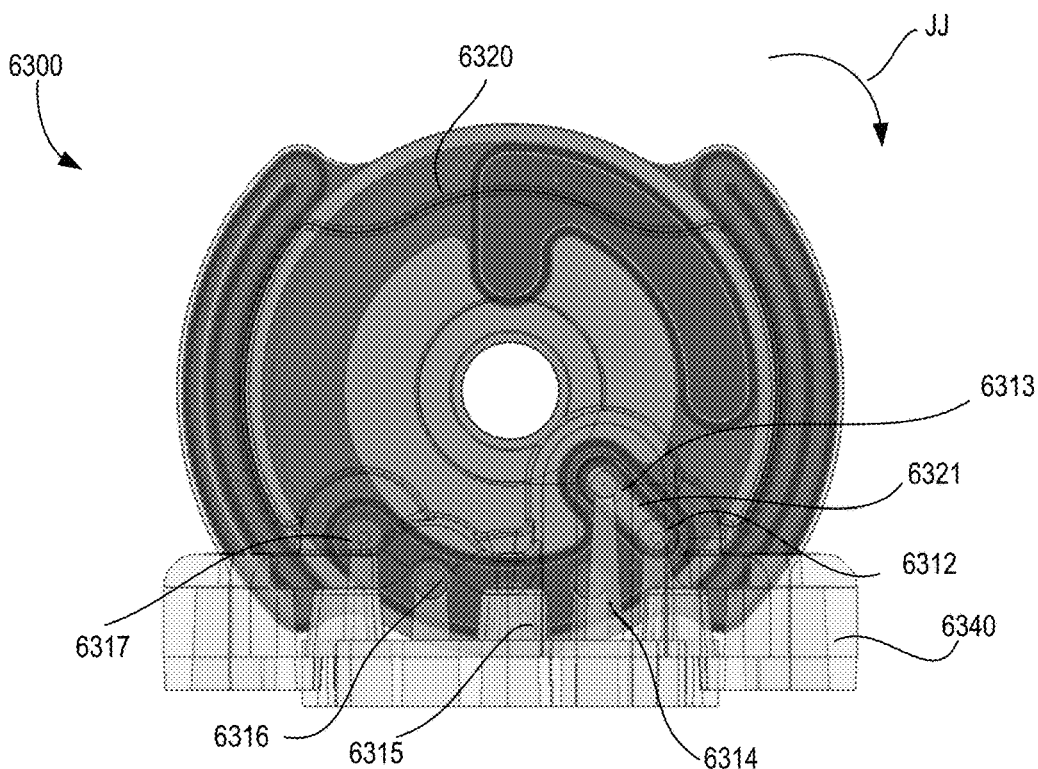

The valve assembly 6300 can be moved between various different configurations, depending on the angular position of the valve body 6320 within the valve pocket. FIGS. 47-52 show the assembly in various different configurations. FIG. 47 shows the valve assembly 6300 in the home (or initial position), in which the sample inlet path 6312 and the sample outlet path 6313, as well as the other fluid connection/vent ports, are closed. FIG. 48 shows the valve assembly 6300 in a first rotational position, in which the sample inlet path 6312 and the sample outlet path 6313 are opened. With the valve assembly 6300 in the first position, actuation of the fluidic drive module 6400 can produce a flow of the biological sample into and through the serpentine channel 6214 and then to the mixing assembly 6250. In this manner, the device 6000 can perform the RT-PCR methods as described herein (e.g., the method 50, or any of the other RT-PCR methods). Moreover, the timing of the valve actuation and the power supplied to the fluidic drive module 6400 (e.g., the pump) can be controlled by the electronic control module 6950 to maintain the flow rate through the sample preparation module 6200 (including the serpentine channel 6214) within a range that the desired performance for the RT-PCR can be achieved.

After completion of the mixing process within the mixing assembly 6250, the valve assembly 6300 can be further moved into the second position (not shown). When the valve is in the second position, the amplification path 6314 is opened (i.e., is aligned with the flow slot 6321), thus allowing transfer of the mixed solution (i.e., post RT-PCR) to be conveyed into the amplification module 6600. The timing of the valve actuation and the power supplied to the fluidic drive module 6400 (e.g., the pump) can be controlled by the electronic control module 6950 to maintain the flow rate through the amplification module 6600 within a range that the desired performance for the amplification can be achieved. Moreover, with the valve assembly 6300 in the second position, continued actuation of the fluidic drive module 6400 will convey the amplified solution into and through the detection module 6800.

Figure 49:
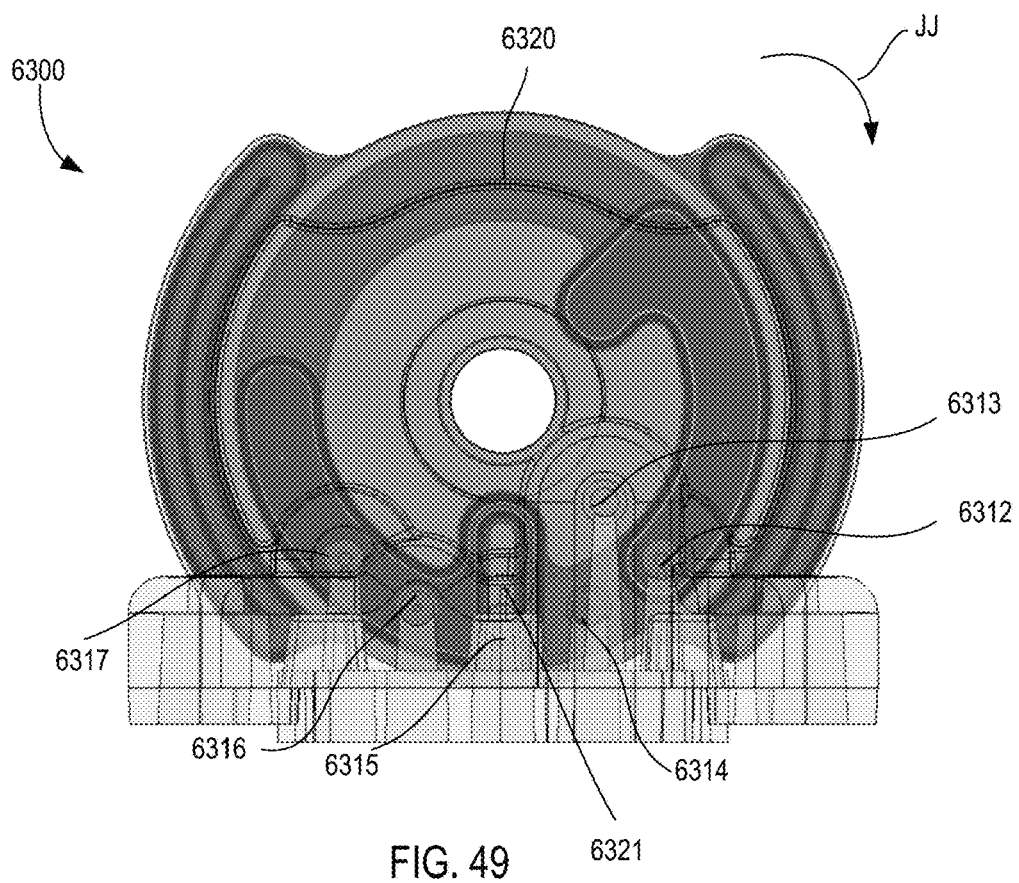
Figure 50:
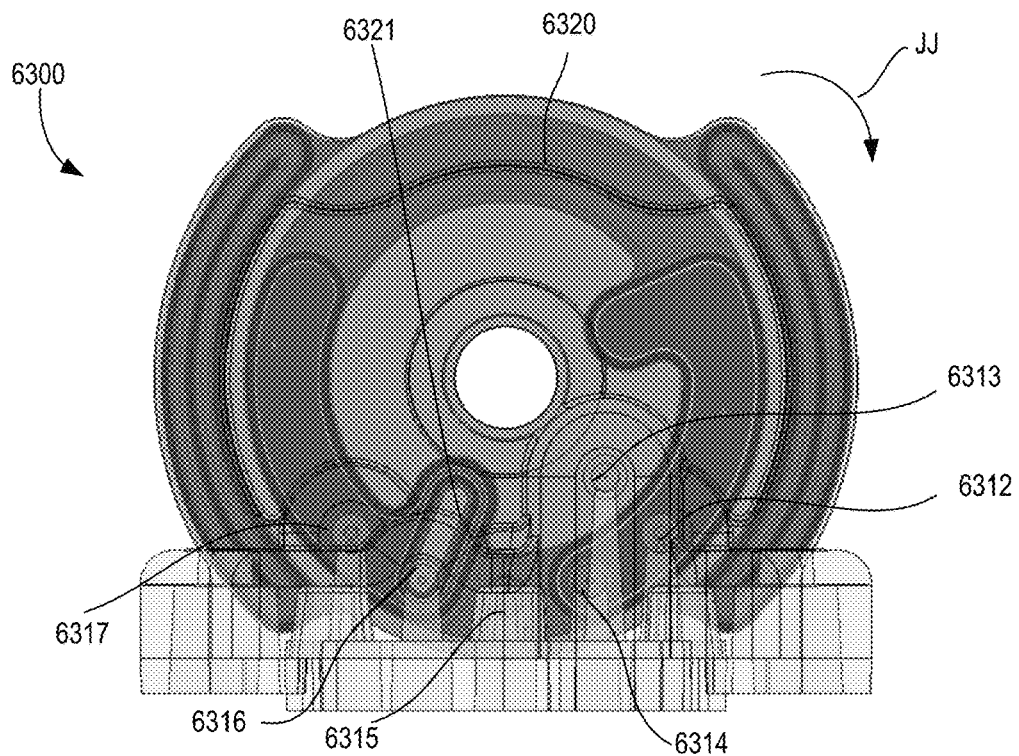
Figure 51:
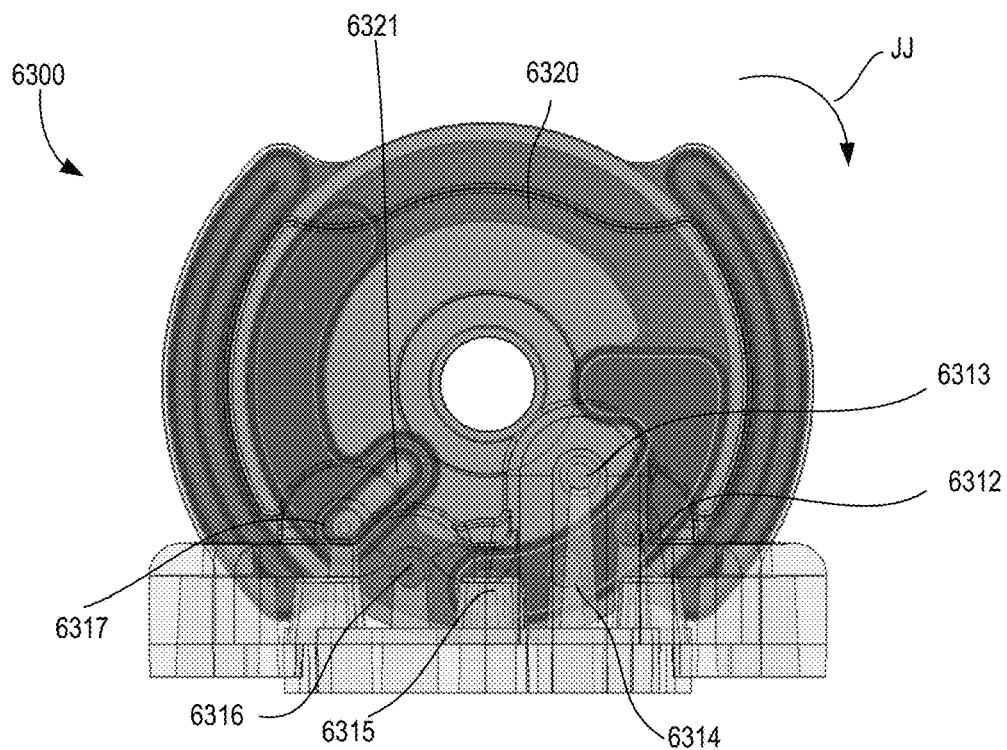
Figure 52:
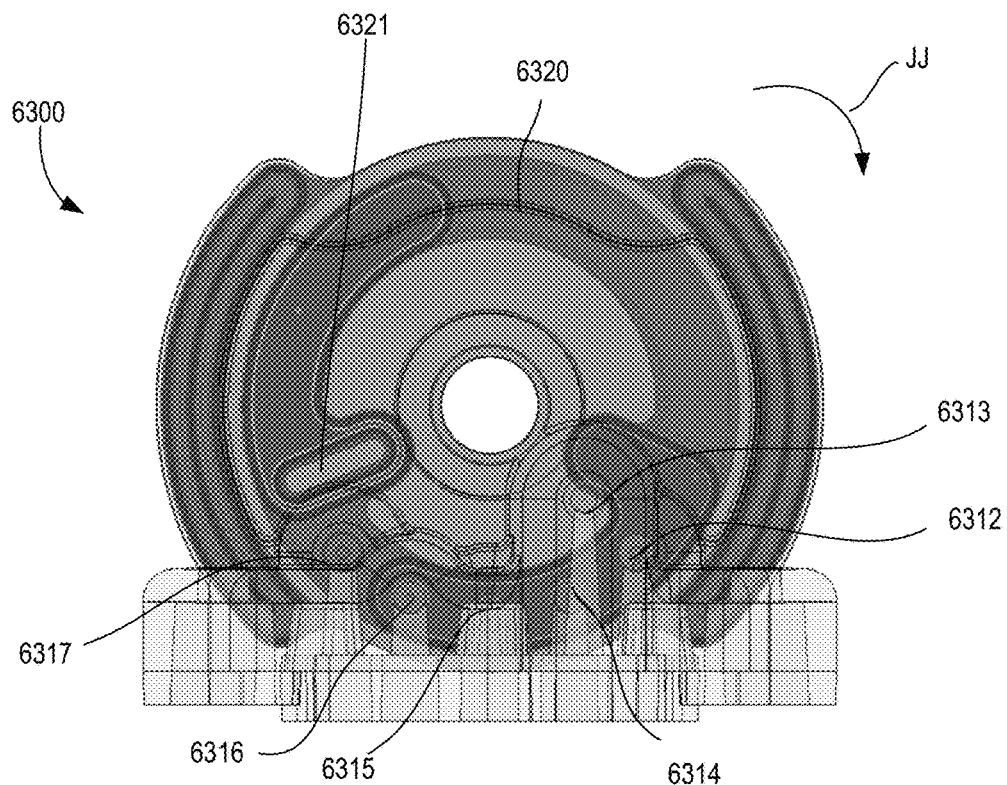

As described herein, the detection operation is accomplished by conveying a series of reagents into the detection module at specific times. Although closing the lid 6050 actuates the reagent module 6700 to open (or release) the reagents from their respective sealed containers, the reagents remain in the reagent module 6700 until needed in the detection module 6800. When a particular reagent is needed, the rotary valve 6300 opens the appropriate vent path (i.e., the wash solution vent path 6315, the detection enzyme vent path 6316, and the detection substrate vent path 6317) to the reagent module 6700. Actuation of the fluidic drive module 6400 applies vacuum to the output port of the reagent module 6700 (via the detection module 6800), thus conveying the selected reagent from the reagent module 6700 into the detection module 6800. FIG. 49 shows the valve assembly 6300 in a third rotational position, in which the detection enzyme vent path 6316 is opened. With the valve assembly 6300 in the third position, actuation of the fluidic drive module 6400 can produce a flow of the detection enzyme (reagent R5) into the detection module 6800. FIG. 50 shows the valve assembly 6300 in a fourth rotational position, in which the wash solution (reagent R4) vent path 6315 is opened. With the valve assembly 6300 in the fourth position, actuation of the fluidic drive module 6400 can produce a flow of the wash (or multi-purpose wash/blocking) solution (reagent R4) into the detection module 6800. FIG. 51 shows the valve assembly 6300 in a fifth rotational position, in which the detection substrate (reagent R6) vent path 6317 is opened. With the valve assembly 6300 in the fourth position, actuation of the fluidic drive module 6400 can produce a flow of the substrate (reagent R6) into the detection module 6800. FIG. 52 shows the valve assembly 6300 in a final position, in which the vent paths are closed.

As described with reference to the apparatus 3000, the method 30, and the method 40 above, in some embodiments, the device 6000 can include a multi-purpose wash/blocking reagent (e.g., reagent R4) and can, at separate times, convey a portion of the multi-purpose wash/blocking reagent into the detection module 6800. Specifically, in some embodiments, the valve assembly 6300 can first be placed into the fourth position (FIG. 50) and a portion of the multi-purpose wash/blocking reagent can be conveyed into the detection module 6800, in accordance with the method 30 or the method 40 described herein. Additionally, after a predetermined dwell time (e.g., 30 seconds), and with the valve assembly 6300 still in the fourth position, the motion of the fluidic drive module 6400 can be reversed to draw the multi-purpose wash/blocking reagent back into the reagent module 6700. The valve assembly 6300 can then be moved into the first position to commence processing of the biological sample.

The device 6000 can be used to perform any of the methods described herein. Referring to FIGS. 53A-53C, to use the device, a biological sample S1 is first placed into the sample input opening 6021 (e.g., using a sample transfer pipette 6110), as described above. The lid 6050 is then moved to the closed position, as shown by the arrow KK in FIG. 53B. As described above, closing the lid 6050 encloses the sample input volume 6211, actuates the electronic control module 6950 (and/or the processor 6951 included therein), and also actuates the reagent module 6700, as described above. The device 6000 is then plugged in via the power cord 6905 to couple the device 6000 to a power source. In this manner, the device 6000 can, in addition to disposing the sample S1 therein and plugging in the device, be actuated by a single action (i.e., the closing of the lid).

Methods and Devices Using a RT-PCR Device to Detect HIV-1 RNA in Finger-Stick Blood for Point of Care Testing In some embodiments, the device 6000 or any of the devices described herein can be used to perform an HIV-1 RNA detection assay. The HIV-1 RNA detection assay will enable non-technical persons to test a finger-stick self-collected blood sample at home or in lesser developed country settings using an inexpensive, disposable instrument-free device. Use of this device has the potential to transform the diagnosis of acute or early HIV infection and anti-retroviral treatment monitoring. In some embodiments, a molecular diagnostic test device includes amplification and detection platforms to enable on-device cDNA production from viral RNA. In some embodiments, the cDNA is amplified through a serpentine PCR module.

In some embodiments, a molecular diagnostic test device includes an HIV-1 RNA detection platform (also referred to as the RT Enhanced Platform (RTEP)). Some versions of a diagnostic test device are composed of an input port, inactivation chamber, mixing chamber, two check valves, PCR module and a detection module with requisite reagent containers, a piston pump and rotary valve. FIGS. 15 and 19 each show two example of an RTEP version, which includes the sample preparation module that can perform RT-PCR as described herein. Additionally, the sample preparation module integrates a reverse transcription step to allow for processing of viral RNAs. The RT step is in-line with the rest of the process, and thus can be bypassed through firmware control for panels that do not require it. The heating is provided by a separate and independent heating circuit on the lysis heater board.

In use, plasma (or blood) is dispensed into the lysis chamber, the syringe pump is activated to create a vacuum which causes the sample to flow through a heated channel where viral lysis occurs, releasing genomic RNA. Temperatures in the channel are controlled to 92C to ensure denaturation of viral RNA, and sample fluid is held at this temperature for approximately 30 seconds. Sample fluid then progresses through a check valve and into a mixing chamber which holds several lyophilized beads (PCR master mix reagents and the RT enzyme), which are hydrated by the sample fluid. The chamber is mixed by a small vibratory motor and samples are then incubated at 55 C to allow reverse transcription of viral RNA to cDNA. At this point, the syringe pump will reverse direction and pressurize the mixing chamber to move the chamber contents through an additional heater at 95 C to inactivate the RT enzyme and activate thermal-stable hot-start DNA polymerase. The process then continues to the PCR and detection modules, as described herein or in any of the patent applications or publications incorporated herein.

In some embodiments, the methods and device can include multiple primer sets to address the marked variability of the HIV-1 genome. For example, the target sequence(s) can include highly conserved regions of two genes, and the primer sets can both be included as part of the multiplex assay. In addition, the methods and device can include primers for the MS2 RNA bacteriophage, which will serve as a lysis and amplification control. Thus, the resulting multiplex assay will contain three primer sets, two sets corresponding to separate conserved regions of the HIV-1 genome and one corresponding to the MS2 phage genome. As described in greater detail below, one primer of each set will be used to prime the reverse transcription step for the one-step RT-PCR assay used herein.

In some embodiments, methods and devices can include forward and reverse primers and TaqMan probes for two HIV-1 genes and the MS2 phage positive control (Table 1). The forward primer is 5' biotinylated. Reverse primers are also used to prime the reverse transcription reaction of a one-step RT-PCR. TaqMan probes with the indicated sequences will have the FAM fluorophore at the 5' end, and the BHQ2 quencher at the 3' end.

TABLE 1

Initial forward and reverse primer and TaqMan probe sequences for one-step multiplex RT-PCR assay.

| Organism | Gene Target | Strand | Sequence (5' to 3') | SEQ ID NO: |
|---|---|---|---|---|
| HIV-1 | | Forward | | |
| | | Reverse | | |
| | | Probe | | |
| HIV-1 | | Forward | | |
| | | Reverse | | |
| | | Probe | | |
| MS2 | MS2g1 | Forward | TGGCACTACCCCTCTCCGTATTCAC | 1 |
| | | Reverse | GTACGGGCGACCCCACGATGAC | 2 |
| | | Probe | CACATCGATAGATCAAGGTGCCTACAAGC | 3 |

In some embodiments, the optimized multiplex PCR assay can include a one-step multiplex reverse transcription (RT)-PCR assay that uses the HIV-1 and MS2 phage reverse PCR primers to prime cDNA synthesis. The methods and the device can include validated primer sets and optimized master mix, containing both the reverse transcriptase and thermostable DNA polymerase enzymes. In this manner, the device can perform the "ultra-fast" one-step multiplex RT-PCR assay to amplify armored RNA templates that correspond to the two HIV-1 genes and the MS2 positive control gene. The time required for the production of cDNA from an RNA template before initiating PCR is critical as it must not extend the overall sample-to-answer, turn-around-time beyond the 20-minute specification for the assay. Each of the three virus armored RNA templates is individually serially diluted in TE buffer and each dilution then subjected to simplex one-step RT-PCR using laboratory instruments programed to conduct the ultra-fast RT step to produce cDNA followed by "fast" cycling PCR amplification of the cDNA.

In some embodiments, a multiplex RT-PCR assay is characterized by the following: 1) the assay detects and identifies armored RNAs corresponding to the amplicon sequences for the two assayed HIV-1 genes and the MS2 phage gene when these are diluted into a pooled EDTA plasma sample; and 2) the assay detects and identifies low concentrations of each HIV-1 armored RNA in a pooled EDTA plasma sample that correspond to the desired LoD. To ensure the desired results, in some embodiments, the assay (or device) can include a separate dedicated RT primer. In some embodiments, a method can include increasing the temperature of the RT step to reduce RNA secondary structure.

One potential problem address by the current devices and methods relates to the presence of PCR inhibitors in plasma including EDTA, heme and IgG. In part, the sample preparation module and methods have circumvented this issue by using a nylon filter that binds nucleic acids; because once bound, the nucleic acids can be washed and then eluted in buffer that is largely free of plasma constituents. Use of the MS2 phage processing and amplification control provides a sensitive metric for the presence of inhibitors. If PCR inhibition persists, the heat lysis step can be extended and/or the assay can employ a variant of heat stable DNA polymerase that is resistant to fecal inhibitors such as Omni Klentaq. If chelation of Mg by EDTA reduces PCR efficiency its concentration in the PCR master mix can be increased.

In some embodiments, a method of detecting HIV can include separating plasma. IN particular, plasma is the preferred sample matrix for monitoring virologic control of persons receiving ARV treatment and for the detection of HIV-1 RNA in acute/early HIV infection. It is understood that other sample types (e.g., dried blood spots) are acceptable alternatives in remote locations and that virus can also be found in other body fluids including vaginal secretions and semen. However, in some embodiments, the device and methods can include any suitable plasma separation modules that employ any desired separation methods.

In some embodiments, a method includes a stepwise User-Directed process that can be performed in the home or in a remote developing country setting. The operations include: (1) finger-stick blood is obtained by the User with a commercially available lancet; (2) the blood is deposited into the plasma separation module either directly or using a commercially available capillary tube included in the kit; (3) plasma is automatically separated from blood by the plasma separation module; (4) User transfers plasma from the plasma separation module to the HIV molecular diagnostic device (sample input port) using a transfer pipette included in the kit; (5) User activates the device by depressing any number of buttons; and (6) User records results. In some embodiments, a device includes a physically integrated plasma separation module (i.e., within the molecular diagnostic device).

Plasma volume is a function of finger-stick blood input volume and separation efficiency. It is understood that finger-stick blood volume estimates range widely from, but that at least one commercial lancet (BD blue) is reported to yield an average of 400 ul of blood (ref). Finger-stick blood can be collected using commercially available EDTA coated capillary tubes the contents of which can be deposited into the plasma separation module input port. Separation efficiencies average ~30% of finger-stick blood volume. Therefore, given the expected LoD of the Click HIV-1 device of ≤200 virus copies/ml plasma and 30% plasma separation efficiency, the minimal input volume required to meet this LoD is 150 ul blood, which would yield 45 ul plasma containing 8 HIV-1 virus copies at a plasma HIV-1 concentration of 200 copies/ml.

In some embodiments, a method includes separating the plasma using a super-hydrophobic plasma separator similar to the type developed by Prof. Changchun Liu's group at the University of Pennsylvania, licensed to Drummond Scientific. Such mechanisms are shown to extract 65 ul of hemoglobin-free, PCR-compatible plasma from 200 ul of EDTA anticoagulated blood in <10 min. In some embodiments, the separator can include a 1.5×1×0.3 inch wide disposable device uses a clamshell-style casing to contain a super-hydrophobic sample well into which finger-stick blood is deposited and an inverted asymmetric polysulfone membrane (Vivid® Plasma Separation membrane, Pall). The combination allows red blood cells (RBCs) in a sample to sediment away from the membrane, rather than through it, thus preventing the membrane from clogging and providing a more efficient means of separation. Plasma then collects in the plasma exit port where it can be removed using a simple, low pressure vacuum produced by withdrawing the plunger of a tightly fitting pipette.

In some embodiments, a method includes separating the plasma using a spiral glass-fiber membrane housed within a protective cartridge that allows lateral flow separation of the cellular components of blood from cell-free plasma with minimal hemolysis. Such separation devices can include the HemaSpot-SE Device, which accepts a small finger-stick blood sample. When 4-5 drops of finger-stick blood (~150 µL) are applied to the center of the device a yield of ~50 µL of plasma is generated, thus providing a plasma separation efficiency of ~33%, similar to that afforded by the super-hydrophobic membrane described above. As part of the collaboration proposed here, the current device will be modified to accept blood volumes of 150 to 400 ul and the desiccant removed. Once a finger-stick blood sample is applied to the input port, the cartridge is closed. Within three minutes plasma separation is complete, the cartridge is opened and the blood-free, plasma-containing terminal one-half of the still-moist spiral filter is detached and transferred to a capped tube containing universal transport medium. The tube is swirled to elute virus from the membrane and the liquid then pipette-transferred to the sample processing reservoir of the HIV-1 molecular diagnostic test device.

In some embodiments, a method does not require plasma separation, but rather selectively amplifies only HIV-1 RNA (but not pro-viral DNA) in an ETDA anticoagulated blood sample in the molecular diagnostic test device.

Methods and Devices Using a RT-PCR Device to Detect Upper Respiratory Tract Infections In some embodiments, any of the devices described herein can be used to perform a single-use (disposable), point-of-need, diagnostic test for detecting Influenza A (Flu A), Influenza B (Flu B), and Respiratory Syncytial Virus (RSV) from a nasal swab sample. This will assist clinicians in identifying patients better served by antivirals, thus reducing the prescription of unnecessary and ineffective antibiotics that lead to antimicrobial resistance.

In some embodiments, the test device (and methods) can include a nasal swab and can be conducted on any of the devices described herein.

In some embodiments, the methods and devices can be optimized to ensure that cross-reactivity with the following pathogens (listed in Table 2) is limited.

TABLE 2

| List of pathogens Pathogen |
| --- |
| Influenza A/Perth/16/2009 (H3N2)-like |
| Influenza A/Brisbane/10/07 H3 |
| Influenza A/Port Chalmers/1/73 H3N2 |
| Influenza A/Taiwan/42/06 H1N1 |
| Influenza A/Wisconsin/67/05 H3 |
| Influenza A/California/7/2009-like (pH1N1) |
| A/Anhui/1/2013 (H7N9) (inactivated virus) |
| A/Egypt/321/2007 (H5N1) (inactivated virus) |
| A/Shanghai/1/2013 (H7N9) (inactivated virus) |
| A/Vietnam/1194/2004 (H5N1) (inactivated virus) |

TABLE 2-continued

| List of pathogens Pathogen |
| --- |
| Influenza B/Florida/02/2006 (Victoria) |
| Influenza B/Panama/45/90 (Yamagata) |
| Influenza B/Brisbane/60/2008 |
| RSV A/Long |
| RSV B/9320 |

In addition, the assay performance can be optimized to avoid reduced performance in the presence of inanimate substances that may be present in infected nasal secretions (see the listing below) and which may interfere with device performance including a common topical nasal decongestant (Afrin), a topical steroid nasal spray (Flonase) and human whole blood and mucin. In some embodiments, each assay includes as a positive control the MS2 bacteriophage that monitors assay performance from the sample processing step, through RT-PCR amplification to amplicon detection on the detection platform. Should these or other substances inhibit any aspect of assay performance, then the positive control would register as "not detected" and the assay result would be indeterminate.

TABLE 3

List of pathogens

| Microorganisms | Common Substances and assay final concentration |
| --- | --- |
| Adenovirus 7a | Afrin ® (Oxymetazoline), 50 ul/ml |
| Bordetella pertussis (A639) | Flonase ® (Fluticasone), 10 ug/ml |
| Chlamydia pneumoniae | Human Whole Blood, 10% (v/v) whole blood |
| Coronavirus 229E | Mucin Protein, 5% (v/v) |
| Coronavirus OC43 | |
| Corynebacterium diphtheriae | |
| Enterovirus 71 | |
| Mycoplasma pneumonia M129 | |
| Metapneumovirus | |
| Parainfluenza type 1 | |
| Rhinovirus type 1A | |
| Staphylococcus aureus (COL) | |
| Staphylococcus epidermidis | |
| Streptococcus pyogenes | |

In some embodiments, any of the systems described herein can be modified to perform an enteropathogen diagnostic assay that simultaneously detects both DNA bacterial (i.e., C. jejuni, S. enterica, Shigella sps) and RNA viral targets (Norovirus).

Although the amplification modules are generally described herein as performing a thermal cycling operation on the prepared solution, in other embodiment, an amplification module can perform any suitable thermal reaction to amplify nucleic acids within the solution. In some embodiments, any of the amplification modules described herein can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

For example, any of the sample input modules, sample preparation modules, amplification modules, heater assemblies, and detection modules shown and described herein can be used in any suitable diagnostic device. Such devices can include, for example, a single-use device that can be used in a point-of-care setting and/or in a user's home. Similarly stated, in some embodiments, the device (and any of the other devices shown and described herein) can be configured for use in a decentralized test facility. Further, in some embodiments, any of the sample input modules, sample preparation modules, amplification modules, heater assemblies, and detection modules shown and described herein can be included within a CLIA-waived device and/or can facilitate the operation of a device in accordance with methods that are CLIA waived. Similarly stated, in some embodiments, the sample input modules, the sample preparation modules, the amplification modules, and the detection modules shown and described herein can facilitate operation of a device in a sufficiently simple manner that can produce results with sufficient accuracy to pose a limited likelihood of misuse and/or to pose a limited risk of harm if used improperly. In some embodiments, the sample input modules, the sample preparation modules, the amplification modules, and the detection modules shown and described herein can be used in any of the diagnostic devices shown and described in International Patent Publication No. WO2016/109691, entitled "Devices and Methods for Molecular Diagnostic Testing," which is incorporated herein by reference in its entirety," which is incorporated herein by reference in its entirety.

In some embodiments, any of the methods described herein, such as the method 50 and the methods described with respect to FIGS. 17A-17C, can include the following time, temperature, and volume ranges provided in Table 4.

TABLE 4

Sample Ranges

| Item | Upper Value | Lower Value |
|---|---|---|
| Input sample volume from pipette | 5000 μL | 500 μL |
| Total volume of sample produced by amplification module | 1000 μL | 5 μL |
| Total time from actuation to signal | 20 minutes | 5 minutes |
| Time for RT-PCR (lysing and RT-PCR) | 10 minutes | 10 seconds |
| Time for RT-PCR lysing operation | 5 minutes | 0.5 seconds |
| Time for RT-PCR cDNA production operation | 5 minutes | 5 seconds |
| Ramp rate for RT-PCR lysing operation | 100 C/sec | 0.1 C sec |
| Ramp rate for RT-PCR cDNA production operation | 100 C/sec | 0.1 C sec |
| Time for RT enzyme inactivation | 5 minutes | 0.5 seconds |
| Ramp rate for RT enzyme inactivation | 100 C/sec | 0.1 C sec |
| Reagent volumes (R4, R5, R6) | 3000 μL | 1000 μL |

The devices and methods described herein can be used to analyze any suitable type of biological sample, such as a tissue sample (e.g., a blood sample). In some cases, the biological sample comprises a bodily fluid taken from a subject. In some cases, the bodily fluid includes one or more cells comprising nucleic acids. In some cases, the one or more cells comprise one or more microbial cells, including, but not limited to, bacteria, archaebacteria, protists, and fungi. In some cases, the biological sample includes one or more virus particles. In some cases, the biological sample includes one or more microbes that causes a sexually-transmitted disease. A sample may comprise a sample from a subject, such as whole blood; blood products; red blood cells; white blood cells; buffy coat; swabs; urine; sputum; saliva; semen; lymphatic fluid; endolymph; perilymph; gastric juice; bile; mucus; sebum; sweat; tears; vaginal secretion; vomit; feces; breast milk; cerumen; amniotic fluid; cerebrospinal fluid; peritoneal effusions; pleural effusions; biopsy samples; fluid from cysts; synovial fluid; vitreous humor; aqueous humor; bursa fluid; eye washes; eye aspirates; plasma; serum; pulmonary lavage; lung aspirates; animal, including human, tissues, including but not limited to, liver, spleen, kidney, lung, intestine, brain, heart, muscle, pancreas, cell cultures, as well as lysates, extracts, or materials and fractions obtained from the samples described above or any cells and microorganisms and viruses that may be present on or in a sample. A sample may include cells of a primary culture or a cell line. Examples of cell lines include, but are not limited to, 293-T human kidney cells, A2870 human ovary cells, A431 human epithelium, B35 rat neuroblastoma cells, BHK-21 hamster kidney cells, BR293 human breast cells, CHO chinese hamster ovary cells, CORL23 human lung cells, HeLa cells, or Jurkat cells. The sample may include a homogeneous or mixed population of microbes, including one or more of viruses, bacteria, protists, monerans, chromalveolata, archaea, or fungi. The biological sample can be a urine sample, a vaginal swab, a cervical swab, an anal swab, or a cheek swab. The biological sample can be obtained from a hospital, laboratory, clinical or medical laboratory.

The devices and methods described herein, however, are not limited to performing a molecular diagnostic test on human samples. In some embodiments, any of the devices and methods described herein can be used with veterinary samples, food samples, and/or environmental samples. Examples of environmental sources include, but are not limited to agricultural fields, lakes, rivers, water reservoirs, air vents, walls, roofs, soil samples, plants, and swimming pools. Examples of industrial sources include, but are not limited to clean rooms, hospitals, food processing areas, food production areas, food stuffs, medical laboratories, pharmacies, and pharmaceutical compounding centers. Examples of subjects from which polynucleotides may be isolated include multicellular organisms, such as fish, amphibians, reptiles, birds, and mammals. Examples of mammals include primates (e.g., apes, monkeys, gorillas), rodents (e.g., mice, rats), cows, pigs, sheep, horses, dogs, cats, or rabbits. In some examples, the mammal is a human.

In some embodiments, any of the devices or methods described herein can include a sample buffer (e.g., within a sample preparation module, sample transfer manifold, or reagent module) and/or can mix a sample buffer with the biological sample, or can use the sample buffer as a wash/blocking solution, as described herein. In some cases, the sample buffer can include bovine serum albumin and/or a detergent. In some cases, the sample buffer includes about 0.1% to 5% bovine serum albumin. In some cases, the sample buffer includes about 0.1%, 0.2%, 0.3%, 0.4%, 0.5%, 1%, 1.5%, 2%, 2.5%, 3%, 4%, or 5% bovine serum albumin. In some cases, the sample buffer includes about 0.1% to 20% detergent. In some cases, the sample buffer includes about 1%, 2%, 3%, 4%, 5%, 6%, 7%, 8%, 9%, or 10% detergent. In some cases, the detergent is Tween-20. The choice of sample buffer to be used may depend on the intended method. For example, the choice of sample buffer may different when a wash step will be used to when a wash step is not used. If a wash step will not be used then the sample buffer may be a buffer suitable for lysis and subsequent PCR reactions.

In some embodiments, a sample buffer can include Tris HCL, Tween-80, BSA, Proclin and Antifoam SE-15. In some embodiments, a sample buffer may have a composition of: 50 mM Tris pH 8.4, Tween-80, 2% (w/v), BSA, 0.25% (w/v), Proclin 300 0.03% (w/v), and Antifoam SE-15, 0.002% (v/v) made up in purified water. Tris HCL is a common buffer for PCR. When it is heated during thermocycling, the pH may drop, for example, a Tris buffer with pH of 8.4 at a temperature of 25° C. may drop to a pH of about ~7.4 when heated to about 95° C. The range of concentrations could be from 0.1 mM to 1 M. The pH range could be from 6 to 10. Any other PCR compatible buffer could be used, for example HEPES. Proclin 300 is a broad spectrum antimicrobial used as a preservative to ensure a long shelf life of the collection media. It could be used from 0.01% (w/v) to 0.1% (w/v). Many other antimicrobials are known in the art and could be used in a sample buffer. In some embodiments, a reagent or wash buffer can include Antifoam SE-15 to reduce foaming during manufacturing and fluidic movement through the device. It could be used from 0.001% (v/v) to 1% (v/v). Any other antifoam agent could also be used, for example, Antifoam 204, Antifoam A, Antifoam B, Antifoam C, or Antifoam Y-30.

In some embodiments, any of the amplification modules described can be configured to conduct a "rapid" PCR (e.g., completing at least 30 cycles in less than about 10 minutes), and rapid production of an output signal (e.g., via a detection module). Similarly stated, the amplification modules described herein can be configured to process volumes, to have dimensional sizes and/or be constructed from materials that facilitates a rapid PCR or amplification in less than about 10 minutes, less than about 9 minutes, less than about 8 minutes, less than about 7 minutes, less than about 6 minutes, or any range therebetween, as described herein.

In some embodiments, any of the detection modules described herein can include capture probes of any suitable structure or composition. Such capture probes can be, for example, any of single stranded nucleic acids, antibodies, or binding proteins. In some embodiments, the capture probes have the following general structure (DNA base sequences here are only examples, and will vary according to the target amplicon):

(SEQ ID NO: 4)
5' End- /5AmMC6/TCTCGTAAAGGGCAGCCCGCAAG -3'End

In other embodiments, the capture probes can be modified to also contain spacer molecules, as per this structure:

(SEQ ID NO: 4)
5' End- /5AmMC6//iSp18/TCTCGTAAAGGGCAGCCCGCAAG -3' End

Where /5AmMC6/ is the 5' Amino Modifier C6—Integrated DNA Technologies and /iSp18/ is the Int Spacer 18—Integrated DNA Technologies. In other embodiments, the capture probes can be modified to include only the intended DNA bases, as per this structure:

(SEQ ID NO: 4)
5' End- TCTCGTAAAGGGCAGCCCGCAAG -3'End

In other embodiments, the capture probes also include extra non-target bases, as per this structure:

(SEQ ID NO: 5)
5' End- GGGGGGG TCTCGTAAAGGGCAGCCCGCAAG -3 'End

In some embodiments, the capture probes can be formulated, designed or engineered to have a relatively high melting temperature (Tm) value (e.g., approximately 67° C.). In other embodiments, the capture probes can have a melting temperature (Tm) value that ranges from 35° C. to 85° C., 60° C. to 85° C., 60° C. to 75° C., 65° C. to 70° C., or 66° C. to 68° C. One advantage of capture probes having a high Tm value is that the flow cell can be heated to a wide range of temperatures during operation without causing the capture probe to release the target amplicon.

In some embodiments, the capture probes are designed against sequences from *Neisseria gonorrhoeae, Chlamydia trachomatis, Trichomonas vaginalis, Neisseria subflava* and a negative control sequence such as sequence from *Bacillus atrophaeus* or random bases.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or microinstructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The processor included within a control module (and any of the processors and/or controllers described herein) can be any processor configured to, for example, write data into and read data from the memory of the controller, and execute the instructions and/or methods stored within the memory. Furthermore, the processor can be configured to control operation of the other modules within the controller (e.g., the temperature feedback module and the flow module). Specifically, the processor can receive a signal including temperature data, current measurements or the like and determine an amount of power and/or current to be supplied to each heater assembly, the desired timing and sequence of the piston pulses and the like. For example, in some embodiments, the controller can be an 8-bit PIC microcontroller, which will control the power delivered to various heating assemblies and components within the amplification module 4600. This microcontroller can also contain code for and/or be configured to minimize the instantaneous power requirements on the power source.

In other embodiments, any of the processors described herein can be, for example, an application-specific integrated circuit (ASIC) or a combination of ASICs, which are designed to perform one or more specific functions. In yet other embodiments, the microprocessor can be an analog or digital circuit, or a combination of multiple circuits.

Any of the memory devices described herein can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the pressure feedback module and the position feedback module) can be implemented by the processor and/or stored within the memory.

Although various embodiments have been described as having particular features and/or combinations of components, other embodiments are possible having a combination of any features and/or components from any of embodiments as discussed above.

Any of the devices and methods described herein can be utilized to detect the presence or absence of nucleic acids associated with one or more bacterial cells in a biological sample. In some embodiments, the one or more bacterial cells are pathogens. In some embodiments, the one or more bacterial cells are infectious. Non-limiting examples of bacterial pathogens that can be detected include Mycobacteria (e.g., *M tuberculosis, M bovis, M avium, M leprae*, and *M africanum*), rickettsia, mycoplasma, chlamydia, and legionella. Some examples of bacterial infections include, but are not limited to, infections caused by Gram positive bacillus (e.g., *Listeria, Bacillus* such as *Bacillus anthracis, Erysipelothrix* species), Gram negative bacillus (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio* and *Y ersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, Pneumococcus species, *Staphylococcus* species, and *Neisseria* species. Specific examples of infectious bacteria include, but are not limited to: *Helicobacter pyloris, Legionella pneumophilia, Mycobacterium tuberculosis, Mycobacterium avium, Mycobacterium intracellulare, Mycobacterium kansaii, Mycobacterium gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, Erysipelothrix rhusiopathiae, Clostridium tetani, Enterobacter aerogenes, Klebsiella pneumoniae, Pasteurella multocida, Fusobacterium nucleatum, Streptobacillus moniliformis, Treponema pallidium, Treponema pertenue, Leptospira, Rickettsia,* and *Actinomyces israelii, Acinetobacter, Bacillus, Bordetella, Borrelia, Brucella, Campylobacter, Chlamydia, Chlamydophila, Clostridium, Corynebacterium, Enterococcus, Haemophilus, Helicobacter, Mycobacterium, Mycoplasma, Stenotrophomonas, Treponema, Vibrio, Yersinia, Acinetobacter baumanii, Bordetella pertussis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Corynebacterium diphtheriae, Enterobacter sazakii, Enterobacter agglomerans, Enterobacter cloacae, Enterococcus faecalis, Enterococcus faecium, Escherichia coli, Francisella tularensis, Helicobacter pylori, Legionella pneumophila, Leptospira interrogans, Mycobacterium leprae, Mycobacterium tuberculosis, Mycobacterium ulcerans, Mycoplasma pneumoniae, Pseudomonas aeruginosa, Rickettsia rickettsii, Salmonella typhi, Salmonella typhimurium, Salmonella enterica, Shigella sonnei, Staphylococcus epidermidis, Staphylococcus saprophyticus, Stenotrophomonas maltophilia, Vibrio cholerae, Yersinia pestis,* and the like. In some instances, the infectious bacteria is *Neisseria gonorrhoeae* or *Chlamydia trachomatis*.

Any of the devices and methods described herein can be utilized to detect the presence or absence of nucleic acids associated with one or more viruses in a biological sample. Non-limiting examples of viruses include the herpes virus (e.g., human cytomegalomous virus (HCMV), herpes simplex virus I (HSV-1), herpes simplex virus 2 (HSV-2), varicella zoster virus (VZV), Epstein-Barr virus), influenza A virus and Hepatitis C virus (HCV) or a picornavirus such as Coxsackievirus B3 (CVB3). Other viruses may include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, filo virus, Adenovirus, Human herpesvirus, type 8, Human papillomavirus, BK virus, JC virus, Smallpox, Hepatitis B virus, Human bocavirus, Parvovirus B 19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV). In some embodiments, the virus is an enveloped virus. Examples of such enveloped viruses include, but are not limited to, viruses that are members of the hepadnavirus family, herpesvirus family, iridovirus family, poxvirus family, flavivirus family, togavirus family, retrovirus family, coronavirus family, Filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicellazoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma—associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoon pox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta torn virus (PTV), Tacaribe virus and Tamiami virus. In some embodiments, the virus is a non-enveloped virus, examples of which include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2, BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses A1-22, 24 (CA1-22 and CA24, CA23 (echovirus 9)), human coxsackieviruses (B1-6 (CB1-6)), human echoviruses 1-7, 9, 11-27, 29-33, vilyuish virus, simian enteroviruses 1-18 (SEVI-18), porcine enteroviruses 1-11 (PEV1-11), bovine enteroviruses 1-2 (BEVI-2), hepatitis A virus, rhinoviruses, hepatoviruses, cardio viruses, aphthoviruses and echoviruses. The virus may be phage. Examples of phages include, but are not limited to T4, TS, λ phage, T7 phage, G4, Pl, φ6, Thermoproteus tenax virus 1, M13, MS2, Qβ, φX174, Φ29, PZA, Φ15, BS32, Bl03, M2Y (M2), Nf, GA-I, FWLBc1, FWLBc2, FWLLm3, B4. The reference database may comprise sequences for phage that are pathogenic, protective, or both. In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Arna virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus. In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus. In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O' nyong'nyong virus, and the chikungunya virus; a member of the Poxyiridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or HINT swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picomaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively).

Any of the devices and methods described herein can be utilized to detect the presence or absence of nucleic acids associated with one or more fungi in a biological sample. Examples of infectious fungal agents include, without limitation *Aspergillus, Blastomyces, Coccidioides, Cryptococcus, Histoplasma, Paracoccidioides, Sporothrix*, and at least three genera of Zygomycetes. The above fungi, as well as many other fungi, can cause disease in pets and companion animals. The present teaching is inclusive of substrates that contact animals directly or indirectly. Examples of organisms that cause disease in animals include *Malassezia furfur, Epidermophyton floccosur, Trichophyton mentagrophytes, Trichophyton rubrum, Trichophyton tonsurans, Trichophyton equinum, Dermatophilus congolensis, Microsporum canis, Microsporu audouinii, Microsporum gypseum, Malassezia ovale, Pseudallescheria, Scopulariopsis, Scedosporium,* and *Candida albicans*. Further examples of fungal infectious agent include, but are not limited to, *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus,* or *Rhizopus arrhizus*.

Any of the devices and methods described herein can be utilized to detect the presence or absence of nucleic acids associated with one or more parasites in a biological sample. Non-limiting examples of parasites include *Plasmodium, Leishmania, Babesia, Treponema, Borrelia, Trypanosoma, Toxoplasma gondii, Plasmodium falciparum, P. vivax, P. ovale, P. malariae, Trypanosoma* spp., or *Legionella* spp. In some cases, the parasite is *Trichomonas vaginalis*.

What is claimed is:

1. An apparatus, comprising:

a housing of a molecular diagnostic device; and a reagent module disposed within the housing, the reagent module including a reagent housing, a reagent container containing a reagent sealed therein by a frangible seal, a puncturer, and a deformable support member, the reagent housing defining a reagent reservoir into which the reagent is released from the reagent container when the puncturer pierces the frangible seal of the reagent container, the deformable support member including a sealing portion and a coupling portion, the sealing portion coupled to the reagent housing to fluidically isolate the reagent reservoir, the coupling portion coupled to at least one of the puncturer or the reagent container;

the deformable support member configured to deform from a first configuration to a second configuration in response to an actuation force exerted on the deformable support member, the deformable support member maintaining the puncturer spaced apart from the frangible seal when the deformable support member is in the first configuration, the puncturer piercing the frangible seal when the deformable support member is in the second configuration.

2. The apparatus of claim 1, wherein the deformable support member is biased towards the first configuration.

3. The apparatus of claim 2, wherein the deformable support member exerts a biasing force on at least one of the puncturer or the reagent container, the biasing force sufficient to support the at least one of the puncturer or the reagent container in a position to maintain the puncturer spaced apart from the frangible seal.

4. The apparatus of claim 3, wherein:

the puncturer is coupled within the reagent reservoir;

the reagent container is movably disposed within the reagent reservoir; and the deformable support member is coupled to the reagent container such that the reagent container moves from a first container position to a second container position within the reagent reservoir when the deformable support member transitions from the first configuration to the second configuration.

5. The apparatus of claim 3, wherein:

the puncturer is movably disposed within the reagent reservoir; and the deformable support member is coupled to the puncturer such that the puncturer moves from a first puncturer position to a second puncturer position and into contact with the frangible seal when the deformable support member transitions from the first configuration to the second configuration.

6. The apparatus of claim 1, further comprising:

a sample preparation module within the housing, the sample preparation module defining a sample input volume that receives a biological sample and an input opening through which the sample input volume can be accessed, the sample preparation module including a heater configured to heat the biological sample to produce an input solution; and a lid movably coupled to the housing, the lid including a cover portion and a reagent actuator, the lid configured to move relative to the housing between a first lid position and a second lid position, the input opening being exposed when the lid is in the first lid position, the cover portion of the lid covering the input opening when the lid is in the second lid position, the reagent actuator configured to cause the deformable support member to deform from the first configuration to the second configuration when the lid is moved from the first lid position to the second lid position.

7. The apparatus of claim 1, further comprising:

a detection module within the housing, the detection module including a detection surface configured to capture a target molecule from a biological sample, the detection module in fluid communication with the reagent module such that a signal indicating a presence of the target molecule is produced in response to the reagent being conveyed into the detection module.

8. The apparatus of claim 7, wherein the reagent is one of a first reagent or a second reagent, the first reagent formulated to be bound to the target molecule in response to the first reagent being conveyed into the detection module, the second reagent formulated to produce the signal when catalyzed by the first reagent.

9. The apparatus of claim 8, wherein the second reagent is a precipitating substrate formulated to produce an insoluble colored particle when the second reagent is contacted with the first reagent.

10. The apparatus of claim 7, wherein:

the reagent container is a first reagent container;

the puncturer is a first puncturer;

the reagent is a first reagent, the first reagent being one of a catalyzing reagent formulated to be bound to the target molecule in response to the first reagent being conveyed into the detection module or a precipitating reagent formulated to produce the signal when catalyzed by the catalyzing reagent;

the reagent module includes a second reagent container containing a solution; and the coupling portion of the deformable support member is coupled to at least one of a second puncturer or the second reagent container, the deformable support member maintaining the second puncturer spaced apart from the second reagent container when the deformable support member is in the first configuration, the second puncturer piercing the second reagent container when the deformable support member is in the second configuration.

11. An apparatus, comprising:

a housing of a molecular diagnostic device; and a reagent module disposed within the housing, the reagent module including a reagent housing, a reagent container containing a reagent sealed therein, a puncturer, and a deformable support member, the reagent housing defining a reagent reservoir into which the reagent is released from the reagent container when the puncturer pierces a portion of the reagent container, the deformable support member including a sealing portion and a coupling portion, the sealing portion coupled to the reagent housing to fluidically isolate the reagent reservoir, the coupling portion coupled to at least one of the puncturer or the reagent container, the deformable support member configured to deform from a first configuration to a second configuration in response to an actuation force exerted on the deformable support member, the deformable support member maintaining the puncturer spaced apart from the portion of the reagent container when the deformable support member is in the first configuration, the puncturer piercing the portion of the reagent container when the deformable support member is in the second configuration; and a sample preparation module within the housing, the sample preparation module defining a sample input volume that receives a biological sample and an input opening through which the sample input volume can be accessed, the sample preparation module including a heater configured to heat the biological sample to produce an input solution; and a lid movably coupled to the housing, the lid including a cover portion and a reagent actuator, the lid configured to move relative to the housing between a first lid position and a second lid position, the input opening being exposed when the lid is in the first lid position, the cover portion of the lid covering the input opening when the lid is in the second lid position, the reagent actuator configured to cause the deformable support member to deform from the first configuration to the second configuration when the lid is moved from the first lid position to the second lid position.

12. A molecular diagnostic device, comprising:

a reagent housing including a puncturer and defining a reagent reservoir;

a reagent container containing a reagent sealed therein by a frangible seal, the reagent configured to be released from the reagent container into the reagent reservoir when the puncturer pierces the frangible seal of the reagent container; and a deformable support member including a sealing portion and a coupling portion, the sealing portion coupled to the reagent housing to fluidically isolate the reagent reservoir, the coupling portion coupled to the reagent container, the deformable support member configured to deform from a first configuration to a second configuration in response to an actuation force exerted on the deformable support member, the deformable support member maintaining the puncturer spaced apart from the frangible seal when the deformable support member is in the first configuration, the puncturer piercing the frangible seal when the deformable support member is in the second configuration.

* * * * *

SEQUENCE LISTING

```
<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tggcactacc cctctccgta ttcac                                           25

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtacgggcga ccccacgatg ac                                              22

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cacatcgata gatcaaggtg cctacaagc                                       29

<210> SEQ ID NO 4
<211> LENGTH: 23
<212> TYPE: DNA
<213> ORGANISM: Artificial Sequence
```

-continued

```
<220> FEATURE:
<223> OTHER INFORMATION: Description of Artificial Sequence: Synthetic
      probe

<400> SEQUENCE: 4
tctcgtaaag ggcagcccgc aag                                           23

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5 ggggggtct cgtaaagggc agcccgcaag                                     30
```